United States Patent
Saville et al.

(10) Patent No.: US 10,450,548 B2
(45) Date of Patent: Oct. 22, 2019

(54) COMPOSITIONS AND METHODS FOR BIOLOGICAL PRODUCTION OF LACTATE FROM $C_1$ COMPOUNDS USING LACTATE DEHYDROGENASE TRANSFORMANTS

(71) Applicant: CALYSTA, INC., Menlo Park, CA (US)

(72) Inventors: Renee M. Saville, Mountain View, CA (US); Sungwon Lee, Fremont, CA (US); Drew D. Regitsky, San Francisco, CA (US); Sol M. Resnick, Encinitas, CA (US); Joshua A. Silverman, Los Altos Hills, CA (US)

(73) Assignee: CALYSTA, INC., Menlo Park, CA (US)

( * ) Notice: Subject to any disclaimer, the term of this patent is extended or adjusted under 35 U.S.C. 154(b) by 0 days.

(21) Appl. No.: 14/898,948

(22) PCT Filed: Jun. 18, 2014

(86) PCT No.: PCT/US2014/043053
§ 371 (c)(1),
(2) Date: Dec. 16, 2015

(87) PCT Pub. No.: WO2014/205146
PCT Pub. Date: Dec. 24, 2014

(65) Prior Publication Data
US 2016/0369246 A1    Dec. 22, 2016

Related U.S. Application Data

(60) Provisional application No. 61/836,609, filed on Jun. 18, 2013, provisional application No. 61/928,390, filed on Jan. 16, 2014.

(51) Int. Cl.
*C12N 1/20* (2006.01)
*C12N 9/04* (2006.01)
(Continued)

(52) U.S. Cl.
CPC .......... *C12N 9/0006* (2013.01); *C07B 59/001* (2013.01); *C07C 59/08* (2013.01);
(Continued)

(58) Field of Classification Search
None
See application file for complete search history.

(56) References Cited

U.S. PATENT DOCUMENTS 3,846,289 A    11/1974  Jens et al.
4,009,098 A    2/1977  Jeris
(Continued)

FOREIGN PATENT DOCUMENTS

EP    1 932 910 A1    6/2008
WO    02/18617 A     3/2002
(Continued)

OTHER PUBLICATIONS

Uniprot Accession No. D5DYT6_BACMQ, published May 16, 2012.*

(Continued)

*Primary Examiner* — Richard C Ekstrom
(74) *Attorney, Agent, or Firm* — Seed IP Law Group LLP

(57) ABSTRACT

The present disclosure provides non-naturally occurring c1 microorganisms useful for the production of lactate and related compositions, as well as methods for the biologically production of lactate. In specific embodiments, the present disclosure provides non-naturally occurring methanotrophic bacteria which are useful for producing lactate from c1 substrates.

18 Claims, 3 Drawing Sheets

Specification includes a Sequence Listing.

(51) Int. Cl.
| | |
|---|---|
| *C12P 7/56* | (2006.01) |
| *C07B 59/00* | (2006.01) |
| *C07C 59/08* | (2006.01) |
| *C12N 15/74* | (2006.01) |

(52) U.S. Cl.
CPC ............... *C12N 1/20* (2013.01); *C12N 15/74* (2013.01); *C12P 7/56* (2013.01); *C12Y 101/01027* (2013.01); *C12Y 101/01028* (2013.01); *C07B 2200/05* (2013.01)

(56) References Cited

U.S. PATENT DOCUMENTS

| | | | |
|---|---|---|---|
| H1430 H | 4/1995 | Apel et al. | |
| 6,818,424 B2 | 11/2004 | DiCosimo et al. | |
| 7,098,005 B2 | 8/2006 | Dicosimo et al. | |
| 7,700,332 B1 | 4/2010 | Rajgarhia et al. | |
| 7,931,806 B2 | 4/2011 | Logan et al. | |
| 8,005,620 B2 | 8/2011 | Gustafsson et al. | |
| 2003/0003528 A1 | 1/2003 | Brzostowicz et al. | |
| 2003/0166174 A1* | 9/2003 | Ono | C12P 13/04 435/106 |
| 2007/0105202 A1 | 5/2007 | Ishida et al. | |
| 2008/0026005 A1 | 1/2008 | Miguez et al. | |
| 2010/0003731 A1* | 1/2010 | Ito | C12N 9/0006 435/139 |
| 2010/0221813 A1 | 9/2010 | Miguez et al. | |
| 2015/0111265 A1 | 4/2015 | Lidstrom et al. | |
| 2016/0237398 A1 | 8/2016 | Kalyuzhnaya et al. | |

FOREIGN PATENT DOCUMENTS

| | | | |
|---|---|---|---|
| WO | 03/102201 A2 | 12/2003 | |
| WO | WO 2013066848 A1 * | 5/2013 | ................ C12P 5/00 |
| WO | 2014/012055 A1 | 1/2014 | |
| WO | 2014/047209 A1 | 3/2014 | |
| WO | 2014/062703 A1 | 4/2014 | |
| WO | 2014/066670 A1 | 5/2014 | |
| WO | 2014/074886 A1 | 5/2014 | |
| WO | 2014/089436 A1 | 6/2014 | |
| WO | 2014/138419 A1 | 9/2014 | |
| WO | WO 2015155790 A2 * | 10/2015 | ........... C12N 9/0006 |

OTHER PUBLICATIONS

GenEmbl Accession No. AY205157, published Apr. 4, 2003.*

Akhverdyan et al., "Application of the bacteriophage Mu-driven system for the integration/amplification of target genes in the chromosomes of engineered Gram-negative bacteria—mini review," *Applied Microbiology and Biotechnology* 91(4): 857-871, 2011.

Ali et al., "Development and validation of promoter-probe vectors for the study of methane monooxygenase gene expression in *Methylococcus capsulatus* Bath," *Microbiology* 155(3):761-771, 2009.

Angermayr et al., "Engineering a Cyanobacterial Cell Factory for Production of Lactic Acid," *Applied and Environmental Microbiology* 78(19):7098-7106, 2012. (10 pages).

Brosius, "Toxicity of an overproduced foreign gene product in *Escherichia coli* and its use in plasmid vectors for the selection of transcription terminators," *Gene* 27(2):161-172, 1984.

Drumright et al., "Polylactic Acid Technology," *Advanced Materials* 12(23):1841-1846, 2000.

Hanson et al., "Methanotrophic Bacteria, "*Microbiological Reviews* 60(2):439-471, 1996.

Ilmén et al., "Efficient Production of $_L$-Lactic Acid From Xylose by *Pichia stipitis*," *Applied and Environmental Microbiology* 73(1):117-123, 2007.

Ilmén et al., "Production of L-lactic acid by the yeast *Candida sonorensis* expressing heterologous bacterial and fungal lactate dehydrogenases," *Microbial Cell Factories* 12:53, 2013. (15 pages).

Ishida et al., "Metabolic Engineering of *Saccharomyces cerevisiae* for Efficient Production of Pure $_L$-(+)-Lactic Acid," *Applied Biochemistry and Biotechnology* 131(1-3):795-807, 2006.

Joseph et al., "Utilization of Lactic Acid Bacterial Genes in *Synechocystis* sp. PCC 6803 in the Production of Lactic Acid," *Bioscience, Biotechnology, and Biochemistry* 77(5):966-970, 2013.

Södergård et al., "Properties of lactic acid based polymers and their correlation with composition," *Progress in Polymer Science* 27(6):1123-1163, 2002.

Springer et al., "Sequence and characterization of mxaB, a response regulator involved in regulation of methanol oxidation, and of mxaW, a methanol-regulated gene in *Methylobacterium extorquens* AM1," *FEMS Microbiology Letters* 160(1):119-124, 1998.

Stolyar et al., "Role of multiple gene copies in particulate methane monooxygenase activity in the methane-oxidizing bacterium *Methylococcus capsulatus* Bath," *Microbiology* 145(5):1235-1244, 1999.

Stolyar et al., "Search for Systems of Genetic Exchange in Methane-Oxidizing Bacteria," *Mikrobiologiya* 64(5):686-691, 1995. (9 pages).

Templeton et al., "Variable carbon isotope fractionation expressed by aerobic $CH_4$-oxidizing bacteria," *Geochimica et Cosmochimica Acta* 70(7):1739-1752, 2006.

Toyama et al., "Construction of insertion and deletion mxa mutants of *Methylobacterium extorquens* AM1 by electroporation," *FEMS Microbiology Letters* 166(1):1-7, 1998.

Toyama et al., "pqqA is not required for biosynthesis of pyrroloquinoline quinone in *Methylobacterium extorquens* AM1," *Microbiology* 144(1):183-191, 1998.

Toyama et al., "Sequence analysis of pqq genes required for biosynthesis of pyrroloquinoline quinone in *Methylobacterium extorquens* AM1 and the purification of a biosynthetic intermediate," *Microbiology* 143(2):595-602, 1997.

Van Dien et al., "Reconstruction of $C_3$ and $C_4$ metabolism in *Methylobacterium extorquens* AM1 using transposon mutagenesis," *Microbiology* 149(3):601-609, 2003.

Vink et al., "Applications of life cycle assessment to NatureWorks™ polylactide (PLA) production," *Polymer Degradation and Stability* 80(3):403-419, 2003.

Whiticar et al., "Methane oxidation in sediment and water column environments—Isotope evidence, " *Organic Geochemistry* 10(4-6):759-768, 1986.

Whiticar, "A geochemial perspective of natural gas and atmospheric methane, " *Organic Geochemistry* 16(1-3):531-547, 1990.

Yoshida et al., "Improved conditions for the transformation by electroporation of the extracellular polysaccharide-producing methylotroph *Methylobacillus* sp.," *Biotechnology Letters* 23(10):787-791, 2001.

* cited by examiner

SEQUENCE LISTING

<160> NUMBER OF SEQ ID NOS: 67

<210> SEQ ID NO 1
<211> LENGTH: 987
<212> TYPE: DNA
<213> ORGANISM: Artificial
<220> FEATURE:
<223> OTHER INFORMATION: Synthetic construct (Streptococcus bovis LDH)
<220> FEATURE:
<221> NAME/KEY: CDS
<222> LOCATION: (1)..(987)

<400> SEQUENCE: 1

```
atg acc gcg acc aag cag cac aaa aaa gtt atc ctg gtt gga gat ggg        48
Met Thr Ala Thr Lys Gln His Lys Lys Val Ile Leu Val Gly Asp Gly
1               5                   10                  15 gcc gtg ggc tcg tcg tat gcg ttc gcc ctc gtc aac cag ggc ata gcc        96
Ala Val Gly Ser Ser Tyr Ala Phe Ala Leu Val Asn Gln Gly Ile Ala
            20                  25                  30 cag gaa ctg ggc atc atc gag atc ccg cag ttg ttc gac aaa gcc gtc       144
Gln Glu Leu Gly Ile Ile Glu Ile Pro Gln Leu Phe Asp Lys Ala Val
        35                  40                  45 ggt gac gcc gag gac ctc agc cac gct ctt gcc ttc acc agc cct aaa       192
Gly Asp Ala Glu Asp Leu Ser His Ala Leu Ala Phe Thr Ser Pro Lys
    50                  55                  60 aag atc tac gcg gca aag tac gag gat tgc gcc gac gcg gac ctg gta       240
Lys Ile Tyr Ala Ala Lys Tyr Glu Asp Cys Ala Asp Ala Asp Leu Val
65                  70                  75                  80 gtg atc acc gcc gga gcg ccc cag aag ccc ggt gaa acg cgc ctg gac       288
Val Ile Thr Ala Gly Ala Pro Gln Lys Pro Gly Glu Thr Arg Leu Asp
                85                  90                  95 ctg gtc ggg aag aac ttg gct atc aat aag tca att gtc acc gaa gtg       336
Leu Val Gly Lys Asn Leu Ala Ile Asn Lys Ser Ile Val Thr Glu Val
            100                 105                 110 gtc aag tcg ggg ttc aac ggc att ttc ctc gtg gcc gcg aat cca gtg       384
Val Lys Ser Gly Phe Asn Gly Ile Phe Leu Val Ala Ala Asn Pro Val
        115                 120                 125 gac gtg ctg aca tac agc acc tgg aag ttc tcc ggc ttc ccg aag gaa       432
Asp Val Leu Thr Tyr Ser Thr Trp Lys Phe Ser Gly Phe Pro Lys Glu
    130                 135                 140 cgg gtc atc ggt agc ggc acg agc ctg gac tcg gcc agg ttt cgg caa       480
Arg Val Ile Gly Ser Gly Thr Ser Leu Asp Ser Ala Arg Phe Arg Gln
145                 150                 155                 160 gcc ctg gcg gag aag ctg gat gtc gat gcc cgc tcc gtc cac gca tac       528
Ala Leu Ala Glu Lys Leu Asp Val Asp Ala Arg Ser Val His Ala Tyr
                165                 170                 175 atc atg ggc gag cat ggc gac tcg gag ttc gcc gtg tgg agc cat gcg       576
Ile Met Gly Glu His Gly Asp Ser Glu Phe Ala Val Trp Ser His Ala
            180                 185                 190 aat gtc gct ggg gtg aat ctg gag aac tat ctg aaa gac gtc cag aac       624
Asn Val Ala Gly Val Asn Leu Glu Asn Tyr Leu Lys Asp Val Gln Asn
        195                 200                 205 gtg aac gaa gcg gaa ctc gtg gag ctg ttc gag ggc gtc cgt gat gcg       672
Val Asn Glu Ala Glu Leu Val Glu Leu Phe Glu Gly Val Arg Asp Ala
    210                 215                 220 gcg tat tcc atc atc aac aaa aag ggc gcc act ttc tac ggc atc gcc       720
Ala Tyr Ser Ile Ile Asn Lys Lys Gly Ala Thr Phe Tyr Gly Ile Ala
225                 230                 235                 240 gtg gcg ctc gcc cgg atc acg aag gcc att ttg aac gat gaa aac gcc       768
Val Ala Leu Ala Arg Ile Thr Lys Ala Ile Leu Asn Asp Glu Asn Ala
                245                 250                 255
```

| | | | | | | | | | | | | | | | | |
|---|---|---|---|---|---|---|---|---|---|---|---|---|---|---|---|---|
| gtc | ctg | ccg | ctg | tcc | gtg | ttc | cag | gaa | ggg | cag | tat | ccg | ggt | gtg | acc | 816 |
| Val | Leu | Pro | Leu | Ser | Val | Phe | Gln | Glu | Gly | Gln | Tyr | Pro | Gly | Val | Thr | |
| | | 260 | | | | | 265 | | | | | 270 | | | | |
| gac | tgc | tac | atc | ggc | cag | ccc | gcc | atc | gtc | gga | gcc | cat | ggc | atc | gta | 864 |
| Asp | Cys | Tyr | Ile | Gly | Gln | Pro | Ala | Ile | Val | Gly | Ala | His | Gly | Ile | Val | |
| | | 275 | | | | | 280 | | | | | 285 | | | | |
| cgc | ccc | gtc | aac | atc | ccg | ctc | aac | gac | gcg | gag | cag | caa | aag | atg | gaa | 912 |
| Arg | Pro | Val | Asn | Ile | Pro | Leu | Asn | Asp | Ala | Glu | Gln | Gln | Lys | Met | Glu | |
| | 290 | | | | | 295 | | | | | 300 | | | | | |
| gca | tct | gca | aaa | gaa | ctg | aag | gcc | atc | atc | gac | gaa | gcc | ttc | tcc | aaa | 960 |
| Ala | Ser | Ala | Lys | Glu | Leu | Lys | Ala | Ile | Ile | Asp | Glu | Ala | Phe | Ser | Lys | |
| 305 | | | | 310 | | | | | 315 | | | | | 320 | | |
| gaa | gag | ttt | gcc | agt | gcg | gcg | aag | taa | | | | | | | | 987 |
| Glu | Glu | Phe | Ala | Ser | Ala | Ala | Lys | | | | | | | | | |
| | | | | 325 | | | | | | | | | | | | |

<210> SEQ ID NO 2
<211> LENGTH: 328
<212> TYPE: PRT
<213> ORGANISM: Artificial
<220> FEATURE:
<223> OTHER INFORMATION: Synthetic Construct

<400> SEQUENCE: 2

Met Thr Ala Thr Lys Gln His Lys Lys Val Ile Leu Val Gly Asp Gly
1               5                   10                  15

Ala Val Gly Ser Ser Tyr Ala Phe Ala Leu Val Asn Gln Gly Ile Ala
            20                  25                  30

Gln Glu Leu Gly Ile Ile Glu Ile Pro Gln Leu Phe Asp Lys Ala Val
        35                  40                  45

Gly Asp Ala Glu Asp Leu Ser His Ala Leu Ala Phe Thr Ser Pro Lys
    50                  55                  60

Lys Ile Tyr Ala Ala Lys Tyr Glu Asp Cys Ala Asp Ala Asp Leu Val
65                  70                  75                  80

Val Ile Thr Ala Gly Ala Pro Gln Lys Pro Gly Glu Thr Arg Leu Asp
                85                  90                  95

Leu Val Gly Lys Asn Leu Ala Ile Asn Lys Ser Ile Val Thr Glu Val
            100                 105                 110

Val Lys Ser Gly Phe Asn Gly Ile Phe Leu Val Ala Ala Asn Pro Val
        115                 120                 125

Asp Val Leu Thr Tyr Ser Thr Trp Lys Phe Ser Gly Phe Pro Lys Glu
    130                 135                 140

Arg Val Ile Gly Ser Gly Thr Ser Leu Asp Ser Ala Arg Phe Arg Gln
145                 150                 155                 160

Ala Leu Ala Glu Lys Leu Asp Val Asp Ala Arg Ser Val His Ala Tyr
                165                 170                 175

Ile Met Gly Glu His Gly Asp Ser Glu Phe Ala Val Trp Ser His Ala
            180                 185                 190

Asn Val Ala Gly Val Asn Leu Glu Asn Tyr Leu Lys Asp Val Gln Asn
        195                 200                 205

Val Asn Glu Ala Glu Leu Val Glu Leu Phe Glu Gly Val Arg Asp Ala
    210                 215                 220

Ala Tyr Ser Ile Ile Asn Lys Lys Gly Ala Thr Phe Tyr Gly Ile Ala
225                 230                 235                 240

Val Ala Leu Ala Arg Ile Thr Lys Ala Ile Leu Asn Asp Glu Asn Ala
                245                 250                 255

Val Leu Pro Leu Ser Val Phe Gln Glu Gly Gln Tyr Pro Gly Val Thr

```
                 260                 265                 270
Asp Cys Tyr Ile Gly Gln Pro Ala Ile Val Gly Ala His Gly Ile Val
            275                 280                 285

Arg Pro Val Asn Ile Pro Leu Asn Asp Ala Glu Gln Gln Lys Met Glu
            290                 295                 300

Ala Ser Ala Lys Glu Leu Lys Ala Ile Ile Asp Glu Ala Phe Ser Lys
305                 310                 315                 320

Glu Glu Phe Ala Ser Ala Ala Lys
                325

<210> SEQ ID NO 3
<211> LENGTH: 924
<212> TYPE: DNA
<213> ORGANISM: Artificial
<220> FEATURE:
<223> OTHER INFORMATION: Synthetic construct (Lactobacillus helveticus
      LDH)
<220> FEATURE:
<221> NAME/KEY: CDS
<222> LOCATION: (1)..(924)

<400> SEQUENCE: 3 atg tct agg aaa gtg ttt ctt gtg ggt gat ggt gcg gtg ggg tca acg      48
Met Ser Arg Lys Val Phe Leu Val Gly Asp Gly Ala Val Gly Ser Thr
1               5                   10                  15 ttt gcg aac gat ttg ttg cag aat gcg aaa gtg gac gag ctc gcc atc      96
Phe Ala Asn Asp Leu Leu Gln Asn Ala Lys Val Asp Glu Leu Ala Ile
                20                  25                  30 ttc gag gtc gcc aag gat cgg ccg gta ggc gac gcg atg gac ctg gaa     144
Phe Glu Val Ala Lys Asp Arg Pro Val Gly Asp Ala Met Asp Leu Glu
            35                  40                  45 gat atc acc ccc ttc atg ggc cag acg gat atc cac ccg gca gac tac     192
Asp Ile Thr Pro Phe Met Gly Gln Thr Asp Ile His Pro Ala Asp Tyr
        50                  55                  60 tcg gac gcg aaa gac gcc gac gtg tgc gtc atc gct gcg ggt gtg ccc     240
Ser Asp Ala Lys Asp Ala Asp Val Cys Val Ile Ala Ala Gly Val Pro
65                  70                  75                  80 cgc aag ccc ggt gaa aca cgg ctc gac ctg gtc gcg aaa aac gtc aag     288
Arg Lys Pro Gly Glu Thr Arg Leu Asp Leu Val Ala Lys Asn Val Lys
                85                  90                  95 ata ctg aag tcc atc gtg cag ccg gtc gtg gaa tcc ggc ttc aaa ggc     336
Ile Leu Lys Ser Ile Val Gln Pro Val Val Glu Ser Gly Phe Lys Gly
            100                 105                 110 gtg ttc gtt gtg tcg gcg aac ccg gtc gac att ctg acc acc ctc acg     384
Val Phe Val Val Ser Ala Asn Pro Val Asp Ile Leu Thr Thr Leu Thr
        115                 120                 125 cag aag ttg agt ggc ttc ccg aag aac cgc gtg atc gga acc ggc acc     432
Gln Lys Leu Ser Gly Phe Pro Lys Asn Arg Val Ile Gly Thr Gly Thr
    130                 135                 140 agc ctg gat tcg atg cgt ctg cgc gtg gag ctc gcc aag aaa ctg aac     480
Ser Leu Asp Ser Met Arg Leu Arg Val Glu Leu Ala Lys Lys Leu Asn
145                 150                 155                 160 gtt ccc gtc gct aag gtc aat agc atg gtc ctc gga gaa cac ggc gac     528
Val Pro Val Ala Lys Val Asn Ser Met Val Leu Gly Glu His Gly Asp
                165                 170                 175 acg tcg ttc gag aat ttc gac gag agc acc gtg gac ggc aag ccg ctg     576
Thr Ser Phe Glu Asn Phe Asp Glu Ser Thr Val Asp Gly Lys Pro Leu
            180                 185                 190 cgc gac tac gcc gag atc aac gac gat gtc ctg agc gag atc gaa acc     624
Arg Asp Tyr Ala Glu Ile Asn Asp Asp Val Leu Ser Glu Ile Glu Thr
        195                 200                 205
```

```
gac gtc cga aag aaa ggc gag aag atc atc gcc aaa aag ggc gcc acg      672
Asp Val Arg Lys Lys Gly Glu Lys Ile Ile Ala Lys Lys Gly Ala Thr
    210                 215                 220 ttc tat ggg gtc gcc atg atg ctg acc cag atc gta tcc gcc att ctg      720
Phe Tyr Gly Val Ala Met Met Leu Thr Gln Ile Val Ser Ala Ile Leu
225                 230                 235                 240 gac aat cgg tcc atc tgc ctg ccg ctg agc gcc cct atc aac ggc gaa      768
Asp Asn Arg Ser Ile Cys Leu Pro Leu Ser Ala Pro Ile Asn Gly Glu
                245                 250                 255 tat ggc atc aag cat gac ctc tac ctg ggc acc cca gcc gtg atc aac      816
Tyr Gly Ile Lys His Asp Leu Tyr Leu Gly Thr Pro Ala Val Ile Asn
            260                 265                 270 ggg gaa ggg atc gaa cag gtc atc gag act aag ctg tcg gat gcc gaa      864
Gly Glu Gly Ile Glu Gln Val Ile Glu Thr Lys Leu Ser Asp Ala Glu
        275                 280                 285 aag gcc aag atg att aac tcc gca gat aag atg caa gaa gtc ctg ggc      912
Lys Ala Lys Met Ile Asn Ser Ala Asp Lys Met Gln Glu Val Leu Gly
    290                 295                 300 gga atc gag taa                                                      924
Gly Ile Glu
305
```

<210> SEQ ID NO 4
<211> LENGTH: 307
<212> TYPE: PRT
<213> ORGANISM: Artificial
<220> FEATURE:
<223> OTHER INFORMATION: Synthetic Construct

<400> SEQUENCE: 4

```
Met Ser Arg Lys Val Phe Leu Val Gly Asp Gly Ala Val Gly Ser Thr
1               5                   10                  15

Phe Ala Asn Asp Leu Leu Gln Asn Ala Lys Val Asp Glu Leu Ala Ile
            20                  25                  30

Phe Glu Val Ala Lys Asp Arg Pro Val Gly Asp Ala Met Asp Leu Glu
        35                  40                  45

Asp Ile Thr Pro Phe Met Gly Gln Thr Asp Ile His Pro Ala Asp Tyr
    50                  55                  60

Ser Asp Ala Lys Asp Ala Asp Val Cys Val Ile Ala Ala Gly Val Pro
65                  70                  75                  80

Arg Lys Pro Gly Glu Thr Arg Leu Asp Leu Val Ala Lys Asn Val Lys
                85                  90                  95

Ile Leu Lys Ser Ile Val Gln Pro Val Val Glu Ser Gly Phe Lys Gly
            100                 105                 110

Val Phe Val Val Ser Ala Asn Pro Val Asp Ile Leu Thr Thr Leu Thr
        115                 120                 125

Gln Lys Leu Ser Gly Phe Pro Lys Asn Arg Val Ile Gly Thr Gly Thr
    130                 135                 140

Ser Leu Asp Ser Met Arg Leu Arg Val Glu Leu Ala Lys Lys Leu Asn
145                 150                 155                 160

Val Pro Val Ala Lys Val Asn Ser Met Val Leu Gly Glu His Gly Asp
                165                 170                 175

Thr Ser Phe Glu Asn Phe Asp Glu Ser Thr Val Asp Gly Lys Pro Leu
            180                 185                 190

Arg Asp Tyr Ala Glu Ile Asn Asp Asp Val Leu Ser Glu Ile Glu Thr
        195                 200                 205

Asp Val Arg Lys Lys Gly Glu Lys Ile Ile Ala Lys Lys Gly Ala Thr
```

```
            210                 215                 220
Phe Tyr Gly Val Ala Met Met Leu Thr Gln Ile Val Ser Ala Ile Leu
225                 230                 235                 240

Asp Asn Arg Ser Ile Cys Leu Pro Leu Ser Ala Pro Ile Asn Gly Glu
                245                 250                 255

Tyr Gly Ile Lys His Asp Leu Tyr Leu Gly Thr Pro Ala Val Ile Asn
                    260                 265                 270

Gly Glu Gly Ile Glu Gln Val Ile Glu Thr Lys Leu Ser Asp Ala Glu
                275                 280                 285

Lys Ala Lys Met Ile Asn Ser Ala Asp Lys Met Gln Glu Val Leu Gly
            290                 295                 300

Gly Ile Glu
305

<210> SEQ ID NO 5
<211> LENGTH: 1002
<212> TYPE: DNA
<213> ORGANISM: Artificial
<220> FEATURE:
<223> OTHER INFORMATION: Synthetic construct (Bos taurus LDH variant)
<220> FEATURE:
<221> NAME/KEY: CDS
<222> LOCATION: (1)..(1002)

<400> SEQUENCE: 5 atg gcg act ctc aaa gat cag ctc ata cag aac ttg ctt aaa gaa gaa      48
Met Ala Thr Leu Lys Asp Gln Leu Ile Gln Asn Leu Leu Lys Glu Glu
1               5                   10                  15 cat gtg ccc cag aac aag atc acc atc gtg ggt gtg ggc gcc gtt ggg      96
His Val Pro Gln Asn Lys Ile Thr Ile Val Gly Val Gly Ala Val Gly
                20                  25                  30 atg gcc tgc gcg atc agc atc ctg atg aaa gat ctc gcc gac gaa gtc     144
Met Ala Cys Ala Ile Ser Ile Leu Met Lys Asp Leu Ala Asp Glu Val
            35                  40                  45 gca ctg gtt gac gtg atg gaa gat aag ctc aag ggt aat gaa atg atg     192
Ala Leu Val Asp Val Met Glu Asp Lys Leu Lys Gly Asn Glu Met Met
        50                  55                  60 gac ctc cag cat ggg tca ctg ttc ctg cga acc cca aag att gtc tcc     240
Asp Leu Gln His Gly Ser Leu Phe Leu Arg Thr Pro Lys Ile Val Ser
65                  70                  75                  80 gga aag gac tac aac gtc acc gcc aac agc cgg ctg gtg atc atc acg     288
Gly Lys Asp Tyr Asn Val Thr Ala Asn Ser Arg Leu Val Ile Ile Thr
                85                  90                  95 gct ggg gca cgc caa cag gaa ggc gag tcg agg ctg aac ctc gtc cag     336
Ala Gly Ala Arg Gln Gln Glu Gly Glu Ser Arg Leu Asn Leu Val Gln
            100                 105                 110 cgc aat gtc aac atc ttt aag ttc atc atc ccg aac atc gtg aag tac     384
Arg Asn Val Asn Ile Phe Lys Phe Ile Ile Pro Asn Ile Val Lys Tyr
        115                 120                 125 tcc ccg aac tgc aag ctg ttg gtt gtg tcg aat ccc gtg gat atc ctg     432
Ser Pro Asn Cys Lys Leu Leu Val Val Ser Asn Pro Val Asp Ile Leu
    130                 135                 140 acg tac gtc gcc tgg aag att tcg ggc ttc ccc aag aac cgg gta atc     480
Thr Tyr Val Ala Trp Lys Ile Ser Gly Phe Pro Lys Asn Arg Val Ile
145                 150                 155                 160 ggc agc ggc tgt aac ctg gat agc gcg cgt ttc cgc tac ctg atg ggc     528
Gly Ser Gly Cys Asn Leu Asp Ser Ala Arg Phe Arg Tyr Leu Met Gly
                165                 170                 175 gag cgc ttg gga gtc cac ccg ctg agc tgc cac ggg tgg atc ctc ggt     576
Glu Arg Leu Gly Val His Pro Leu Ser Cys His Gly Trp Ile Leu Gly
```

```
                    180                 185                 190
gag cat ggc gac tcc tcg gtg cct gtc tgg tct ggc gtc aat gta gcc        624
Glu His Gly Asp Ser Ser Val Pro Val Trp Ser Gly Val Asn Val Ala
        195                 200                 205 ggc gtc agt ctg aag aat ctg cac ccc gag ctg ggc acc gac gcc gac        672
Gly Val Ser Leu Lys Asn Leu His Pro Glu Leu Gly Thr Asp Ala Asp
    210                 215                 220 aaa gag cag tgg aaa gcc gtc cac aag caa gtg gtg gac tcg gcg tat        720
Lys Glu Gln Trp Lys Ala Val His Lys Gln Val Val Asp Ser Ala Tyr
225                 230                 235                 240 gaa gtc atc aag ctg aag ggc tat acc agt tgg gcg atc ggc ctg agc        768
Glu Val Ile Lys Leu Lys Gly Tyr Thr Ser Trp Ala Ile Gly Leu Ser
                245                 250                 255 gtg gcc gac ctg gcg gag tcc att atg aag aac ctt cgg cgc gtc cac        816
Val Ala Asp Leu Ala Glu Ser Ile Met Lys Asn Leu Arg Arg Val His
            260                 265                 270 ccg atc tcg acc atg atc aaa ggc ctc tac ggg atc aaa gaa gat gtg        864
Pro Ile Ser Thr Met Ile Lys Gly Leu Tyr Gly Ile Lys Glu Asp Val
        275                 280                 285 ttc ctc tcc gtc ccg tgc atc ttg ggc cag aac gga atc tcc gac gtc        912
Phe Leu Ser Val Pro Cys Ile Leu Gly Gln Asn Gly Ile Ser Asp Val
    290                 295                 300 gtg aag gtc aca ctg acg cat gaa gaa gaa gcg tgc ctg aag aag tcg        960
Val Lys Val Thr Leu Thr His Glu Glu Glu Ala Cys Leu Lys Lys Ser
305                 310                 315                 320 gcc gac acc ctg tgg ggc atc cag aaa gaa cta cag ttc taa                1002
Ala Asp Thr Leu Trp Gly Ile Gln Lys Glu Leu Gln Phe
                325                 330

<210> SEQ ID NO 6
<211> LENGTH: 333
<212> TYPE: PRT
<213> ORGANISM: Artificial
<220> FEATURE:
<223> OTHER INFORMATION: Synthetic Construct

<400> SEQUENCE: 6

Met Ala Thr Leu Lys Asp Gln Leu Ile Gln Asn Leu Leu Lys Glu Glu
1               5                   10                  15

His Val Pro Gln Asn Lys Ile Thr Ile Val Gly Val Gly Ala Val Gly
            20                  25                  30

Met Ala Cys Ala Ile Ser Ile Leu Met Lys Asp Leu Ala Asp Glu Val
        35                  40                  45

Ala Leu Val Asp Val Met Glu Asp Lys Leu Lys Gly Asn Glu Met Met
    50                  55                  60

Asp Leu Gln His Gly Ser Leu Phe Leu Arg Thr Pro Lys Ile Val Ser
65                  70                  75                  80

Gly Lys Asp Tyr Asn Val Thr Ala Asn Ser Arg Leu Val Ile Ile Thr
                85                  90                  95

Ala Gly Ala Arg Gln Gln Glu Gly Glu Ser Arg Leu Asn Leu Val Gln
            100                 105                 110

Arg Asn Val Asn Ile Phe Lys Phe Ile Ile Pro Asn Ile Val Lys Tyr
        115                 120                 125

Ser Pro Asn Cys Lys Leu Leu Val Val Ser Asn Pro Val Asp Ile Leu
    130                 135                 140

Thr Tyr Val Ala Trp Lys Ile Ser Gly Phe Pro Lys Asn Arg Val Ile
145                 150                 155                 160

Gly Ser Gly Cys Asn Leu Asp Ser Ala Arg Phe Arg Tyr Leu Met Gly
```

```
                165                 170                 175
Glu Arg Leu Gly Val His Pro Leu Ser Cys His Gly Trp Ile Leu Gly
            180                 185                 190

Glu His Gly Asp Ser Ser Val Pro Val Trp Ser Gly Val Asn Val Ala
        195                 200                 205

Gly Val Ser Leu Lys Asn Leu His Pro Glu Leu Gly Thr Asp Ala Asp
    210                 215                 220

Lys Glu Gln Trp Lys Ala Val His Lys Gln Val Val Asp Ser Ala Tyr
225                 230                 235                 240

Glu Val Ile Lys Leu Lys Gly Tyr Thr Ser Trp Ala Ile Gly Leu Ser
                245                 250                 255

Val Ala Asp Leu Ala Glu Ser Ile Met Lys Asn Leu Arg Arg Val His
            260                 265                 270

Pro Ile Ser Thr Met Ile Lys Gly Leu Tyr Gly Ile Lys Glu Asp Val
        275                 280                 285

Phe Leu Ser Val Pro Cys Ile Leu Gly Gln Asn Gly Ile Ser Asp Val
    290                 295                 300

Val Lys Val Thr Leu Thr His Glu Glu Glu Ala Cys Leu Lys Lys Ser
305                 310                 315                 320

Ala Asp Thr Leu Trp Gly Ile Gln Lys Glu Leu Gln Phe
                325                 330

<210> SEQ ID NO 7
<211> LENGTH: 260
<212> TYPE: DNA
<213> ORGANISM: Artificial
<220> FEATURE:
<223> OTHER INFORMATION: Synthetic construct (Pediococcus acidilactici
      LDH)
<220> FEATURE:
<221> NAME/KEY: CDS
<222> LOCATION: (1)..(258)

<400> SEQUENCE: 7 atg tct aat att caa aat cat caa aaa gtt gtc ctc gtc ggt gac ggt      48
Met Ser Asn Ile Gln Asn His Gln Lys Val Val Leu Val Gly Asp Gly
1               5                   10                  15 gcc gta ggt tct agt tac gca ttc gcg atg gca caa caa gga atc gct      96
Ala Val Gly Ser Ser Tyr Ala Phe Ala Met Ala Gln Gln Gly Ile Ala
                20                  25                  30 gaa gaa ttc gtc att gtc gac gtt gtt aag gat cgt aca gtt ggg gac     144
Glu Glu Phe Val Ile Val Asp Val Val Lys Asp Arg Thr Val Gly Asp
            35                  40                  45 gca ttg gac ctt gaa gat gct act cca ttc aca gct cca aag aac atc     192
Ala Leu Asp Leu Glu Asp Ala Thr Pro Phe Thr Ala Pro Lys Asn Ile
        50                  55                  60 tac tct ggt gaa tac tca gac tgc aag gat gct gac tta gtt gtt atc     240
Tyr Ser Gly Glu Tyr Ser Asp Cys Lys Asp Ala Asp Leu Val Val Ile
65                  70                  75                  80 aca gct ggc gca cca caa aa                                          260
Thr Ala Gly Ala Pro Gln
                85

<210> SEQ ID NO 8
<211> LENGTH: 86
<212> TYPE: PRT
<213> ORGANISM: Artificial
<220> FEATURE:
<223> OTHER INFORMATION: Synthetic Construct

<400> SEQUENCE: 8
```

```
Met Ser Asn Ile Gln Asn His Gln Lys Val Val Leu Val Gly Asp Gly
1               5                   10                  15

Ala Val Gly Ser Ser Tyr Ala Phe Ala Met Ala Gln Gln Gly Ile Ala
                20                  25                  30

Glu Glu Phe Val Ile Val Asp Val Val Lys Asp Arg Thr Val Gly Asp
            35                  40                  45

Ala Leu Asp Leu Glu Asp Ala Thr Pro Phe Thr Ala Pro Lys Asn Ile
        50                  55                  60

Tyr Ser Gly Glu Tyr Ser Asp Cys Lys Asp Ala Asp Leu Val Val Ile
65                  70                  75                  80

Thr Ala Gly Ala Pro Gln
                85

<210> SEQ ID NO 9
<211> LENGTH: 963
<212> TYPE: DNA
<213> ORGANISM: Artificial
<220> FEATURE:
<223> OTHER INFORMATION: Synthetic construct (Rhizopus oryzae LDH)
<220> FEATURE:
<221> NAME/KEY: CDS
<222> LOCATION: (1)..(963)

<400> SEQUENCE: 9 atg gta tta cac agc aaa gtc gca ata gtc gga gcg gga gca gtt ggc        48
Met Val Leu His Ser Lys Val Ala Ile Val Gly Ala Gly Ala Val Gly
1               5                   10                  15 gca tct aca gca tac gcg ttg atg ttc aag aac atc tgc acg gaa att        96
Ala Ser Thr Ala Tyr Ala Leu Met Phe Lys Asn Ile Cys Thr Glu Ile
                20                  25                  30 atc gtg gtc gac gtg aac ccc gat atc gtg cag gcc cag gtg ctg gac       144
Ile Val Val Asp Val Asn Pro Asp Ile Val Gln Ala Gln Val Leu Asp
            35                  40                  45 ctg gcc gat gcc gct agc atc tcc cac act cct atc agg gcg gga tcg       192
Leu Ala Asp Ala Ala Ser Ile Ser His Thr Pro Ile Arg Ala Gly Ser
        50                  55                  60 gtc gaa gaa gcc ggg cag gcc gat atc gtt gtg ata acc gcg ggt gcc       240
Val Glu Glu Ala Gly Gln Ala Asp Ile Val Val Ile Thr Ala Gly Ala
65                  70                  75                  80 aag cag cgc gag ggc gag ccg cgc acc aag ctg atc gaa cgg aat tac       288
Lys Gln Arg Glu Gly Glu Pro Arg Thr Lys Leu Ile Glu Arg Asn Tyr
                85                  90                  95 cgg gtc ctg cag agc atc atc ggc ggc atg cag ccc atc cgt cca gac       336
Arg Val Leu Gln Ser Ile Ile Gly Gly Met Gln Pro Ile Arg Pro Asp
            100                 105                 110 gcc gtg atc ctc gtg gtc gct aac ccg gtc gac att ctg acc cat atc       384
Ala Val Ile Leu Val Val Ala Asn Pro Val Asp Ile Leu Thr His Ile
        115                 120                 125 gct aag acc ctc tcc ggc ctg ccg ccc aac caa gtg atc ggc tcg ggt       432
Ala Lys Thr Leu Ser Gly Leu Pro Pro Asn Gln Val Ile Gly Ser Gly
    130                 135                 140 acc tac ctg gac acg acg cgc ctg cgc gtg cac ctc ggc gac gtg ttc       480
Thr Tyr Leu Asp Thr Thr Arg Leu Arg Val His Leu Gly Asp Val Phe
145                 150                 155                 160 gac gtc aac ccg cag agc atc cac gcg ttc gtg ctg ggc gag cac ggc       528
Asp Val Asn Pro Gln Ser Ile His Ala Phe Val Leu Gly Glu His Gly
                165                 170                 175 gac tcg caa atg atc gcg tgg gaa gcc gcg tcg atc ggc ggt cag ccc       576
Asp Ser Gln Met Ile Ala Trp Glu Ala Ala Ser Ile Gly Gly Gln Pro
            180                 185                 190
```

```
ctc acg agc ttc ccg gag ttc gcg aag ctg gac aag acc gcc atc tca    624
Leu Thr Ser Phe Pro Glu Phe Ala Lys Leu Asp Lys Thr Ala Ile Ser
        195                 200                 205 aag gcc atc tcc ggc aag gcc atg gaa atc att cgg ttg aaa ggc gcc    672
Lys Ala Ile Ser Gly Lys Ala Met Glu Ile Ile Arg Leu Lys Gly Ala
    210                 215                 220 acc ttc tac ggg atc ggg gcg tgt gcc gcc gat ctg gtg cat acc atc    720
Thr Phe Tyr Gly Ile Gly Ala Cys Ala Ala Asp Leu Val His Thr Ile
225                 230                 235                 240 atg ctg aac cgt aag agt gtc cat ccg gtg agt gtg tac gtc gag aaa    768
Met Leu Asn Arg Lys Ser Val His Pro Val Ser Val Tyr Val Glu Lys
            245                 250                 255 tat ggt gcg acg ttc tcc atg cct gcg aag ctg ggc tgg cgc ggc gta    816
Tyr Gly Ala Thr Phe Ser Met Pro Ala Lys Leu Gly Trp Arg Gly Val
                260                 265                 270 gag caa atc tat gaa gtc ccc ttg acc gaa gaa gaa gaa gcc ctt ctg    864
Glu Gln Ile Tyr Glu Val Pro Leu Thr Glu Glu Glu Glu Ala Leu Leu
            275                 280                 285 gtc aaa tcg gtc gag gcc ctc aag agc gtc gag tat tcc agt acc aag    912
Val Lys Ser Val Glu Ala Leu Lys Ser Val Glu Tyr Ser Ser Thr Lys
    290                 295                 300 gtg ccc gag aaa aaa gtc cat gcg acc tcg ttt agc aag tcc aat tgc    960
Val Pro Glu Lys Lys Val His Ala Thr Ser Phe Ser Lys Ser Asn Cys
305                 310                 315                 320 taa                                                                963
```

<210> SEQ ID NO 10
<211> LENGTH: 320
<212> TYPE: PRT
<213> ORGANISM: Artificial
<220> FEATURE:
<223> OTHER INFORMATION: Synthetic Construct

<400> SEQUENCE: 10

```
Met Val Leu His Ser Lys Val Ala Ile Val Gly Ala Gly Ala Val Gly
1               5                   10                  15

Ala Ser Thr Ala Tyr Ala Leu Met Phe Lys Asn Ile Cys Thr Glu Ile
            20                  25                  30

Ile Val Val Asp Val Asn Pro Asp Ile Val Gln Ala Gln Val Leu Asp
        35                  40                  45

Leu Ala Asp Ala Ala Ser Ile Ser His Thr Pro Ile Arg Ala Gly Ser
    50                  55                  60

Val Glu Glu Ala Gly Gln Ala Asp Ile Val Ile Thr Ala Gly Ala
65                  70                  75                  80

Lys Gln Arg Glu Gly Glu Pro Arg Thr Lys Leu Ile Glu Arg Asn Tyr
                85                  90                  95

Arg Val Leu Gln Ser Ile Ile Gly Gly Met Gln Pro Ile Arg Pro Asp
            100                 105                 110

Ala Val Ile Leu Val Val Ala Asn Pro Val Asp Ile Leu Thr His Ile
        115                 120                 125

Ala Lys Thr Leu Ser Gly Leu Pro Pro Asn Gln Val Ile Gly Ser Gly
    130                 135                 140

Thr Tyr Leu Asp Thr Thr Arg Leu Arg Val His Leu Gly Asp Val Phe
145                 150                 155                 160

Asp Val Asn Pro Gln Ser Ile His Ala Phe Val Leu Gly Glu His Gly
                165                 170                 175

Asp Ser Gln Met Ile Ala Trp Glu Ala Ala Ser Ile Gly Gly Gln Pro
```

```
                180             185                 190
Leu Thr Ser Phe Pro Glu Phe Ala Lys Leu Asp Lys Thr Ala Ile Ser
            195                 200                 205

Lys Ala Ile Ser Gly Lys Ala Met Glu Ile Ile Arg Leu Lys Gly Ala
            210                 215                 220

Thr Phe Tyr Gly Ile Gly Ala Cys Ala Ala Asp Leu Val His Thr Ile
225                 230                 235                 240

Met Leu Asn Arg Lys Ser Val His Pro Val Ser Val Tyr Val Glu Lys
                245                 250                 255

Tyr Gly Ala Thr Phe Ser Met Pro Ala Lys Leu Gly Trp Arg Gly Val
            260                 265                 270

Glu Gln Ile Tyr Glu Val Pro Leu Thr Glu Glu Glu Ala Leu Leu
            275                 280                 285

Val Lys Ser Val Glu Ala Leu Lys Ser Val Glu Tyr Ser Ser Thr Lys
            290                 295                 300

Val Pro Glu Lys Lys Val His Ala Thr Ser Phe Ser Lys Ser Asn Cys
305                 310                 315                 320
```

<210> SEQ ID NO 11
<211> LENGTH: 984
<212> TYPE: DNA
<213> ORGANISM: Artificial
<220> FEATURE:
<223> OTHER INFORMATION: Synthetic construct (Enterococcus faecalis LDH)
<220> FEATURE:
<221> NAME/KEY: CDS
<222> LOCATION: (1)..(984)

<400> SEQUENCE: 11

```
atg acc gcg gct gcc gga aat aag gac cac cag aaa gtg ata ctg gtc      48
Met Thr Ala Ala Ala Gly Asn Lys Asp His Gln Lys Val Ile Leu Val
1               5                   10                  15 ggg gac ggt gcc gtg ggc agc tcg tat gca ttc gcg ttg gtg acc cag      96
Gly Asp Gly Ala Val Gly Ser Ser Tyr Ala Phe Ala Leu Val Thr Gln
            20                  25                  30 aac atc gcc caa gaa gtc ggc atc ata gat atc aac gtc ccc aag acc     144
Asn Ile Ala Gln Glu Val Gly Ile Ile Asp Ile Asn Val Pro Lys Thr
        35                  40                  45 gag ggc gac gcc ctg gat ctc tcc cac gcc ctg gcc ttc acc agc ccc     192
Glu Gly Asp Ala Leu Asp Leu Ser His Ala Leu Ala Phe Thr Ser Pro
    50                  55                  60 aaa aag atc tac gcg gcc acc tac gac gat tgc cat gac gcg gat ctc     240
Lys Lys Ile Tyr Ala Ala Thr Tyr Asp Asp Cys His Asp Ala Asp Leu
65                  70                  75                  80 gtt gtc ctg acc gcg ggt gcg ccg cag aag cct ggc gaa acg cga ctg     288
Val Val Leu Thr Ala Gly Ala Pro Gln Lys Pro Gly Glu Thr Arg Leu
                85                  90                  95 gat ctc gtc cat aag aac ttg aag atc aac aaa gaa atc gtc acc acc     336
Asp Leu Val His Lys Asn Leu Lys Ile Asn Lys Glu Ile Val Thr Thr
            100                 105                 110 atc gtg gac tcg ggc ttc aac ggc atc ttc ctg gtg gcg gcc aac cca     384
Ile Val Asp Ser Gly Phe Asn Gly Ile Phe Leu Val Ala Ala Asn Pro
        115                 120                 125 gta gac atc ctg acc tac tca acg tgg aag ttt agc ggg ttc ccg aag     432
Val Asp Ile Leu Thr Tyr Ser Thr Trp Lys Phe Ser Gly Phe Pro Lys
    130                 135                 140 gaa cgg gtc atc ggg tcc ggc aca tcg ctt gac tcc gcg cgg ttc cgc     480
Glu Arg Val Ile Gly Ser Gly Thr Ser Leu Asp Ser Ala Arg Phe Arg
145                 150                 155                 160
```

```
cag gcc att gcg gag ctg gtc gac gtg gac gcc cgc aac gtg cac gcg     528
Gln Ala Ile Ala Glu Leu Val Asp Val Asp Ala Arg Asn Val His Ala
                165                 170                 175 tat atc ctc ggc gag cat ggc gac acc gag ttt ccc gtt tgg tcc cac     576
Tyr Ile Leu Gly Glu His Gly Asp Thr Glu Phe Pro Val Trp Ser His
            180                 185                 190 gcc aat gtg gcg gga ttg cag atc tac gag tgg gta aag aat aat ccc     624
Ala Asn Val Ala Gly Leu Gln Ile Tyr Glu Trp Val Lys Asn Asn Pro
        195                 200                 205 gat gtc gac gaa gaa gcc atg gtc aac ctc ttc ttc aac gtg cgc gat     672
Asp Val Asp Glu Glu Ala Met Val Asn Leu Phe Phe Asn Val Arg Asp
    210                 215                 220 gca gct tat acg atc atc gag aaa aag gga gcc acg ttc tat ggc atc     720
Ala Ala Tyr Thr Ile Ile Glu Lys Lys Gly Ala Thr Phe Tyr Gly Ile
225                 230                 235                 240 gcc gtg gcg ctg gcc cgg atc acg aag gcc atc ctg aac gac gag aat     768
Ala Val Ala Leu Ala Arg Ile Thr Lys Ala Ile Leu Asn Asp Glu Asn
                245                 250                 255 tcc gtg ctc ccg ctg agt gtc tac ctg gaa ggg gag tac ggt cag aac     816
Ser Val Leu Pro Leu Ser Val Tyr Leu Glu Gly Glu Tyr Gly Gln Asn
            260                 265                 270 gac atc tac atc ggc gca ccg gcc atc att aac cgt cag ggc gtc aaa     864
Asp Ile Tyr Ile Gly Ala Pro Ala Ile Ile Asn Arg Gln Gly Val Lys
        275                 280                 285 caa gtg att gaa atc ccg ctg acc gac gcc gag caa gag aag atg gaa     912
Gln Val Ile Glu Ile Pro Leu Thr Asp Ala Glu Gln Glu Lys Met Glu
    290                 295                 300 gcc agc gct tcg gcg ctg aaa gaa gtc atc gag act gcc ttc gcc aag     960
Ala Ser Ala Ser Ala Leu Lys Glu Val Ile Glu Thr Ala Phe Ala Lys
305                 310                 315                 320 ttc gag gcc gaa gaa gcg aag taa                                     984
Phe Glu Ala Glu Glu Ala Lys
                325

<210> SEQ ID NO 12
<211> LENGTH: 327
<212> TYPE: PRT
<213> ORGANISM: Artificial
<220> FEATURE:
<223> OTHER INFORMATION: Synthetic Construct

<400> SEQUENCE: 12

Met Thr Ala Ala Ala Gly Asn Lys Asp His Gln Lys Val Ile Leu Val
1               5                   10                  15

Gly Asp Gly Ala Val Gly Ser Ser Tyr Ala Phe Ala Leu Val Thr Gln
            20                  25                  30

Asn Ile Ala Gln Glu Val Gly Ile Ile Asp Ile Asn Val Pro Lys Thr
        35                  40                  45

Glu Gly Asp Ala Leu Asp Leu Ser His Ala Leu Ala Phe Thr Ser Pro
    50                  55                  60

Lys Lys Ile Tyr Ala Ala Thr Tyr Asp Asp Cys His Asp Ala Asp Leu
65                  70                  75                  80

Val Val Leu Thr Ala Gly Ala Pro Gln Lys Pro Gly Glu Thr Arg Leu
                85                  90                  95

Asp Leu Val His Lys Asn Leu Lys Ile Asn Lys Glu Ile Val Thr Thr
            100                 105                 110

Ile Val Asp Ser Gly Phe Asn Gly Ile Phe Leu Val Ala Ala Asn Pro
        115                 120                 125

Val Asp Ile Leu Thr Tyr Ser Thr Trp Lys Phe Ser Gly Phe Pro Lys
```

-continued

```
             130                 135                 140
Glu Arg Val Ile Gly Ser Gly Thr Ser Leu Asp Ser Ala Arg Phe Arg
145                 150                 155                 160

Gln Ala Ile Ala Glu Leu Val Asp Val Asp Ala Arg Asn Val His Ala
                165                 170                 175

Tyr Ile Leu Gly Glu His Gly Asp Thr Glu Phe Pro Val Trp Ser His
                180                 185                 190

Ala Asn Val Ala Gly Leu Gln Ile Tyr Glu Trp Val Lys Asn Asn Pro
                195                 200                 205

Asp Val Asp Glu Glu Ala Met Val Asn Leu Phe Phe Asn Val Arg Asp
                210                 215                 220

Ala Ala Tyr Thr Ile Ile Glu Lys Lys Gly Ala Thr Phe Tyr Gly Ile
225                 230                 235                 240

Ala Val Ala Leu Ala Arg Ile Thr Lys Ala Ile Leu Asn Asp Glu Asn
                245                 250                 255

Ser Val Leu Pro Leu Ser Val Tyr Leu Glu Gly Glu Tyr Gly Gln Asn
                260                 265                 270

Asp Ile Tyr Ile Gly Ala Pro Ala Ile Ile Asn Arg Gln Gly Val Lys
                275                 280                 285

Gln Val Ile Glu Ile Pro Leu Thr Asp Ala Glu Gln Glu Lys Met Glu
                290                 295                 300

Ala Ser Ala Ser Ala Leu Lys Glu Val Ile Glu Thr Ala Phe Ala Lys
305                 310                 315                 320

Phe Glu Ala Glu Glu Ala Lys
                325
```

<210> SEQ ID NO 13
<211> LENGTH: 939
<212> TYPE: DNA
<213> ORGANISM: Artificial
<220> FEATURE:
<223> OTHER INFORMATION: Synthetic construct (Lactobacillus casei LDH)
<220> FEATURE:
<221> NAME/KEY: CDS
<222> LOCATION: (1)..(939)

<400> SEQUENCE: 13

```
atg cgc aat aac ggg aac atc att ctt ata ggt gac ggt gcc atc ggt      48
Met Arg Asn Asn Gly Asn Ile Ile Leu Ile Gly Asp Gly Ala Ile Gly
1               5                  10                  15 agt tct tat gcc ttc aac tgc ctg acc acc ggc gtc ggc cag tcc ctg      96
Ser Ser Tyr Ala Phe Asn Cys Leu Thr Thr Gly Val Gly Gln Ser Leu
            20                  25                  30 ggg ata atc gac gtg aac gag aag cgc gta cag ggc gac gtc gag gac     144
Gly Ile Ile Asp Val Asn Glu Lys Arg Val Gln Gly Asp Val Glu Asp
        35                  40                  45 ttg agc gac gcc ctg ccc tac act tcg cag aag aac atc tac gct gcg     192
Leu Ser Asp Ala Leu Pro Tyr Thr Ser Gln Lys Asn Ile Tyr Ala Ala
    50                  55                  60 tcc tac gaa gat tgc aaa tat gcc gac att atc gtg atc acg gca ggc     240
Ser Tyr Glu Asp Cys Lys Tyr Ala Asp Ile Ile Val Ile Thr Ala Gly
65                  70                  75                  80 atc gcc cag aag ccc gga cag acc cgg ttg cag ctc ctg gca atc aac     288
Ile Ala Gln Lys Pro Gly Gln Thr Arg Leu Gln Leu Leu Ala Ile Asn
                85                  90                  95 gcg aag att atg aaa gaa atc acc cat aac atc atg gcc tcg ggt ttc     336
Ala Lys Ile Met Lys Glu Ile Thr His Asn Ile Met Ala Ser Gly Phe
            100                 105                 110
```

```
aat ggc ttc atc ctg gtc gcc agc aac ccg gtg gac gtc ttg gcg gag    384
Asn Gly Phe Ile Leu Val Ala Ser Asn Pro Val Asp Val Leu Ala Glu
        115                 120                 125 ctg gtg ctc cag gaa tcg ggc ctg ccc cgg aac caa gtc ctg ggc tcg    432
Leu Val Leu Gln Glu Ser Gly Leu Pro Arg Asn Gln Val Leu Gly Ser
130                 135                 140 ggc acc gcc ctc gac tcg gcg cgt ctg cgg agc gag atc ggg ctg cgc    480
Gly Thr Ala Leu Asp Ser Ala Arg Leu Arg Ser Glu Ile Gly Leu Arg
    145                 150                 155                 160 tac aat gtc gac gca cgg atc gtc cac ggg tac atc atg ggc gag cac    528
Tyr Asn Val Asp Ala Arg Ile Val His Gly Tyr Ile Met Gly Glu His
                165                 170                 175 ggc gat tcc gag ttc ccg gtg tgg gac tac acc aat atc ggc ggc aag    576
Gly Asp Ser Glu Phe Pro Val Trp Asp Tyr Thr Asn Ile Gly Gly Lys
            180                 185                 190 ccg atc ctc gat tgg atc ccg aag gac cgc cag gac aaa gat ctc cct    624
Pro Ile Leu Asp Trp Ile Pro Lys Asp Arg Gln Asp Lys Asp Leu Pro
        195                 200                 205 gat atc tcc gaa agg gtt aag aca gcg gcc tat gga att atc gag aag    672
Asp Ile Ser Glu Arg Val Lys Thr Ala Ala Tyr Gly Ile Ile Glu Lys
    210                 215                 220 aaa ggg gcc acg ttt tac ggc atc gcc gcg tcc ctg acc cgt ttg acg    720
Lys Gly Ala Thr Phe Tyr Gly Ile Ala Ala Ser Leu Thr Arg Leu Thr
225                 230                 235                 240 tca gcg ttc ctg aac gac gat cga gcg gcc ttc gcc atg agc gtg cat    768
Ser Ala Phe Leu Asn Asp Asp Arg Ala Ala Phe Ala Met Ser Val His
                245                 250                 255 ctg gaa ggc gaa tat ggc ctt agc gga gtg tcg atc ggc gtc ccg gtg    816
Leu Glu Gly Glu Tyr Gly Leu Ser Gly Val Ser Ile Gly Val Pro Val
            260                 265                 270 atc ctg ggc gcc aac ggc ctg gag cgc atc atc gaa ctc gac ctg aat    864
Ile Leu Gly Ala Asn Gly Leu Glu Arg Ile Ile Glu Leu Asp Leu Asn
        275                 280                 285 cca gag gat cac aag cgc ctg gcc gac agc gct gcg atc ctc aag gaa    912
Pro Glu Asp His Lys Arg Leu Ala Asp Ser Ala Ala Ile Leu Lys Glu
    290                 295                 300 aac ctg aaa aag gcg caa gaa gcc taa                                 939
Asn Leu Lys Lys Ala Gln Glu Ala
305                 310

<210> SEQ ID NO 14
<211> LENGTH: 312
<212> TYPE: PRT
<213> ORGANISM: Artificial
<220> FEATURE:
<223> OTHER INFORMATION: Synthetic Construct

<400> SEQUENCE: 14

Met Arg Asn Asn Gly Asn Ile Ile Leu Ile Gly Asp Gly Ala Ile Gly
1               5                   10                  15

Ser Ser Tyr Ala Phe Asn Cys Leu Thr Thr Gly Val Gly Gln Ser Leu
            20                  25                  30

Gly Ile Ile Asp Val Asn Glu Lys Arg Val Gln Gly Asp Val Glu Asp
        35                  40                  45

Leu Ser Asp Ala Leu Pro Tyr Thr Ser Gln Lys Asn Ile Tyr Ala Ala
    50                  55                  60

Ser Tyr Glu Asp Cys Lys Tyr Ala Asp Ile Val Ile Thr Ala Gly
65                  70                  75                  80

Ile Ala Gln Lys Pro Gly Gln Thr Arg Leu Gln Leu Leu Ala Ile Asn
                85                  90                  95
```

```
Ala Lys Ile Met Lys Glu Ile Thr His Asn Ile Met Ala Ser Gly Phe
            100                 105                 110

Asn Gly Phe Ile Leu Val Ala Ser Asn Pro Val Asp Val Leu Ala Glu
            115                 120                 125

Leu Val Leu Gln Glu Ser Gly Leu Pro Arg Asn Gln Val Leu Gly Ser
            130                 135                 140

Gly Thr Ala Leu Asp Ser Ala Arg Leu Arg Ser Glu Ile Gly Leu Arg
145                 150                 155                 160

Tyr Asn Val Asp Ala Arg Ile Val His Gly Tyr Ile Met Gly Glu His
                165                 170                 175

Gly Asp Ser Glu Phe Pro Val Trp Asp Tyr Thr Asn Ile Gly Gly Lys
            180                 185                 190

Pro Ile Leu Asp Trp Ile Pro Lys Asp Arg Gln Asp Lys Asp Leu Pro
            195                 200                 205

Asp Ile Ser Glu Arg Val Lys Thr Ala Ala Tyr Gly Ile Ile Glu Lys
            210                 215                 220

Lys Gly Ala Thr Phe Tyr Gly Ile Ala Ala Ser Leu Thr Arg Leu Thr
225                 230                 235                 240

Ser Ala Phe Leu Asn Asp Asp Arg Ala Ala Phe Ala Met Ser Val His
                245                 250                 255

Leu Glu Gly Glu Tyr Gly Leu Ser Gly Val Ser Ile Gly Val Pro Val
            260                 265                 270

Ile Leu Gly Ala Asn Gly Leu Glu Arg Ile Ile Glu Leu Asp Leu Asn
            275                 280                 285

Pro Glu Asp His Lys Arg Leu Ala Asp Ser Ala Ala Ile Leu Lys Glu
            290                 295                 300

Asn Leu Lys Lys Ala Gln Glu Ala
305                 310

<210> SEQ ID NO 15
<211> LENGTH: 957
<212> TYPE: DNA
<213> ORGANISM: Artificial
<220> FEATURE:
<223> OTHER INFORMATION: Synthetic construct (Bacillus megaterium LDH)
<220> FEATURE:
<221> NAME/KEY: CDS
<222> LOCATION: (1)..(957)

<400> SEQUENCE: 15 atg aaa acg cag ttc acc ccc aag aca cga aaa gta gca gtt ata ggc     48
Met Lys Thr Gln Phe Thr Pro Lys Thr Arg Lys Val Ala Val Ile Gly
1               5                   10                  15 acc ggc ttc gtg ggc tcc tcc tac gcg ttc tcg atg gtc aat cag ggg    96
Thr Gly Phe Val Gly Ser Ser Tyr Ala Phe Ser Met Val Asn Gln Gly
                20                  25                  30 atc gcg aac gaa ctg gtc ctg atc gac atg aac aag gaa aag gcc gag   144
Ile Ala Asn Glu Leu Val Leu Ile Asp Met Asn Lys Glu Lys Ala Glu
            35                  40                  45 ggc gaa gcc cgg gat atc aac cat ggc atg cct ttt gcc acc ccg atg   192
Gly Glu Ala Arg Asp Ile Asn His Gly Met Pro Phe Ala Thr Pro Met
        50                  55                  60 aag att tgg gcc gga gat tac aag gac tgc gcg gac gcg gac ctg gcc   240
Lys Ile Trp Ala Gly Asp Tyr Lys Asp Cys Ala Asp Ala Asp Leu Ala
65                  70                  75                  80 gtg atc acc gcg ggt gcg aat cag gct ccg ggt gaa acc cgg ctg gac   288
Val Ile Thr Ala Gly Ala Asn Gln Ala Pro Gly Glu Thr Arg Leu Asp
                85                  90                  95
```

```
ctc gtc gag aaa aat gtc aag atc ttc gag tgc atc gtt aaa gac atc      336
Leu Val Glu Lys Asn Val Lys Ile Phe Glu Cys Ile Val Lys Asp Ile
            100                 105                 110 atg aac tcg ggg ttc gac ggc atc atc ctg gtc gcc acc aac ccg gtc      384
Met Asn Ser Gly Phe Asp Gly Ile Ile Leu Val Ala Thr Asn Pro Val
        115                 120                 125 gat atc ctg gcc cat gtc acg caa aag gtg agc ggc ctg ccc aac gag      432
Asp Ile Leu Ala His Val Thr Gln Lys Val Ser Gly Leu Pro Asn Glu
130                 135                 140 cgg gtc att ggt tcg ggc acc atc ttg gac acg gcc cgt ttc cgc tat      480
Arg Val Ile Gly Ser Gly Thr Ile Leu Asp Thr Ala Arg Phe Arg Tyr
145                 150                 155                 160 ctc ttg agc gat tac ttc gaa gtg gat tcc cgc aac gtc cac gcg tac      528
Leu Leu Ser Asp Tyr Phe Glu Val Asp Ser Arg Asn Val His Ala Tyr
                165                 170                 175 atc atg ggc gag cac ggg gac acg gaa ttc ccg gtc tgg tcg cac gcc      576
Ile Met Gly Glu His Gly Asp Thr Glu Phe Pro Val Trp Ser His Ala
            180                 185                 190 cag atc ggc gga gtg aag ctg gag cac ttt atc aat acg gca gct atc      624
Gln Ile Gly Gly Val Lys Leu Glu His Phe Ile Asn Thr Ala Ala Ile
        195                 200                 205 gaa aaa gag cca gac atg cag cac ctg ttc gag cag acc cgg gac gcg      672
Glu Lys Glu Pro Asp Met Gln His Leu Phe Glu Gln Thr Arg Asp Ala
210                 215                 220 gcc tac cac atc att aat cgc aag ggc gcg acg tac tat gga atc gcc      720
Ala Tyr His Ile Ile Asn Arg Lys Gly Ala Thr Tyr Tyr Gly Ile Ala
225                 230                 235                 240 atg ggg ctg gtc agg atc acc aag gcc atc ctt gac gat gag aac agc      768
Met Gly Leu Val Arg Ile Thr Lys Ala Ile Leu Asp Asp Glu Asn Ser
                245                 250                 255 atc ctc acc gtg agt gcg ctg ttg gaa ggc cag tat ggc ata tca gac      816
Ile Leu Thr Val Ser Ala Leu Leu Glu Gly Gln Tyr Gly Ile Ser Asp
            260                 265                 270 gtg tat atc ggt gtg ccc gcc att atc aac aag aac ggc gtg cgg cag      864
Val Tyr Ile Gly Val Pro Ala Ile Ile Asn Lys Asn Gly Val Arg Gln
        275                 280                 285 atc atc gag ctg aac ctg acc ccg cat gaa caa cag cag ctc gaa cat      912
Ile Ile Glu Leu Asn Leu Thr Pro His Glu Gln Gln Gln Leu Glu His
290                 295                 300 agc gcc tcc atc ctc aag cag act cgc gat cgc gcc ttc gtg taa          957
Ser Ala Ser Ile Leu Lys Gln Thr Arg Asp Arg Ala Phe Val
305                 310                 315

<210> SEQ ID NO 16
<211> LENGTH: 318
<212> TYPE: PRT
<213> ORGANISM: Artificial
<220> FEATURE:
<223> OTHER INFORMATION: Synthetic Construct

<400> SEQUENCE: 16

Met Lys Thr Gln Phe Thr Pro Lys Thr Arg Lys Val Ala Val Ile Gly
1               5                   10                  15

Thr Gly Phe Val Gly Ser Ser Tyr Ala Phe Ser Met Val Asn Gln Gly
            20                  25                  30

Ile Ala Asn Glu Leu Val Leu Ile Asp Met Asn Lys Glu Lys Ala Glu
        35                  40                  45

Gly Glu Ala Arg Asp Ile Asn His Gly Met Pro Phe Ala Thr Pro Met
    50                  55                  60
```

```
Lys Ile Trp Ala Gly Asp Tyr Lys Asp Cys Ala Asp Ala Asp Leu Ala
 65                  70                  75                  80

Val Ile Thr Ala Gly Ala Asn Gln Ala Pro Gly Glu Thr Arg Leu Asp
                 85                  90                  95

Leu Val Glu Lys Asn Val Lys Ile Phe Glu Cys Ile Val Lys Asp Ile
            100                 105                 110

Met Asn Ser Gly Phe Asp Gly Ile Ile Leu Val Ala Thr Asn Pro Val
        115                 120                 125

Asp Ile Leu Ala His Val Thr Gln Lys Val Ser Gly Leu Pro Asn Glu
130                 135                 140

Arg Val Ile Gly Ser Gly Thr Ile Leu Asp Thr Ala Arg Phe Arg Tyr
145                 150                 155                 160

Leu Leu Ser Asp Tyr Phe Glu Val Asp Ser Arg Asn Val His Ala Tyr
                165                 170                 175

Ile Met Gly Glu His Gly Asp Thr Glu Phe Pro Val Trp Ser His Ala
            180                 185                 190

Gln Ile Gly Gly Val Lys Leu Glu His Phe Ile Asn Thr Ala Ala Ile
        195                 200                 205

Glu Lys Glu Pro Asp Met Gln His Leu Phe Glu Gln Thr Arg Asp Ala
210                 215                 220

Ala Tyr His Ile Ile Asn Arg Lys Gly Ala Thr Tyr Tyr Gly Ile Ala
225                 230                 235                 240

Met Gly Leu Val Arg Ile Thr Lys Ala Ile Leu Asp Asp Glu Asn Ser
                245                 250                 255

Ile Leu Thr Val Ser Ala Leu Leu Glu Gly Gln Tyr Gly Ile Ser Asp
            260                 265                 270

Val Tyr Ile Gly Val Pro Ala Ile Ile Asn Lys Asn Gly Val Arg Gln
        275                 280                 285

Ile Ile Glu Leu Asn Leu Thr Pro His Glu Gln Gln Gln Leu Glu His
290                 295                 300

Ser Ala Ser Ile Leu Lys Gln Thr Arg Asp Arg Ala Phe Val
305                 310                 315

<210> SEQ ID NO 17
<211> LENGTH: 957
<212> TYPE: DNA
<213> ORGANISM: Artificial
<220> FEATURE:
<223> OTHER INFORMATION: Synthetic construct (Taeniopygia guttata LDH)
<220> FEATURE:
<221> NAME/KEY: CDS
<222> LOCATION: (1)..(957)

<400> SEQUENCE: 17 atg aaa acg cag ttc acc ccc aag aca cga aaa gta gca gtt ata ggc      48
Met Lys Thr Gln Phe Thr Pro Lys Thr Arg Lys Val Ala Val Ile Gly
  1               5                  10                  15 acc ggc ttc gtg ggc tcc tcc tac gcg ttc tcg atg gtc aat cag ggg      96
Thr Gly Phe Val Gly Ser Ser Tyr Ala Phe Ser Met Val Asn Gln Gly
             20                  25                  30 atc gcg aac gaa ctg gtc ctg atc gac atg aac aag gaa aag gcc gag     144
Ile Ala Asn Glu Leu Val Leu Ile Asp Met Asn Lys Glu Lys Ala Glu
         35                  40                  45 ggc gaa gcc cgg gat atc aac cat ggc atg cct ttt gcc acc ccg atg     192
Gly Glu Ala Arg Asp Ile Asn His Gly Met Pro Phe Ala Thr Pro Met
     50                  55                  60 aag att tgg gcc gga gat tac aag gac tgc gcg gac gcg gac ctg gcc     240
Lys Ile Trp Ala Gly Asp Tyr Lys Asp Cys Ala Asp Ala Asp Leu Ala
```

```
                 65                  70                  75                  80
gtg atc acc gcg ggt gcg aat cag gct ccg ggt gaa acc cgg ctg gac       288
Val Ile Thr Ala Gly Ala Asn Gln Ala Pro Gly Glu Thr Arg Leu Asp
                 85                  90                  95 ctc gtc gag aaa aat gtc aag atc ttc gag tgc atc gtt aaa gac atc       336
Leu Val Glu Lys Asn Val Lys Ile Phe Glu Cys Ile Val Lys Asp Ile
            100                 105                 110 atg aac tcg ggg ttc gac ggc atc atc ctg gtc gcc acc aac ccg gtc       384
Met Asn Ser Gly Phe Asp Gly Ile Ile Leu Val Ala Thr Asn Pro Val
        115                 120                 125 gat atc ctg gcc cat gtc acg caa aag gtg agc ggc ctg ccc aac gag       432
Asp Ile Leu Ala His Val Thr Gln Lys Val Ser Gly Leu Pro Asn Glu
    130                 135                 140 cgg gtc att ggt tcg ggc acc atc ttg gac acg gcc cgt ttc cgc tat       480
Arg Val Ile Gly Ser Gly Thr Ile Leu Asp Thr Ala Arg Phe Arg Tyr
145                 150                 155                 160 ctc ttg agc gat tac ttc gaa gtg gat tcc cgc aac gtc cac gcg tac       528
Leu Leu Ser Asp Tyr Phe Glu Val Asp Ser Arg Asn Val His Ala Tyr
                165                 170                 175 atc atg ggc gag cac ggg gac acg gaa ttc ccg gtc tgg tcg cac gcc       576
Ile Met Gly Glu His Gly Asp Thr Glu Phe Pro Val Trp Ser His Ala
            180                 185                 190 cag atc ggc gga gtg aag ctg gag cac ttt atc aat acg gca gct atc       624
Gln Ile Gly Gly Val Lys Leu Glu His Phe Ile Asn Thr Ala Ala Ile
        195                 200                 205 gaa aaa gag cca gac atg cag cac ctg ttc gag cag acc cgg gac gcg       672
Glu Lys Glu Pro Asp Met Gln His Leu Phe Glu Gln Thr Arg Asp Ala
    210                 215                 220 gcc tac cac atc att aat cgc aag ggc gcg acg tac tat gga atc gcc       720
Ala Tyr His Ile Ile Asn Arg Lys Gly Ala Thr Tyr Tyr Gly Ile Ala
225                 230                 235                 240 atg ggg ctg gtc agg atc acc aag gcc atc ctt gac gat gag aac agc       768
Met Gly Leu Val Arg Ile Thr Lys Ala Ile Leu Asp Asp Glu Asn Ser
                245                 250                 255 atc ctc acc gtg agt gcg ctg ttg gaa ggc cag tat ggc ata tca gac       816
Ile Leu Thr Val Ser Ala Leu Leu Glu Gly Gln Tyr Gly Ile Ser Asp
            260                 265                 270 gtg tat atc ggt gtg ccc gcc att atc aac aag aac ggc gtg cgg cag       864
Val Tyr Ile Gly Val Pro Ala Ile Ile Asn Lys Asn Gly Val Arg Gln
        275                 280                 285 atc atc gag ctg aac ctg acc ccg cat gaa caa cag cag ctc gaa cat       912
Ile Ile Glu Leu Asn Leu Thr Pro His Glu Gln Gln Gln Leu Glu His
    290                 295                 300 agc gcc tcc atc ctc aag cag act cgc gat cgc gcc ttc gtg taa           957
Ser Ala Ser Ile Leu Lys Gln Thr Arg Asp Arg Ala Phe Val
305                 310                 315

<210> SEQ ID NO 18
<211> LENGTH: 318
<212> TYPE: PRT
<213> ORGANISM: Artificial
<220> FEATURE:
<223> OTHER INFORMATION: Synthetic Construct

<400> SEQUENCE: 18

Met Lys Thr Gln Phe Thr Pro Lys Thr Arg Lys Val Ala Val Ile Gly
1               5                   10                  15

Thr Gly Phe Val Gly Ser Ser Tyr Ala Phe Ser Met Val Asn Gln Gly
            20                  25                  30

Ile Ala Asn Glu Leu Val Leu Ile Asp Met Asn Lys Glu Lys Ala Glu
```

```
                    35                  40                  45
Gly Glu Ala Arg Asp Ile Asn His Gly Met Pro Phe Ala Thr Pro Met
 50                  55                  60

Lys Ile Trp Ala Gly Asp Tyr Lys Asp Cys Ala Asp Ala Asp Leu Ala
 65                  70                  75                  80

Val Ile Thr Ala Gly Ala Asn Gln Ala Pro Gly Glu Thr Arg Leu Asp
                     85                  90                  95

Leu Val Glu Lys Asn Val Lys Ile Phe Glu Cys Ile Val Lys Asp Ile
                100                 105                 110

Met Asn Ser Gly Phe Asp Gly Ile Ile Leu Val Ala Thr Asn Pro Val
                115                 120                 125

Asp Ile Leu Ala His Val Thr Gln Lys Val Ser Gly Leu Pro Asn Glu
                130                 135                 140

Arg Val Ile Gly Ser Gly Thr Ile Leu Asp Thr Ala Arg Phe Arg Tyr
145                 150                 155                 160

Leu Leu Ser Asp Tyr Phe Glu Val Asp Ser Arg Asn Val His Ala Tyr
                165                 170                 175

Ile Met Gly Glu His Gly Asp Thr Glu Phe Pro Val Trp Ser His Ala
                180                 185                 190

Gln Ile Gly Gly Val Lys Leu Glu His Phe Ile Asn Thr Ala Ala Ile
                195                 200                 205

Glu Lys Glu Pro Asp Met Gln His Leu Phe Glu Gln Thr Arg Asp Ala
                210                 215                 220

Ala Tyr His Ile Ile Asn Arg Lys Gly Ala Thr Tyr Tyr Gly Ile Ala
225                 230                 235                 240

Met Gly Leu Val Arg Ile Thr Lys Ala Ile Leu Asp Asp Glu Asn Ser
                245                 250                 255

Ile Leu Thr Val Ser Ala Leu Leu Glu Gly Gln Tyr Gly Ile Ser Asp
                260                 265                 270

Val Tyr Ile Gly Val Pro Ala Ile Ile Asn Lys Asn Gly Val Arg Gln
                275                 280                 285

Ile Ile Glu Leu Asn Leu Thr Pro His Glu Gln Gln Gln Leu Glu His
                290                 295                 300

Ser Ala Ser Ile Leu Lys Gln Thr Arg Asp Arg Ala Phe Val
305                 310                 315
```

<210> SEQ ID NO 19
<211> LENGTH: 963
<212> TYPE: DNA
<213> ORGANISM: Artificial
<220> FEATURE:
<223> OTHER INFORMATION: Synthetic construct (Lactobacillus plantarum LDH)
<220> FEATURE:
<221> NAME/KEY: CDS
<222> LOCATION: (1)..(963)

<400> SEQUENCE: 19

```
atg tcg tcg atg cct aac cat cag aaa gtc gtc ctg gtg ggc gac gga      48
Met Ser Ser Met Pro Asn His Gln Lys Val Val Leu Val Gly Asp Gly
 1               5                  10                  15 gcg gtc ggc agc tca tac gcc ttc gcg atg gcg caa cag gga atc gcg      96
Ala Val Gly Ser Ser Tyr Ala Phe Ala Met Ala Gln Gln Gly Ile Ala
                 20                  25                  30 gaa gaa ttc gtc atc gtc gac gtg gtg aag gac cgc acc aag ggc gac     144
Glu Glu Phe Val Ile Val Asp Val Val Lys Asp Arg Thr Lys Gly Asp
             35                  40                  45
```

| gcc | ttg | gac | ctc | gaa | gat | gca | cag | gcc | ttc | acg | gcc | ccg | aag | aaa | atc | 192 |
| Ala | Leu | Asp | Leu | Glu | Asp | Ala | Gln | Ala | Phe | Thr | Ala | Pro | Lys | Lys | Ile | |
| | 50 | | | | 55 | | | | 60 | | | | | | | |

| tac | agc | ggc | gag | tat | agc | gac | tgc | aaa | gac | gcg | gac | ctc | gtg | gtc | ata | 240 |
| Tyr | Ser | Gly | Glu | Tyr | Ser | Asp | Cys | Lys | Asp | Ala | Asp | Leu | Val | Val | Ile | |
| 65 | | | | | 70 | | | | | 75 | | | | | 80 | |

| acc | gcg | gga | gcg | cca | cag | aag | ccc | gga | gaa | tcg | agg | ctg | gac | ctt | gtc | 288 |
| Thr | Ala | Gly | Ala | Pro | Gln | Lys | Pro | Gly | Glu | Ser | Arg | Leu | Asp | Leu | Val | |
| | | | | 85 | | | | | 90 | | | | | 95 | | |

| aac | aaa | aac | ttg | aac | atc | ctg | tcc | tcg | atc | gtg | aag | ccc | gtg | gta | gac | 336 |
| Asn | Lys | Asn | Leu | Asn | Ile | Leu | Ser | Ser | Ile | Val | Lys | Pro | Val | Val | Asp | |
| | | | 100 | | | | | 105 | | | | | 110 | | | |

| tcc | ggg | ttc | gac | ggc | atc | ttc | ctg | gtg | gcc | gcc | aac | ccc | gtc | gac | atc | 384 |
| Ser | Gly | Phe | Asp | Gly | Ile | Phe | Leu | Val | Ala | Ala | Asn | Pro | Val | Asp | Ile | |
| | | | 115 | | | | | 120 | | | | | 125 | | | |

| ctc | acc | tat | gcg | acc | tgg | aag | ttc | agc | ggg | ttt | ccg | aag | gac | cgg | gtc | 432 |
| Leu | Thr | Tyr | Ala | Thr | Trp | Lys | Phe | Ser | Gly | Phe | Pro | Lys | Asp | Arg | Val | |
| | 130 | | | | | 135 | | | | | 140 | | | | | |

| att | ggc | agt | ggg | acg | tcg | ctg | gat | agc | tcg | cgt | ctg | cga | gtt | gct | ctg | 480 |
| Ile | Gly | Ser | Gly | Thr | Ser | Leu | Asp | Ser | Ser | Arg | Leu | Arg | Val | Ala | Leu | |
| 145 | | | | | 150 | | | | | 155 | | | | | 160 | |

| ggg | aag | caa | ttc | aac | gtg | gat | ccg | cgc | tct | gtg | gat | gcg | tat | atc | atg | 528 |
| Gly | Lys | Gln | Phe | Asn | Val | Asp | Pro | Arg | Ser | Val | Asp | Ala | Tyr | Ile | Met | |
| | | | | 165 | | | | | 170 | | | | | 175 | | |

| ggc | gag | cac | ggc | gat | agt | gag | ttc | gcc | gca | tat | tcc | acc | gcc | acg | atc | 576 |
| Gly | Glu | His | Gly | Asp | Ser | Glu | Phe | Ala | Ala | Tyr | Ser | Thr | Ala | Thr | Ile | |
| | | | 180 | | | | | 185 | | | | | 190 | | | |

| ggc | act | cgg | ccc | gtg | cgc | gac | gtt | gcg | aag | gaa | cag | ggc | gta | tcc | gac | 624 |
| Gly | Thr | Arg | Pro | Val | Arg | Asp | Val | Ala | Lys | Glu | Gln | Gly | Val | Ser | Asp | |
| | | | 195 | | | | | 200 | | | | | 205 | | | |

| gag | gac | ctg | gcc | aag | ctg | gaa | gat | ggc | gtc | cgc | aac | aag | gcc | tac | gac | 672 |
| Glu | Asp | Leu | Ala | Lys | Leu | Glu | Asp | Gly | Val | Arg | Asn | Lys | Ala | Tyr | Asp | |
| | 210 | | | | | 215 | | | | | 220 | | | | | |

| atc | atc | aat | ctc | aag | ggc | gcg | acc | ttc | tac | ggt | att | ggt | acc | gcc | ctg | 720 |
| Ile | Ile | Asn | Leu | Lys | Gly | Ala | Thr | Phe | Tyr | Gly | Ile | Gly | Thr | Ala | Leu | |
| 225 | | | | | 230 | | | | | 235 | | | | | 240 | |

| atg | cgg | atc | tcc | aag | gcc | atc | ctg | cgc | gat | gag | aac | gcc | gtg | ttg | ccg | 768 |
| Met | Arg | Ile | Ser | Lys | Ala | Ile | Leu | Arg | Asp | Glu | Asn | Ala | Val | Leu | Pro | |
| | | | | 245 | | | | | 250 | | | | | 255 | | |

| gtg | ggg | gct | tac | atg | gat | ggc | cag | tac | ggc | ctg | aac | gat | atc | tac | atc | 816 |
| Val | Gly | Ala | Tyr | Met | Asp | Gly | Gln | Tyr | Gly | Leu | Asn | Asp | Ile | Tyr | Ile | |
| | | | | 260 | | | | | 265 | | | | | 270 | | |

| ggc | aca | ccg | gcc | gtc | atc | ggt | ggc | acc | ggt | ctg | aag | cag | atc | atc | gag | 864 |
| Gly | Thr | Pro | Ala | Val | Ile | Gly | Gly | Thr | Gly | Leu | Lys | Gln | Ile | Ile | Glu | |
| | | 275 | | | | | 280 | | | | | 285 | | | | |

| agc | ccg | ctg | tcc | gcc | gac | gag | ctg | aaa | aag | atg | cag | gac | agc | gcc | gca | 912 |
| Ser | Pro | Leu | Ser | Ala | Asp | Glu | Leu | Lys | Lys | Met | Gln | Asp | Ser | Ala | Ala | |
| | 290 | | | | | 295 | | | | | 300 | | | | | |

| acg | ctc | aaa | aaa | gtc | ctc | aat | gat | ggc | ctg | gcc | gaa | ctg | gag | aat | aag | 960 |
| Thr | Leu | Lys | Lys | Val | Leu | Asn | Asp | Gly | Leu | Ala | Glu | Leu | Glu | Asn | Lys | |
| 305 | | | | | 310 | | | | | 315 | | | | | 320 | |

| taa | | | | | | | | | | | | | | | | 963 |

<210> SEQ ID NO 20
<211> LENGTH: 320
<212> TYPE: PRT
<213> ORGANISM: Artificial
<220> FEATURE:
<223> OTHER INFORMATION: Synthetic Construct

<400> SEQUENCE: 20

```
Met Ser Ser Met Pro Asn His Gln Lys Val Val Leu Val Gly Asp Gly
1               5                   10                  15

Ala Val Gly Ser Ser Tyr Ala Phe Ala Met Ala Gln Gln Gly Ile Ala
            20                  25                  30

Glu Glu Phe Val Ile Val Asp Val Val Lys Asp Arg Thr Lys Gly Asp
        35                  40                  45

Ala Leu Asp Leu Glu Asp Ala Gln Ala Phe Thr Ala Pro Lys Lys Ile
    50                  55                  60

Tyr Ser Gly Glu Tyr Ser Asp Cys Lys Asp Ala Asp Leu Val Val Ile
65                  70                  75                  80

Thr Ala Gly Ala Pro Gln Lys Pro Gly Glu Ser Arg Leu Asp Leu Val
                85                  90                  95

Asn Lys Asn Leu Asn Ile Leu Ser Ser Ile Val Lys Pro Val Val Asp
            100                 105                 110

Ser Gly Phe Asp Gly Ile Phe Leu Val Ala Ala Asn Pro Val Asp Ile
        115                 120                 125

Leu Thr Tyr Ala Thr Trp Lys Phe Ser Gly Phe Pro Lys Asp Arg Val
    130                 135                 140

Ile Gly Ser Gly Thr Ser Leu Asp Ser Ser Arg Leu Arg Val Ala Leu
145                 150                 155                 160

Gly Lys Gln Phe Asn Val Asp Pro Arg Ser Val Asp Ala Tyr Ile Met
                165                 170                 175

Gly Glu His Gly Asp Ser Glu Phe Ala Ala Tyr Ser Thr Ala Thr Ile
            180                 185                 190

Gly Thr Arg Pro Val Arg Asp Val Ala Lys Glu Gln Gly Val Ser Asp
        195                 200                 205

Glu Asp Leu Ala Lys Leu Glu Asp Gly Val Arg Asn Lys Ala Tyr Asp
    210                 215                 220

Ile Ile Asn Leu Lys Gly Ala Thr Phe Tyr Gly Ile Gly Thr Ala Leu
225                 230                 235                 240

Met Arg Ile Ser Lys Ala Ile Leu Arg Asp Glu Asn Ala Val Leu Pro
                245                 250                 255

Val Gly Ala Tyr Met Asp Gly Gln Tyr Gly Leu Asn Asp Ile Tyr Ile
            260                 265                 270

Gly Thr Pro Ala Val Ile Gly Gly Thr Gly Leu Lys Gln Ile Ile Glu
        275                 280                 285

Ser Pro Leu Ser Ala Asp Glu Leu Lys Lys Met Gln Asp Ser Ala Ala
    290                 295                 300

Thr Leu Lys Lys Val Leu Asn Asp Gly Leu Ala Glu Leu Glu Asn Lys
305                 310                 315                 320
```

<210> SEQ ID NO 21
<211> LENGTH: 963
<212> TYPE: DNA
<213> ORGANISM: Artificial
<220> FEATURE:
<223> OTHER INFORMATION: Synthetic construct (Lactobacillus acidophilus LDH)
<220> FEATURE:
<221> NAME/KEY: CDS
<222> LOCATION: (1)..(963)

<400> SEQUENCE: 21

```
atg tcg tcg atg cct aac cat cag aaa gtc gtc ctg gtg ggc gac gga      48
Met Ser Ser Met Pro Asn His Gln Lys Val Val Leu Val Gly Asp Gly
1               5                   10                  15
```

-continued

| | |
|---|---|
| gcg gtc ggc agc tca tac gcc ttc gcg atg gcg caa cag gga atc gcg<br>Ala Val Gly Ser Ser Tyr Ala Phe Ala Met Ala Gln Gln Gly Ile Ala<br>20 25 30 | 96 |
| gaa gaa ttc gtc atc gtc gac gtg gtg aag gac cgc acc aag ggc gac<br>Glu Glu Phe Val Ile Val Asp Val Val Lys Asp Arg Thr Lys Gly Asp<br>35 40 45 | 144 |
| gcc ttg gac ctc gaa gat gca cag gcc ttc acg gcc ccg aag aaa atc<br>Ala Leu Asp Leu Glu Asp Ala Gln Ala Phe Thr Ala Pro Lys Lys Ile<br>50 55 60 | 192 |
| tac agc ggc gag tat agc gac tgc aaa gac gcg gac ctc gtg gtc ata<br>Tyr Ser Gly Glu Tyr Ser Asp Cys Lys Asp Ala Asp Leu Val Val Ile<br>65 70 75 80 | 240 |
| acc gcg gga gcg cca cag aag ccc gga gaa tcg agg ctg gac ctt gtc<br>Thr Ala Gly Ala Pro Gln Lys Pro Gly Glu Ser Arg Leu Asp Leu Val<br>85 90 95 | 288 |
| aac aaa aac ttg aac atc ctg tcc tcg atc gtg aag ccc gtg gta gac<br>Asn Lys Asn Leu Asn Ile Leu Ser Ser Ile Val Lys Pro Val Val Asp<br>100 105 110 | 336 |
| tcc ggg ttc gac ggc atc ttc ctg gtg gcc gcc aac ccc gtc gac atc<br>Ser Gly Phe Asp Gly Ile Phe Leu Val Ala Ala Asn Pro Val Asp Ile<br>115 120 125 | 384 |
| ctc acc tat gcg acc tgg aag ttc agc ggg ttt ccg aag gac cgg gtc<br>Leu Thr Tyr Ala Thr Trp Lys Phe Ser Gly Phe Pro Lys Asp Arg Val<br>130 135 140 | 432 |
| att ggc agt ggg acg tcg ctg gat agc tcg cgt ctg cga gtt gct ctg<br>Ile Gly Ser Gly Thr Ser Leu Asp Ser Ser Arg Leu Arg Val Ala Leu<br>145 150 155 160 | 480 |
| ggg aag caa ttc aac gtg gat ccg cgc tct gtg gat gcg tat atc atg<br>Gly Lys Gln Phe Asn Val Asp Pro Arg Ser Val Asp Ala Tyr Ile Met<br>165 170 175 | 528 |
| ggc gag cac ggc gat agt gag ttc gcc gca tat tcc acc gcc acg atc<br>Gly Glu His Gly Asp Ser Glu Phe Ala Ala Tyr Ser Thr Ala Thr Ile<br>180 185 190 | 576 |
| ggc act cgg ccc gtg cgc gac gtt gcg aag gaa cag ggc gta tcc gac<br>Gly Thr Arg Pro Val Arg Asp Val Ala Lys Glu Gln Gly Val Ser Asp<br>195 200 205 | 624 |
| gag gac ctg gcc aag ctg gaa gat ggc gtc cgc aac aag gcc tac gac<br>Glu Asp Leu Ala Lys Leu Glu Asp Gly Val Arg Asn Lys Ala Tyr Asp<br>210 215 220 | 672 |
| atc atc aat ctc aag ggc gcg acc ttc tac ggt att ggt acc gcc ctg<br>Ile Ile Asn Leu Lys Gly Ala Thr Phe Tyr Gly Ile Gly Thr Ala Leu<br>225 230 235 240 | 720 |
| atg cgg atc tcc aag gcc atc ctg cgc gat gag aac gcc gtg ttg ccg<br>Met Arg Ile Ser Lys Ala Ile Leu Arg Asp Glu Asn Ala Val Leu Pro<br>245 250 255 | 768 |
| gtg ggg gct tac atg gat ggc cag tac ggc ctg aac gat atc tac atc<br>Val Gly Ala Tyr Met Asp Gly Gln Tyr Gly Leu Asn Asp Ile Tyr Ile<br>260 265 270 | 816 |
| ggc aca ccg gcc gtc atc ggt ggc acc ggt ctg aag cag atc atc gag<br>Gly Thr Pro Ala Val Ile Gly Gly Thr Gly Leu Lys Gln Ile Ile Glu<br>275 280 285 | 864 |
| agc ccg ctg tcc gcc gac gag ctg aaa aag atg cag gac agc gcc gca<br>Ser Pro Leu Ser Ala Asp Glu Leu Lys Lys Met Gln Asp Ser Ala Ala<br>290 295 300 | 912 |
| acg ctc aaa aaa gtc ctc aat gat ggc ctg gcc gaa ctg gag aat aag<br>Thr Leu Lys Lys Val Leu Asn Asp Gly Leu Ala Glu Leu Glu Asn Lys<br>305 310 315 320 | 960 |
| taa | 963 |

```
<210> SEQ ID NO 22
<211> LENGTH: 320
<212> TYPE: PRT
<213> ORGANISM: Artificial
<220> FEATURE:
<223> OTHER INFORMATION: Synthetic Construct

<400> SEQUENCE: 22

Met Ser Ser Met Pro Asn His Gln Lys Val Val Leu Val Gly Asp Gly
1               5                   10                  15

Ala Val Gly Ser Ser Tyr Ala Phe Ala Met Ala Gln Gln Gly Ile Ala
            20                  25                  30

Glu Glu Phe Val Ile Val Asp Val Val Lys Asp Arg Thr Lys Gly Asp
        35                  40                  45

Ala Leu Asp Leu Glu Asp Ala Gln Ala Phe Thr Ala Pro Lys Lys Ile
    50                  55                  60

Tyr Ser Gly Glu Tyr Ser Asp Cys Lys Asp Ala Asp Leu Val Val Ile
65                  70                  75                  80

Thr Ala Gly Ala Pro Gln Lys Pro Gly Glu Ser Arg Leu Asp Leu Val
                85                  90                  95

Asn Lys Asn Leu Asn Ile Leu Ser Ser Ile Val Lys Pro Val Val Asp
            100                 105                 110

Ser Gly Phe Asp Gly Ile Phe Leu Val Ala Ala Asn Pro Val Asp Ile
        115                 120                 125

Leu Thr Tyr Ala Thr Trp Lys Phe Ser Gly Phe Pro Lys Asp Arg Val
    130                 135                 140

Ile Gly Ser Gly Thr Ser Leu Asp Ser Ser Arg Leu Arg Val Ala Leu
145                 150                 155                 160

Gly Lys Gln Phe Asn Val Asp Pro Arg Ser Val Asp Ala Tyr Ile Met
                165                 170                 175

Gly Glu His Gly Asp Ser Glu Phe Ala Ala Tyr Ser Thr Ala Thr Ile
            180                 185                 190

Gly Thr Arg Pro Val Arg Asp Val Ala Lys Glu Gln Gly Val Ser Asp
        195                 200                 205

Glu Asp Leu Ala Lys Leu Glu Asp Gly Val Arg Asn Lys Ala Tyr Asp
    210                 215                 220

Ile Ile Asn Leu Lys Gly Ala Thr Phe Tyr Gly Ile Gly Thr Ala Leu
225                 230                 235                 240

Met Arg Ile Ser Lys Ala Ile Leu Arg Asp Glu Asn Ala Val Leu Pro
                245                 250                 255

Val Gly Ala Tyr Met Asp Gly Gln Tyr Gly Leu Asn Asp Ile Tyr Ile
            260                 265                 270

Gly Thr Pro Ala Val Ile Gly Gly Thr Gly Leu Lys Gln Ile Ile Glu
        275                 280                 285

Ser Pro Leu Ser Ala Asp Glu Leu Lys Lys Met Gln Asp Ser Ala Ala
    290                 295                 300

Thr Leu Lys Lys Val Leu Asn Asp Gly Leu Ala Glu Leu Glu Asn Lys
305                 310                 315                 320

<210> SEQ ID NO 23
<211> LENGTH: 954
<212> TYPE: DNA
<213> ORGANISM: Artificial
<220> FEATURE:
<223> OTHER INFORMATION: Synthetic construct (Staphylococcus aureus LDH)
<220> FEATURE:
<221> NAME/KEY: CDS
<222> LOCATION: (1)..(954)
```

<400> SEQUENCE: 23

```
atg aac aag ttc aag ggc aac aaa gtc gtg ttg atc ggg aat ggc gcc      48
Met Asn Lys Phe Lys Gly Asn Lys Val Val Leu Ile Gly Asn Gly Ala
1               5                   10                  15 gtc ggc tcg tcc tac gcg ttt tcg ctg gtc aac cag tcc atc gtg gac      96
Val Gly Ser Ser Tyr Ala Phe Ser Leu Val Asn Gln Ser Ile Val Asp
                20                  25                  30 gaa ctc gtc ata atc gac ctc gac acc gaa aag gtt cgg ggt gac gtc     144
Glu Leu Val Ile Ile Asp Leu Asp Thr Glu Lys Val Arg Gly Asp Val
            35                  40                  45 atg gac ctc aag cac gcc act ccg tat agc ccc acg acc gtg cgc gtg     192
Met Asp Leu Lys His Ala Thr Pro Tyr Ser Pro Thr Thr Val Arg Val
50                  55                  60 aag gcc gga gag tac agc gac tgc cat gac gcc aac ctg gtc gtc att     240
Lys Ala Gly Glu Tyr Ser Asp Cys His Asp Ala Asn Leu Val Val Ile
65                  70                  75                  80 tgc gcg ggt gcg gcg cag aaa ccg ggc gaa acc cgc ctc gat ctg gtg     288
Cys Ala Gly Ala Ala Gln Lys Pro Gly Glu Thr Arg Leu Asp Leu Val
                85                  90                  95 agc aag aac ctc aag atc ttc aag agt att gtg gga gaa gta atg gcc     336
Ser Lys Asn Leu Lys Ile Phe Lys Ser Ile Val Gly Glu Val Met Ala
                100                 105                 110 tcg aag ttc gac ggc atc ttc ctg gtc gca acc aat cca gtg gat atc     384
Ser Lys Phe Asp Gly Ile Phe Leu Val Ala Thr Asn Pro Val Asp Ile
            115                 120                 125 ctg gcc tac gca acc tgg aag ttc tcg gga ctg ccc aaa gag cga gtc     432
Leu Ala Tyr Ala Thr Trp Lys Phe Ser Gly Leu Pro Lys Glu Arg Val
130                 135                 140 atc ggc tcc ggc acc atc ctt gac tca gcg cgt ttc cgg ctg ctg ttg     480
Ile Gly Ser Gly Thr Ile Leu Asp Ser Ala Arg Phe Arg Leu Leu Leu
145                 150                 155                 160 agc gag gcc ttc gat gtg gcg ccc agg tct gtc gat gcc cag atc atc     528
Ser Glu Ala Phe Asp Val Ala Pro Arg Ser Val Asp Ala Gln Ile Ile
                165                 170                 175 ggc gag cac ggc gac acc gag ctt ccc gtg tgg tcc cat gcc aat atc     576
Gly Glu His Gly Asp Thr Glu Leu Pro Val Trp Ser His Ala Asn Ile
            180                 185                 190 gct ggg cag ccg ctg aaa acg ctg ctg gag caa cgt cct gag ggc aag     624
Ala Gly Gln Pro Leu Lys Thr Leu Leu Glu Gln Arg Pro Glu Gly Lys
        195                 200                 205 gcg cag atc gag cag atc ttt gtg cag acg cgc gac gcc gcc tac gac     672
Ala Gln Ile Glu Gln Ile Phe Val Gln Thr Arg Asp Ala Ala Tyr Asp
210                 215                 220 atc atc caa gcg aag ggc gct aca tac tat ggg gtg gcg atg ggg ctc     720
Ile Ile Gln Ala Lys Gly Ala Thr Tyr Tyr Gly Val Ala Met Gly Leu
225                 230                 235                 240 gcg cgc atc acg gaa gcc att ttc cgg aat gaa gat gca gtc ctg acc     768
Ala Arg Ile Thr Glu Ala Ile Phe Arg Asn Glu Asp Ala Val Leu Thr
                245                 250                 255 gta agc gcc ctg ctg gaa ggt gag tat gac gaa gaa gat gtc tac atc     816
Val Ser Ala Leu Leu Glu Gly Glu Tyr Asp Glu Glu Asp Val Tyr Ile
            260                 265                 270 ggc gtt ccg gcc gtg atc aac cgc aac ggc atc cgg aac gtc gtg gag     864
Gly Val Pro Ala Val Ile Asn Arg Asn Gly Ile Arg Asn Val Val Glu
        275                 280                 285 atc ccg ctg aac gat gaa gaa cag agc aag ttc gcc cac tcc gcg aaa     912
Ile Pro Leu Asn Asp Glu Glu Gln Ser Lys Phe Ala His Ser Ala Lys
290                 295                 300
```

```
acc ctg aaa gac atc atg gcc gag gcc gag gaa ttg aag taa                954
Thr Leu Lys Asp Ile Met Ala Glu Ala Glu Glu Leu Lys
305                 310                 315
```

<210> SEQ ID NO 24
<211> LENGTH: 317
<212> TYPE: PRT
<213> ORGANISM: Artificial
<220> FEATURE:
<223> OTHER INFORMATION: Synthetic Construct

<400> SEQUENCE: 24

```
Met Asn Lys Phe Lys Gly Asn Lys Val Val Leu Ile Gly Asn Gly Ala
1               5                   10                  15

Val Gly Ser Ser Tyr Ala Phe Ser Leu Val Asn Gln Ser Ile Val Asp
            20                  25                  30

Glu Leu Val Ile Ile Asp Leu Asp Thr Glu Lys Val Arg Gly Asp Val
        35                  40                  45

Met Asp Leu Lys His Ala Thr Pro Tyr Ser Pro Thr Thr Val Arg Val
    50                  55                  60

Lys Ala Gly Glu Tyr Ser Asp Cys His Asp Ala Asn Leu Val Val Ile
65                  70                  75                  80

Cys Ala Gly Ala Ala Gln Lys Pro Gly Glu Thr Arg Leu Asp Leu Val
                85                  90                  95

Ser Lys Asn Leu Lys Ile Phe Lys Ser Ile Val Gly Glu Val Met Ala
            100                 105                 110

Ser Lys Phe Asp Gly Ile Phe Leu Val Ala Thr Asn Pro Val Asp Ile
        115                 120                 125

Leu Ala Tyr Ala Thr Trp Lys Phe Ser Gly Leu Pro Lys Glu Arg Val
    130                 135                 140

Ile Gly Ser Gly Thr Ile Leu Asp Ser Ala Arg Phe Arg Leu Leu Leu
145                 150                 155                 160

Ser Glu Ala Phe Asp Val Ala Pro Arg Ser Val Asp Ala Gln Ile Ile
                165                 170                 175

Gly Glu His Gly Asp Thr Glu Leu Pro Val Trp Ser His Ala Asn Ile
            180                 185                 190

Ala Gly Gln Pro Leu Lys Thr Leu Leu Glu Gln Arg Pro Glu Gly Lys
        195                 200                 205

Ala Gln Ile Glu Gln Ile Phe Val Gln Thr Arg Asp Ala Ala Tyr Asp
    210                 215                 220

Ile Ile Gln Ala Lys Gly Ala Thr Tyr Tyr Gly Val Ala Met Gly Leu
225                 230                 235                 240

Ala Arg Ile Thr Glu Ala Ile Phe Arg Asn Glu Asp Ala Val Leu Thr
                245                 250                 255

Val Ser Ala Leu Leu Glu Gly Glu Tyr Asp Glu Asp Val Tyr Ile
            260                 265                 270

Gly Val Pro Ala Val Ile Asn Arg Asn Gly Ile Arg Asn Val Val Glu
        275                 280                 285

Ile Pro Leu Asn Asp Glu Glu Gln Ser Lys Phe Ala His Ser Ala Lys
    290                 295                 300

Thr Leu Lys Asp Ile Met Ala Glu Ala Glu Glu Leu Lys
305                 310                 315
```

<210> SEQ ID NO 25
<211> LENGTH: 954
<212> TYPE: DNA
<213> ORGANISM: Artificial

```
<220> FEATURE:
<223> OTHER INFORMATION: Synthetic construct (Bacillus caldolyticus LDH)
<220> FEATURE:
<221> NAME/KEY: CDS
<222> LOCATION: (1)..(954)

<400> SEQUENCE: 25 atg aaa aac aat ggg ggc acc cgc gtg gtc gtc atc gga acc ggc ttc      48
Met Lys Asn Asn Gly Gly Thr Arg Val Val Val Ile Gly Thr Gly Phe
1               5                   10                  15 gtc ggc gcc tcg tac gcg ttc gcc ctg atg aac cag ggt att gcc gac      96
Val Gly Ala Ser Tyr Ala Phe Ala Leu Met Asn Gln Gly Ile Ala Asp
                20                  25                  30 gag atc gtg ctg atc gac gcg aac gag tcc aag gcc atc ggc gat gca     144
Glu Ile Val Leu Ile Asp Ala Asn Glu Ser Lys Ala Ile Gly Asp Ala
            35                  40                  45 atg gac ttt aac cac ggc aag gtt ttc gcc ccc aaa ccg gcg gac atc     192
Met Asp Phe Asn His Gly Lys Val Phe Ala Pro Lys Pro Ala Asp Ile
    50                  55                  60 tgg cat ggc gat tat gac gac tgc cgg gac gcc gac ctg gtg gtg atc     240
Trp His Gly Asp Tyr Asp Asp Cys Arg Asp Ala Asp Leu Val Val Ile
65                  70                  75                  80 tgc gcg ggt gcg aac cag aag ccg gga gaa acc cgc ctt gac ctg gtt     288
Cys Ala Gly Ala Asn Gln Lys Pro Gly Glu Thr Arg Leu Asp Leu Val
                85                  90                  95 gac aag aac atc gcc atc ttc cgc tcg atc gtc gaa agc gtc atg gcc     336
Asp Lys Asn Ile Ala Ile Phe Arg Ser Ile Val Glu Ser Val Met Ala
                100                 105                 110 agc ggg ttc caa ggc ctc ttc ctg gtc gcc acc aac ccc gtc gac att     384
Ser Gly Phe Gln Gly Leu Phe Leu Val Ala Thr Asn Pro Val Asp Ile
            115                 120                 125 ctc acg tac gcg acc tgg aaa ttc tcg ggc ctg ccg cac gag cgg gtg     432
Leu Thr Tyr Ala Thr Trp Lys Phe Ser Gly Leu Pro His Glu Arg Val
    130                 135                 140 atc ggc agc ggc acg atc ctg gat act gcc cgg ttt cga ttc ttg ctg     480
Ile Gly Ser Gly Thr Ile Leu Asp Thr Ala Arg Phe Arg Phe Leu Leu
145                 150                 155                 160 ggt gag tac ttc agc gtc gcc cca cag aat gtg cat gcg tac atc att     528
Gly Glu Tyr Phe Ser Val Ala Pro Gln Asn Val His Ala Tyr Ile Ile
                165                 170                 175 ggc gaa cat ggc gat acg gaa ctc ccc gtc tgg tcc cag gct gat atc     576
Gly Glu His Gly Asp Thr Glu Leu Pro Val Trp Ser Gln Ala Asp Ile
                180                 185                 190 ggg gga gtc ccg atc cgg aag ctc gtg gaa tcc aag ggc gaa gaa gcg     624
Gly Gly Val Pro Ile Arg Lys Leu Val Glu Ser Lys Gly Glu Glu Ala
            195                 200                 205 cag aaa gaa ttg gag cgt atc ttc gtg aat gta cgt gat gcc gcc tat     672
Gln Lys Glu Leu Glu Arg Ile Phe Val Asn Val Arg Asp Ala Ala Tyr
    210                 215                 220 cag ata atc gaa aag aaa ggc gcc acc tac tat ggt atc gcg atg ggg     720
Gln Ile Ile Glu Lys Lys Gly Ala Thr Tyr Tyr Gly Ile Ala Met Gly
225                 230                 235                 240 ctg gcc agg gtg acc cgc gca atc ctg cac aac gag aat gcg atc ctg     768
Leu Ala Arg Val Thr Arg Ala Ile Leu His Asn Glu Asn Ala Ile Leu
                245                 250                 255 aca gtg tcc gcg tac ctg gat ggg cct tac ggc gag cgc gac gtg tat     816
Thr Val Ser Ala Tyr Leu Asp Gly Pro Tyr Gly Glu Arg Asp Val Tyr
                260                 265                 270 atc ggc gtg ccg gca gtc atc aac cgg aac ggc atc cgc gaa gtc atc     864
Ile Gly Val Pro Ala Val Ile Asn Arg Asn Gly Ile Arg Glu Val Ile
            275                 280                 285
```

```
gag atc gag ctg aac gac gac gag aag aac cgc ttc cac cac tcg gcc      912
Glu Ile Glu Leu Asn Asp Asp Glu Lys Asn Arg Phe His His Ser Ala
290                 295                 300 gct acc ctc aag agt gtg ttg gcc cgg ttc ttc acg cgc taa              954
Ala Thr Leu Lys Ser Val Leu Ala Arg Phe Phe Thr Arg
305                 310                 315
```

<210> SEQ ID NO 26
<211> LENGTH: 317
<212> TYPE: PRT
<213> ORGANISM: Artificial
<220> FEATURE:
<223> OTHER INFORMATION: Synthetic Construct

<400> SEQUENCE: 26

```
Met Lys Asn Asn Gly Gly Thr Arg Val Val Ile Gly Thr Gly Phe
1               5                   10                  15

Val Gly Ala Ser Tyr Ala Phe Ala Leu Met Asn Gln Gly Ile Ala Asp
            20                  25                  30

Glu Ile Val Leu Ile Asp Ala Asn Glu Ser Lys Ala Ile Gly Asp Ala
        35                  40                  45

Met Asp Phe Asn His Gly Lys Val Phe Ala Pro Lys Pro Ala Asp Ile
50                  55                  60

Trp His Gly Asp Tyr Asp Asp Cys Arg Asp Ala Asp Leu Val Val Ile
65                  70                  75                  80

Cys Ala Gly Ala Asn Gln Lys Pro Gly Glu Thr Arg Leu Asp Leu Val
                85                  90                  95

Asp Lys Asn Ile Ala Ile Phe Arg Ser Ile Val Glu Ser Val Met Ala
            100                 105                 110

Ser Gly Phe Gln Gly Leu Phe Leu Val Ala Thr Asn Pro Val Asp Ile
        115                 120                 125

Leu Thr Tyr Ala Thr Trp Lys Phe Ser Gly Leu Pro His Glu Arg Val
130                 135                 140

Ile Gly Ser Gly Thr Ile Leu Asp Thr Ala Arg Phe Arg Phe Leu Leu
145                 150                 155                 160

Gly Glu Tyr Phe Ser Val Ala Pro Gln Asn Val His Ala Tyr Ile Ile
                165                 170                 175

Gly Glu His Gly Asp Thr Glu Leu Pro Val Trp Ser Gln Ala Asp Ile
            180                 185                 190

Gly Gly Val Pro Ile Arg Lys Leu Val Glu Ser Lys Gly Glu Glu Ala
        195                 200                 205

Gln Lys Glu Leu Glu Arg Ile Phe Val Asn Val Arg Asp Ala Ala Tyr
210                 215                 220

Gln Ile Ile Glu Lys Lys Gly Ala Thr Tyr Tyr Gly Ile Ala Met Gly
225                 230                 235                 240

Leu Ala Arg Val Thr Arg Ala Ile Leu His Asn Glu Asn Ala Ile Leu
                245                 250                 255

Thr Val Ser Ala Tyr Leu Asp Gly Pro Tyr Gly Glu Arg Asp Val Tyr
            260                 265                 270

Ile Gly Val Pro Ala Val Ile Asn Arg Asn Gly Ile Arg Glu Val Ile
        275                 280                 285

Glu Ile Glu Leu Asn Asp Asp Glu Lys Asn Arg Phe His His Ser Ala
290                 295                 300

Ala Thr Leu Lys Ser Val Leu Ala Arg Phe Phe Thr Arg
305                 310                 315
```

<210> SEQ ID NO 27
<211> LENGTH: 1002
<212> TYPE: DNA
<213> ORGANISM: Artificial
<220> FEATURE:
<223> OTHER INFORMATION: Synthetic construct (Actinomyces visosus LDH)
<220> FEATURE:
<221> NAME/KEY: CDS
<222> LOCATION: (1)..(1002)

<400> SEQUENCE: 27

| | | | | | | | | | | | | | | | | |
|---|---|---|---|---|---|---|---|---|---|---|---|---|---|---|---|---|
| atg | tcc | gac | cat | atc | acg | aca | acc | gcc | gag | ggc | tcc | tac | ccg | acc | aat | 48 |
| Met | Ser | Asp | His | Ile | Thr | Thr | Thr | Ala | Glu | Gly | Ser | Tyr | Pro | Thr | Asn | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cgg | tcc | gga | cgg | ccc | agc | aaa | gtg | gcc | gtg | atc | ggc | gcg | ggc | gcg | gtc | 96 |
| Arg | Ser | Gly | Arg | Pro | Ser | Lys | Val | Ala | Val | Ile | Gly | Ala | Gly | Ala | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| ggg | agc | acc | ctg | gcc | tac | gcc | tgt | gtc | acc | aaa | ggc | gtc | gct | cgc | gag | 144 |
| Gly | Ser | Thr | Leu | Ala | Tyr | Ala | Cys | Val | Thr | Lys | Gly | Val | Ala | Arg | Glu | |
| | | 35 | | | | | 40 | | | | | 45 | | | | |

| | | | | | | | | | | | | | | | | |
|---|---|---|---|---|---|---|---|---|---|---|---|---|---|---|---|---|
| gtc | gtc | ttg | cag | gac | ata | gtc | aag | gaa | aaa | gta | gaa | gcc | gaa | gcg | ctg | 192 |
| Val | Val | Leu | Gln | Asp | Ile | Val | Lys | Glu | Lys | Val | Glu | Ala | Glu | Ala | Leu | |
| | 50 | | | | | 55 | | | | | 60 | | | | | |

| | | | | | | | | | | | | | | | | |
|---|---|---|---|---|---|---|---|---|---|---|---|---|---|---|---|---|
| gac | atc | gcc | cag | ggt | atc | cag | ttc | acc | tcc | gcg | gga | agt | gtg | tct | ggc | 240 |
| Asp | Ile | Ala | Gln | Gly | Ile | Gln | Phe | Thr | Ser | Ala | Gly | Ser | Val | Ser | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tcg | gat | gac | ccg | gag | atc | tgc | cgc | gat | gcc | gac | gtg | att | gcc | atc | act | 288 |
| Ser | Asp | Asp | Pro | Glu | Ile | Cys | Arg | Asp | Ala | Asp | Val | Ile | Ala | Ile | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| gca | ggc | gca | aag | cag | aag | ccc | ggc | cag | tcg | cgc | ttg | gag | ctg | gcg | gga | 336 |
| Ala | Gly | Ala | Lys | Gln | Lys | Pro | Gly | Gln | Ser | Arg | Leu | Glu | Leu | Ala | Gly | |
| | | | 100 | | | | | 105 | | | | | 110 | | | |

| | | | | | | | | | | | | | | | | |
|---|---|---|---|---|---|---|---|---|---|---|---|---|---|---|---|---|
| gcg | acc | gtg | ggg | atc | atg | gaa | aag | atc | ctg | ccc | aag | ctc | gtg | gaa | gtt | 384 |
| Ala | Thr | Val | Gly | Ile | Met | Glu | Lys | Ile | Leu | Pro | Lys | Leu | Val | Glu | Val | |
| | | 115 | | | | | 120 | | | | | 125 | | | | |

| | | | | | | | | | | | | | | | | |
|---|---|---|---|---|---|---|---|---|---|---|---|---|---|---|---|---|
| gcc | ccc | aac | gcc | atc | ttc | gtc | ctg | gtc | gcc | aac | ccg | gtc | gat | gtg | gtg | 432 |
| Ala | Pro | Asn | Ala | Ile | Phe | Val | Leu | Val | Ala | Asn | Pro | Val | Asp | Val | Val | |
| | 130 | | | | | 135 | | | | | 140 | | | | | |

| | | | | | | | | | | | | | | | | |
|---|---|---|---|---|---|---|---|---|---|---|---|---|---|---|---|---|
| acg | tac | tgc | gcc | aag | aaa | atc | acc | ggc | ctg | ccg | gag | aac | caa | gtg | ttt | 480 |
| Thr | Tyr | Cys | Ala | Lys | Lys | Ile | Thr | Gly | Leu | Pro | Glu | Asn | Gln | Val | Phe | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ggc | tcg | ggc | act | gtc | ctc | gac | acg | gcc | cgt | atg | cgc | tat | ctg | atc | agc | 528 |
| Gly | Ser | Gly | Thr | Val | Leu | Asp | Thr | Ala | Arg | Met | Arg | Tyr | Leu | Ile | Ser | |
| | | | | 165 | | | | | 170 | | | | | 175 | | |

| | | | | | | | | | | | | | | | | |
|---|---|---|---|---|---|---|---|---|---|---|---|---|---|---|---|---|
| ctc | gaa | acg | ggg | acc | gct | gtc | cag | aac | atc | cac | ggc | tat | atc | gcg | ggt | 576 |
| Leu | Glu | Thr | Gly | Thr | Ala | Val | Gln | Asn | Ile | His | Gly | Tyr | Ile | Ala | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| gag | cat | ggc | gat | tcg | gaa | gtc | cca | ctg | tgg | tcc | tcg | acc | gaa | atc | ggc | 624 |
| Glu | His | Gly | Asp | Ser | Glu | Val | Pro | Leu | Trp | Ser | Ser | Thr | Glu | Ile | Gly | |
| | | 195 | | | | | 200 | | | | | 205 | | | | |

| | | | | | | | | | | | | | | | | |
|---|---|---|---|---|---|---|---|---|---|---|---|---|---|---|---|---|
| ggt | gtg | ccg | att | acg | cag | tgg | ggc | acc | acg | ttg | gac | ggt | ggc | gtg | ttc | 672 |
| Gly | Val | Pro | Ile | Thr | Gln | Trp | Gly | Thr | Thr | Leu | Asp | Gly | Gly | Val | Phe | |
| | 210 | | | | | 215 | | | | | 220 | | | | | |

| | | | | | | | | | | | | | | | | |
|---|---|---|---|---|---|---|---|---|---|---|---|---|---|---|---|---|
| gac | gag | agc | aag | cgc | gag | cgg | atc | gcg | cat | gac | gtc | gtg | cgc | agc | gcc | 720 |
| Asp | Glu | Ser | Lys | Arg | Glu | Arg | Ile | Ala | His | Asp | Val | Val | Arg | Ser | Ala | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tat | cgg | atc | atc | gag | ggg | aag | ggc | gcg | acc | aac | tac | gcg | gtt | ggc | ctg | 768 |
| Tyr | Arg | Ile | Ile | Glu | Gly | Lys | Gly | Ala | Thr | Asn | Tyr | Ala | Val | Gly | Leu | |
| | | | | 245 | | | | | 250 | | | | | 255 | | |

| | | | | | | | | | | | | | | | | |
|---|---|---|---|---|---|---|---|---|---|---|---|---|---|---|---|---|
| gcc | gtg | cag | cgt | atc | atc | ggc | gca | gtg | ctg | aat | gac | gag | caa | agg | gtc | 816 |
| Ala | Val | Gln | Arg | Ile | Ile | Gly | Ala | Val | Leu | Asn | Asp | Glu | Gln | Arg | Val | |

| | | | | | | | | | | | | | | |
|---|---|---|---|---|---|---|---|---|---|---|---|---|---|---|
| | | | | 260 | | | | 265 | | | | 270 | | |
| ctc | acg | atc | agc | ccg | ctg | ctc | gat | aac | tgg | cac | ggc | att | tca | gat | gtg | 864 |
| Leu | Thr | Ile | Ser | Pro | Leu | Leu | Asp | Asn | Trp | His | Gly | Ile | Ser | Asp | Val |
| | | 275 | | | | 280 | | | | 285 | | | | |
| tgc | atg | gcc | gtc | cct | acc | att | gtt | ggc | cgc | gag | ggt | gcg | gga | cgc | cgg | 912 |
| Cys | Met | Ala | Val | Pro | Thr | Ile | Val | Gly | Arg | Glu | Gly | Ala | Gly | Arg | Arg |
| | 290 | | | | 295 | | | | 300 | | | | |
| ctg | gag | ctc | ccg | ctg | acc | ccc | gaa | gaa | aag | gaa | cga | ctg | acc | gct | tcc | 960 |
| Leu | Glu | Leu | Pro | Leu | Thr | Pro | Glu | Glu | Lys | Glu | Arg | Leu | Thr | Ala | Ser |
| 305 | | | | 310 | | | | 315 | | | | 320 | | |
| gcc | gac | cac | ctt | cgg | gaa | gta | gcc | aga | ggg | ctg | ggg | tac | taa | | | 1002 |
| Ala | Asp | His | Leu | Arg | Glu | Val | Ala | Arg | Gly | Leu | Gly | Tyr | | | |
| | | | 325 | | | | 330 | | | | | |

<210> SEQ ID NO 28
<211> LENGTH: 333
<212> TYPE: PRT
<213> ORGANISM: Artificial
<220> FEATURE:
<223> OTHER INFORMATION: Synthetic Construct

<400> SEQUENCE: 28

Met Ser Asp His Ile Thr Thr Thr Ala Glu Gly Ser Tyr Pro Thr Asn
1               5                   10                  15

Arg Ser Gly Arg Pro Ser Lys Val Ala Val Ile Gly Ala Gly Ala Val
            20                  25                  30

Gly Ser Thr Leu Ala Tyr Ala Cys Val Thr Lys Gly Val Ala Arg Glu
        35                  40                  45

Val Val Leu Gln Asp Ile Val Lys Glu Lys Val Glu Ala Glu Ala Leu
    50                  55                  60

Asp Ile Ala Gln Gly Ile Gln Phe Thr Ser Ala Gly Ser Val Ser Gly
65                  70                  75                  80

Ser Asp Asp Pro Glu Ile Cys Arg Asp Ala Asp Val Ile Ala Ile Thr
                85                  90                  95

Ala Gly Ala Lys Gln Lys Pro Gly Gln Ser Arg Leu Glu Leu Ala Gly
            100                 105                 110

Ala Thr Val Gly Ile Met Glu Lys Ile Leu Pro Lys Leu Val Glu Val
        115                 120                 125

Ala Pro Asn Ala Ile Phe Val Leu Val Ala Asn Pro Val Asp Val Val
    130                 135                 140

Thr Tyr Cys Ala Lys Lys Ile Thr Gly Leu Pro Glu Asn Gln Val Phe
145                 150                 155                 160

Gly Ser Gly Thr Val Leu Asp Thr Ala Arg Met Arg Tyr Leu Ile Ser
                165                 170                 175

Leu Glu Thr Gly Thr Ala Val Gln Asn Ile His Gly Tyr Ile Ala Gly
            180                 185                 190

Glu His Gly Asp Ser Glu Val Pro Leu Trp Ser Ser Thr Glu Ile Gly
        195                 200                 205

Gly Val Pro Ile Thr Gln Trp Gly Thr Thr Leu Asp Gly Gly Val Phe
    210                 215                 220

Asp Glu Ser Lys Arg Glu Arg Ile Ala His Asp Val Val Arg Ser Ala
225                 230                 235                 240

Tyr Arg Ile Ile Glu Gly Lys Gly Ala Thr Asn Tyr Ala Val Gly Leu
                245                 250                 255

Ala Val Gln Arg Ile Ile Gly Ala Val Leu Asn Asp Glu Gln Arg Val
            260                 265                 270

```
Leu Thr Ile Ser Pro Leu Leu Asp Asn Trp His Gly Ile Ser Asp Val
            275                 280                 285

Cys Met Ala Val Pro Thr Ile Val Gly Arg Glu Gly Ala Gly Arg Arg
    290                 295                 300

Leu Glu Leu Pro Leu Thr Pro Glu Glu Lys Glu Arg Leu Thr Ala Ser
305                 310                 315                 320

Ala Asp His Leu Arg Glu Val Ala Arg Gly Leu Gly Tyr
                325                 330

<210> SEQ ID NO 29
<211> LENGTH: 945
<212> TYPE: DNA
<213> ORGANISM: Artificial
<220> FEATURE:
<223> OTHER INFORMATION: Synthetic construct (Bacillus anthracis LDH)
<220> FEATURE:
<221> NAME/KEY: CDS
<222> LOCATION: (1)..(945)

<400> SEQUENCE: 29 atg aaa aag ggc atc aac cga gtg gtc ctg gtc ggt acc gga gcc gtg      48
Met Lys Lys Gly Ile Asn Arg Val Val Leu Val Gly Thr Gly Ala Val
1               5                   10                  15 ggg tgc tcc tat gct tac tca atg atc aac cag ggc gtg gcc gag gaa      96
Gly Cys Ser Tyr Ala Tyr Ser Met Ile Asn Gln Gly Val Ala Glu Glu
            20                  25                  30 ttc gtg ctg gtc gac gtc aac gaa gcc aag gcc gag ggt gag gca atg     144
Phe Val Leu Val Asp Val Asn Glu Ala Lys Ala Glu Gly Glu Ala Met
        35                  40                  45 gac ctg tcc cac gcg gtc ccg ttc tcg ccc agc ccc acc aag gtg tgg     192
Asp Leu Ser His Ala Val Pro Phe Ser Pro Ser Pro Thr Lys Val Trp
    50                  55                  60 agc ggc agc tac gcg gac tgc aaa gac gcc gat ctg gtg gtc atc acc     240
Ser Gly Ser Tyr Ala Asp Cys Lys Asp Ala Asp Leu Val Val Ile Thr
65                  70                  75                  80 gcc gga ctc cct cag aag ccg ggt gaa acc cgc ttg gac ctg gtc gag     288
Ala Gly Leu Pro Gln Lys Pro Gly Glu Thr Arg Leu Asp Leu Val Glu
                85                  90                  95 aag aac acg aag atc ttc aaa cag atc gtg agg gga atc atg gat tcc     336
Lys Asn Thr Lys Ile Phe Lys Gln Ile Val Arg Gly Ile Met Asp Ser
            100                 105                 110 ggc ttt gac ggc atc ttc ctc atc gcg acg aac ccc gtg gat atc ttg     384
Gly Phe Asp Gly Ile Phe Leu Ile Ala Thr Asn Pro Val Asp Ile Leu
        115                 120                 125 acc tat gtc acc tgg aag gaa tcc ggc ctc ccg aaa gag cgc gtc att     432
Thr Tyr Val Thr Trp Lys Glu Ser Gly Leu Pro Lys Glu Arg Val Ile
    130                 135                 140 ggc agt ggg acc acg ctg gac agc gct cgc ttc cgg tat atg ctg ggc     480
Gly Ser Gly Thr Thr Leu Asp Ser Ala Arg Phe Arg Tyr Met Leu Gly
145                 150                 155                 160 gac tac ctg gac gtg gac ccg cgg aac gtc cat gcc tac atc gta ggt     528
Asp Tyr Leu Asp Val Asp Pro Arg Asn Val His Ala Tyr Ile Val Gly
                165                 170                 175 gaa cat ggc gat acc gag ctg ccc gtt tgg tcg cac gcg acg atc ggc     576
Glu His Gly Asp Thr Glu Leu Pro Val Trp Ser His Ala Thr Ile Gly
            180                 185                 190 gtg cag aag ctg gaa aca atc ctc gcc aac aat gaa cag tac aag caa     624
Val Gln Lys Leu Glu Thr Ile Leu Ala Asn Asn Glu Gln Tyr Lys Gln
        195                 200                 205 gag gat ctc gat aag att ttc gaa aac gtc cgg gac gcg gcc tac cat     672
Glu Asp Leu Asp Lys Ile Phe Glu Asn Val Arg Asp Ala Ala Tyr His
```

```
                210                 215                 220
atc atc gag cgc aaa ggg gcc acc tat tac ggc atc ggg atg tcg ctc       720
Ile Ile Glu Arg Lys Gly Ala Thr Tyr Tyr Gly Ile Gly Met Ser Leu
225                 230                 235                 240 ctg cgg gtg acc aag gca ata ctg aat aat gag aat agc gtg ctg act       768
Leu Arg Val Thr Lys Ala Ile Leu Asn Asn Glu Asn Ser Val Leu Thr
                245                 250                 255 gtc tct gcg tac ctt gag ggc cag tat ggc gag aaa gac gcg tac gtg       816
Val Ser Ala Tyr Leu Glu Gly Gln Tyr Gly Glu Lys Asp Ala Tyr Val
            260                 265                 270 ggc gta ccg gcc gtt atc aac cgc gag ggc gtc cgt gaa atc gtc gaa       864
Gly Val Pro Ala Val Ile Asn Arg Glu Gly Val Arg Glu Ile Val Glu
        275                 280                 285 ctg gag ttg aac gaa gag gaa aag gcc aag ttc gcc cac tcg gtg aag       912
Leu Glu Leu Asn Glu Glu Glu Lys Ala Lys Phe Ala His Ser Val Lys
    290                 295                 300 gtc ctc aag gaa acg atg gcg cca gtg ctg taa                           945
Val Leu Lys Glu Thr Met Ala Pro Val Leu
305                 310

<210> SEQ ID NO 30
<211> LENGTH: 314
<212> TYPE: PRT
<213> ORGANISM: Artificial
<220> FEATURE:
<223> OTHER INFORMATION: Synthetic Construct

<400> SEQUENCE: 30

Met Lys Lys Gly Ile Asn Arg Val Val Leu Val Gly Thr Gly Ala Val
1               5                   10                  15

Gly Cys Ser Tyr Ala Tyr Ser Met Ile Asn Gln Gly Val Ala Glu Glu
            20                  25                  30

Phe Val Leu Val Asp Val Asn Glu Ala Lys Ala Glu Gly Glu Ala Met
        35                  40                  45

Asp Leu Ser His Ala Val Pro Phe Ser Pro Ser Pro Thr Lys Val Trp
    50                  55                  60

Ser Gly Ser Tyr Ala Asp Cys Lys Asp Ala Asp Leu Val Val Ile Thr
65                  70                  75                  80

Ala Gly Leu Pro Gln Lys Pro Gly Glu Thr Arg Leu Asp Leu Val Glu
                85                  90                  95

Lys Asn Thr Lys Ile Phe Lys Gln Ile Val Arg Gly Ile Met Asp Ser
            100                 105                 110

Gly Phe Asp Gly Ile Phe Leu Ile Ala Thr Asn Pro Val Asp Ile Leu
        115                 120                 125

Thr Tyr Val Thr Trp Lys Glu Ser Gly Leu Pro Lys Glu Arg Val Ile
    130                 135                 140

Gly Ser Gly Thr Thr Leu Asp Ser Ala Arg Phe Arg Tyr Met Leu Gly
145                 150                 155                 160

Asp Tyr Leu Asp Val Asp Pro Arg Asn Val His Ala Tyr Ile Val Gly
                165                 170                 175

Glu His Gly Asp Thr Glu Leu Pro Val Trp Ser His Ala Thr Ile Gly
            180                 185                 190

Val Gln Lys Leu Glu Thr Ile Leu Ala Asn Asn Glu Gln Tyr Lys Gln
        195                 200                 205

Glu Asp Leu Asp Lys Ile Phe Glu Asn Val Arg Asp Ala Ala Tyr His
    210                 215                 220

Ile Ile Glu Arg Lys Gly Ala Thr Tyr Tyr Gly Ile Gly Met Ser Leu
```

```
                225                 230                 235                 240
Leu Arg Val Thr Lys Ala Ile Leu Asn Asn Glu Asn Ser Val Leu Thr
                245                 250                 255

Val Ser Ala Tyr Leu Glu Gly Gln Tyr Gly Glu Lys Asp Ala Tyr Val
            260                 265                 270

Gly Val Pro Ala Val Ile Asn Arg Glu Gly Val Arg Glu Ile Val Glu
        275                 280                 285

Leu Glu Leu Asn Glu Glu Lys Ala Lys Phe Ala His Ser Val Lys
    290                 295                 300

Val Leu Lys Glu Thr Met Ala Pro Val Leu
305                 310

<210> SEQ ID NO 31
<211> LENGTH: 957
<212> TYPE: DNA
<213> ORGANISM: Artificial
<220> FEATURE:
<223> OTHER INFORMATION: Synthetic construct (Ruminococcus torques LDH)
<220> FEATURE:
<221> NAME/KEY: CDS
<222> LOCATION: (1)..(957)

<400> SEQUENCE: 31
```

| | | | | | | | | | | | | | | | | |
|---|---|---|---|---|---|---|---|---|---|---|---|---|---|---|---|---|
| atg | aag | aaa | aaa | gtg | atc | aac | tcg | aag | aaa | gcc | gtg | atg | atc | ggg | tgc | 48 |
| Met | Lys | Lys | Lys | Val | Ile | Asn | Ser | Lys | Lys | Ala | Val | Met | Ile | Gly | Cys | |
| 1 | | | | 5 | | | | | 10 | | | | | 15 | | |
| ggc | ttt | gtg | ggt | agc | gcg | tcg | gtg | ttc | gca | ctg | atg | cag | agt | ggc | ctg | 96 |
| Gly | Phe | Val | Gly | Ser | Ala | Ser | Val | Phe | Ala | Leu | Met | Gln | Ser | Gly | Leu | |
| | | | 20 | | | | | 25 | | | | | 30 | | | |
| ttc | acc | gag | atc | gtc | ctc | atc | gac | gct | gac | aag | aat | aag | gcc | gaa | ggc | 144 |
| Phe | Thr | Glu | Ile | Val | Leu | Ile | Asp | Ala | Asp | Lys | Asn | Lys | Ala | Glu | Gly | |
| | | 35 | | | | | 40 | | | | | 45 | | | | |
| gag | gcc | atg | gat | atc | tcg | cac | ggt | att | ccg | ttc | gcg | tcc | cct | atg | aag | 192 |
| Glu | Ala | Met | Asp | Ile | Ser | His | Gly | Ile | Pro | Phe | Ala | Ser | Pro | Met | Lys | |
| | 50 | | | | | 55 | | | | | 60 | | | | | |
| atc | tat | gcg | ggc | gac | tac | gat | gat | gtc | gcc | gat | gcg | gca | atc | gtt | gtg | 240 |
| Ile | Tyr | Ala | Gly | Asp | Tyr | Asp | Asp | Val | Ala | Asp | Ala | Ala | Ile | Val | Val | |
| 65 | | | | | 70 | | | | | 75 | | | | | 80 | |
| atc | tcc | gcc | gga | gcc | ggc | cag | aaa | ccc | ggc | gag | act | cgg | ctg | gac | ctg | 288 |
| Ile | Ser | Ala | Gly | Ala | Gly | Gln | Lys | Pro | Gly | Glu | Thr | Arg | Leu | Asp | Leu | |
| | | | | 85 | | | | | 90 | | | | | 95 | | |
| gtc | aac | aaa | aac | gtc | gcg | atc | ttc | aag | tcg | atc | att | ccg | gag | att | gcg | 336 |
| Val | Asn | Lys | Asn | Val | Ala | Ile | Phe | Lys | Ser | Ile | Ile | Pro | Glu | Ile | Ala | |
| | | | 100 | | | | | 105 | | | | | 110 | | | |
| aag | cgc | aac | ttc | gcc | ggt | atc | atg | ctg | gtc | gtc | gcc | aac | ccg | gtc | gat | 384 |
| Lys | Arg | Asn | Phe | Ala | Gly | Ile | Met | Leu | Val | Val | Ala | Asn | Pro | Val | Asp | |
| | | 115 | | | | | 120 | | | | | 125 | | | | |
| atc | ctg | acc | caa | gtg | gcc | atc | aag | ttg | tcc | ggg | ctg | ccc | gag | aac | cgc | 432 |
| Ile | Leu | Thr | Gln | Val | Ala | Ile | Lys | Leu | Ser | Gly | Leu | Pro | Glu | Asn | Arg | |
| | 130 | | | | | 135 | | | | | 140 | | | | | |
| gtc | atc | ggc | tcg | ggc | acg | gtg | ctc | gac | agt | gcg | cgg | ctg | agg | tac | aag | 480 |
| Val | Ile | Gly | Ser | Gly | Thr | Val | Leu | Asp | Ser | Ala | Arg | Leu | Arg | Tyr | Lys | |
| 145 | | | | | 150 | | | | | 155 | | | | | 160 | |
| ttg | ggg | gaa | cat | ctc | tcc | gtc | gac | tcc | cgg | agc | gtg | cat | gcc | ttc | atc | 528 |
| Leu | Gly | Glu | His | Leu | Ser | Val | Asp | Ser | Arg | Ser | Val | His | Ala | Phe | Ile | |
| | | | | 165 | | | | | 170 | | | | | 175 | | |
| gtc | ggc | gaa | cac | ggg | gac | tcc | gaa | gtc | gtg | gct | tgg | agc | agc | gcg | aat | 576 |
| Val | Gly | Glu | His | Gly | Asp | Ser | Glu | Val | Val | Ala | Trp | Ser | Ser | Ala | Asn | |
| | | | 180 | | | | | 185 | | | | | 190 | | | |
| gtg | tcg | gga | gtg | ccg | ctg | agc | gaa | atg | tgc | gag | atg | cgt | ggc | cac | tac | 624 |

```
Val Ser Gly Val Pro Leu Ser Glu Met Cys Glu Met Arg Gly His Tyr
            195                 200                 205 aag cat aag gaa aac acg gcc gaa atc gcc acc gcg gta aag aat tct    672
Lys His Lys Glu Asn Thr Ala Glu Ile Ala Thr Ala Val Lys Asn Ser
210                 215                 220 gcg tac gag ata atc aac aag aag cac gcc acc tac tat ggc atc gca    720
Ala Tyr Glu Ile Ile Asn Lys Lys His Ala Thr Tyr Tyr Gly Ile Ala
225                 230                 235                 240 atg agc gtt aaa cgc atc tgt gag gtc atc atg cgc gat gag aag tcg    768
Met Ser Val Lys Arg Ile Cys Glu Val Ile Met Arg Asp Glu Lys Ser
            245                 250                 255 atc ctt ccc gta tcc cac atg att cat ggc gtc tat gac atc gac ggc    816
Ile Leu Pro Val Ser His Met Ile His Gly Val Tyr Asp Ile Asp Gly
            260                 265                 270 gtg agc ctc tca atg cca gcc atc gtg ggt gcc gac ggc atc gag agc    864
Val Ser Leu Ser Met Pro Ala Ile Val Gly Ala Asp Gly Ile Glu Ser
            275                 280                 285 gac atc ccg ata aac ctc agc gga gaa gaa gcg ctg aag ctg aaa gag    912
Asp Ile Pro Ile Asn Leu Ser Gly Glu Glu Ala Leu Lys Leu Lys Glu
            290                 295                 300 tcc gcc gac tcg ctg aag aaa atc atc gaa acc atc gaa ctg taa       957
Ser Ala Asp Ser Leu Lys Lys Ile Ile Glu Thr Ile Glu Leu
305                 310                 315
```

<210> SEQ ID NO 32
<211> LENGTH: 318
<212> TYPE: PRT
<213> ORGANISM: Artificial
<220> FEATURE:
<223> OTHER INFORMATION: Synthetic Construct

<400> SEQUENCE: 32

```
Met Lys Lys Val Ile Asn Ser Lys Lys Ala Val Met Ile Gly Cys
1               5                   10                  15

Gly Phe Val Gly Ser Ala Ser Val Phe Ala Leu Met Gln Ser Gly Leu
                20                  25                  30

Phe Thr Glu Ile Val Leu Ile Asp Ala Asp Lys Asn Lys Ala Glu Gly
            35                  40                  45

Glu Ala Met Asp Ile Ser His Gly Ile Pro Phe Ala Ser Pro Met Lys
    50                  55                  60

Ile Tyr Ala Gly Asp Tyr Asp Val Ala Asp Ala Ala Ile Val Val
65                  70                  75                  80

Ile Ser Ala Gly Ala Gly Gln Lys Pro Gly Glu Thr Arg Leu Asp Leu
                85                  90                  95

Val Asn Lys Asn Val Ala Ile Phe Lys Ser Ile Ile Pro Glu Ile Ala
            100                 105                 110

Lys Arg Asn Phe Ala Gly Ile Met Leu Val Val Ala Asn Pro Val Asp
        115                 120                 125

Ile Leu Thr Gln Val Ala Ile Lys Leu Ser Gly Leu Pro Glu Asn Arg
    130                 135                 140

Val Ile Gly Ser Gly Thr Val Leu Asp Ser Ala Arg Leu Arg Tyr Lys
145                 150                 155                 160

Leu Gly Glu His Leu Ser Val Asp Ser Arg Ser Val His Ala Phe Ile
                165                 170                 175

Val Gly Glu His Gly Asp Ser Glu Val Val Ala Trp Ser Ser Ala Asn
            180                 185                 190

Val Ser Gly Val Pro Leu Ser Glu Met Cys Glu Met Arg Gly His Tyr
        195                 200                 205
```

Lys His Lys Glu Asn Thr Ala Glu Ile Ala Thr Ala Val Lys Asn Ser
            210                 215                 220

Ala Tyr Glu Ile Ile Asn Lys Lys His Ala Thr Tyr Tyr Gly Ile Ala
225                 230                 235                 240

Met Ser Val Lys Arg Ile Cys Glu Val Ile Met Arg Asp Glu Lys Ser
                245                 250                 255

Ile Leu Pro Val Ser His Met Ile His Gly Val Tyr Asp Ile Asp Gly
            260                 265                 270

Val Ser Leu Ser Met Pro Ala Ile Val Gly Ala Asp Gly Ile Glu Ser
        275                 280                 285

Asp Ile Pro Ile Asn Leu Ser Gly Glu Glu Ala Leu Lys Leu Lys Glu
    290                 295                 300

Ser Ala Asp Ser Leu Lys Lys Ile Ile Glu Thr Ile Glu Leu
305                 310                 315

<210> SEQ ID NO 33
<211> LENGTH: 942
<212> TYPE: DNA
<213> ORGANISM: Artificial
<220> FEATURE:
<223> OTHER INFORMATION: Synthetic construct (Listeria marthii LDH)
<220> FEATURE:
<221> NAME/KEY: CDS
<222> LOCATION: (1)..(942)

<400> SEQUENCE: 33

```
atg aag gat cat cag aag atc atc ctg gta ggc gat ggt gcc gtg gga      48
Met Lys Asp His Gln Lys Ile Ile Leu Val Gly Asp Gly Ala Val Gly
1               5                   10                  15 tcc tcc tac gcc ttc gcc tgc gtc aac ctt tcg att ggc cag gaa ttc      96
Ser Ser Tyr Ala Phe Ala Cys Val Asn Leu Ser Ile Gly Gln Glu Phe
            20                  25                  30 ggc att atc gac atc gac aag gat agg aca atc ggt gac gcg atg gac     144
Gly Ile Ile Asp Ile Asp Lys Asp Arg Thr Ile Gly Asp Ala Met Asp
        35                  40                  45 ctc tcc cat gcc gtg ccc ttc tct acc ccg aaa aag atc tac tcc gcg     192
Leu Ser His Ala Val Pro Phe Ser Thr Pro Lys Lys Ile Tyr Ser Ala
    50                  55                  60 aac tat tcg gac tgc cac gac gcg gat ctg gtg gtc gtc acg gct ggg     240
Asn Tyr Ser Asp Cys His Asp Ala Asp Leu Val Val Val Thr Ala Gly
65                  70                  75                  80 acc gcc cag aag cct ggc gaa acg cgc ctg gac ttg gtt aac cgc aat     288
Thr Ala Gln Lys Pro Gly Glu Thr Arg Leu Asp Leu Val Asn Arg Asn
                85                  90                  95 atc aag atc atg aag ggc ata gtg gac gaa gtc atg gcg agc ggt ttt     336
Ile Lys Ile Met Lys Gly Ile Val Asp Glu Val Met Ala Ser Gly Phe
            100                 105                 110 gac ggc atc ttc ctg atc gcg agc aac ccc gtg gac atc ctg acc tac     384
Asp Gly Ile Phe Leu Ile Ala Ser Asn Pro Val Asp Ile Leu Thr Tyr
        115                 120                 125 gcg acc tgg aag ttc agc ggg ctc ccc aaa gag cgg gtc atc ggc tcg     432
Ala Thr Trp Lys Phe Ser Gly Leu Pro Lys Glu Arg Val Ile Gly Ser
    130                 135                 140 gga acc tca ctc gat acc gca cgc ttc cgg atg agt atc gcc gac tac     480
Gly Thr Ser Leu Asp Thr Ala Arg Phe Arg Met Ser Ile Ala Asp Tyr
145                 150                 155                 160 ctg aag gtc gat gcg cgg aat gtt cac ggc tac atc ctg ggg gag cac     528
Leu Lys Val Asp Ala Arg Asn Val His Gly Tyr Ile Leu Gly Glu His
                165                 170                 175
```

```
ggg gat acg gaa ttc ccg gcc tgg agc cac acc act gtc ggc ggc ttg    576
Gly Asp Thr Glu Phe Pro Ala Trp Ser His Thr Thr Val Gly Gly Leu
            180                 185                 190 ccg atc acc gag tgg atc tcg gaa gat gaa cag ggc gcc atg gac acg    624
Pro Ile Thr Glu Trp Ile Ser Glu Asp Glu Gln Gly Ala Met Asp Thr
            195                 200                 205 atc ttc gtg tcc gtg cgt gat gcc gcc tac gag atc atc aac aaa aag    672
Ile Phe Val Ser Val Arg Asp Ala Ala Tyr Glu Ile Ile Asn Lys Lys
            210                 215                 220 gga gcc acc ttc tat ggc gtc gcg gca gcc ctc gcc cgc atc acg aag    720
Gly Ala Thr Phe Tyr Gly Val Ala Ala Ala Leu Ala Arg Ile Thr Lys
225                 230                 235                 240 gcc att ctg aat aac gag aac gcg atc ctg ccg ctg tcg gtc tac ctg    768
Ala Ile Leu Asn Asn Glu Asn Ala Ile Leu Pro Leu Ser Val Tyr Leu
                245                 250                 255 gac ggc cat tat ggc atg aac gac atc tat atc ggc gct ccg gcg gtc    816
Asp Gly His Tyr Gly Met Asn Asp Ile Tyr Ile Gly Ala Pro Ala Val
            260                 265                 270 gtg aat cgg cag ggt gtg cga cac atc gtg gag atg aac ctc acc gac    864
Val Asn Arg Gln Gly Val Arg His Ile Val Glu Met Asn Leu Thr Asp
            275                 280                 285 aaa gaa aag gaa cag atg aag aac agc gcg gac acc ctg aaa aag gtc    912
Lys Glu Lys Glu Gln Met Lys Asn Ser Ala Asp Thr Leu Lys Lys Val
            290                 295                 300 ctg gac gac gcc atg aaa caa gtg gac taa                            942
Leu Asp Asp Ala Met Lys Gln Val Asp
305                 310

<210> SEQ ID NO 34
<211> LENGTH: 313
<212> TYPE: PRT
<213> ORGANISM: Artificial
<220> FEATURE:
<223> OTHER INFORMATION: Synthetic Construct

<400> SEQUENCE: 34

Met Lys Asp His Gln Lys Ile Ile Leu Val Gly Asp Gly Ala Val Gly
1               5                   10                  15

Ser Ser Tyr Ala Phe Ala Cys Val Asn Leu Ser Ile Gly Gln Glu Phe
            20                  25                  30

Gly Ile Ile Asp Ile Asp Lys Asp Arg Thr Ile Gly Asp Ala Met Asp
        35                  40                  45

Leu Ser His Ala Val Pro Phe Ser Thr Pro Lys Lys Ile Tyr Ser Ala
    50                  55                  60

Asn Tyr Ser Asp Cys His Asp Ala Asp Leu Val Val Thr Ala Gly
65                  70                  75                  80

Thr Ala Gln Lys Pro Gly Glu Thr Arg Leu Asp Leu Val Asn Arg Asn
                85                  90                  95

Ile Lys Ile Met Lys Gly Ile Val Asp Glu Val Met Ala Ser Gly Phe
            100                 105                 110

Asp Gly Ile Phe Leu Ile Ala Ser Asn Pro Val Asp Ile Leu Thr Tyr
        115                 120                 125

Ala Thr Trp Lys Phe Ser Gly Leu Pro Lys Glu Arg Val Ile Gly Ser
    130                 135                 140

Gly Thr Ser Leu Asp Thr Ala Arg Phe Arg Met Ser Ile Ala Asp Tyr
145                 150                 155                 160

Leu Lys Val Asp Ala Arg Asn Val His Gly Tyr Ile Leu Gly Glu His
                165                 170                 175
```

```
Gly Asp Thr Glu Phe Pro Ala Trp Ser His Thr Thr Val Gly Gly Leu
            180                 185                 190

Pro Ile Thr Glu Trp Ile Ser Glu Asp Glu Gln Gly Ala Met Asp Thr
        195                 200                 205

Ile Phe Val Ser Val Arg Asp Ala Ala Tyr Glu Ile Ile Asn Lys Lys
    210                 215                 220

Gly Ala Thr Phe Tyr Gly Val Ala Ala Leu Ala Arg Ile Thr Lys
225                 230                 235                 240

Ala Ile Leu Asn Asn Glu Asn Ala Ile Leu Pro Leu Ser Val Tyr Leu
                245                 250                 255

Asp Gly His Tyr Gly Met Asn Asp Ile Tyr Ile Gly Ala Pro Ala Val
            260                 265                 270

Val Asn Arg Gln Gly Val Arg His Ile Val Glu Met Asn Leu Thr Asp
    275                 280                 285

Lys Glu Lys Glu Gln Met Lys Asn Ser Ala Asp Thr Leu Lys Lys Val
    290                 295                 300

Leu Asp Asp Ala Met Lys Gln Val Asp
305                 310

<210> SEQ ID NO 35
<211> LENGTH: 963
<212> TYPE: DNA
<213> ORGANISM: Artificial
<220> FEATURE:
<223> OTHER INFORMATION: Synthetic construct (Bacillus subtilis LDH)
<220> FEATURE:
<221> NAME/KEY: CDS
<222> LOCATION: (1)..(963)

<400> SEQUENCE: 35 atg aac aaa cac gtg aat aaa gtg gcc ctg atc ggc gca ggc ttc gtc      48
Met Asn Lys His Val Asn Lys Val Ala Leu Ile Gly Ala Gly Phe Val
1               5                   10                  15 ggg agc tcg tac gcg ttc gcg ctg atc aac cag ggc atc acc gat gag      96
Gly Ser Ser Tyr Ala Phe Ala Leu Ile Asn Gln Gly Ile Thr Asp Glu
                20                  25                  30 ctg gta gtc atc gat gtt aac aaa gaa aag gcc atg ggg gat gtg atg     144
Leu Val Val Ile Asp Val Asn Lys Glu Lys Ala Met Gly Asp Val Met
            35                  40                  45 gac ttg aat cac ggc aag gcc ttt gcc ccg cag ccc gtc aag acg agc     192
Asp Leu Asn His Gly Lys Ala Phe Ala Pro Gln Pro Val Lys Thr Ser
        50                  55                  60 tat ggg acg tac gaa gat tgt aaa gac gcc gac atc gtg tgc atc tgc     240
Tyr Gly Thr Tyr Glu Asp Cys Lys Asp Ala Asp Ile Val Cys Ile Cys
65                  70                  75                  80 gct ggc gcc aat cag aag ccg gga gag act cgc ctg gag ctg gtc gag     288
Ala Gly Ala Asn Gln Lys Pro Gly Glu Thr Arg Leu Glu Leu Val Glu
                85                  90                  95 aag aac ctg aaa atc ttc aag ggc att gtg tcc gaa gtg atg gcc agc     336
Lys Asn Leu Lys Ile Phe Lys Gly Ile Val Ser Glu Val Met Ala Ser
                100                 105                 110 ggc ttc gac ggc atc ttc ctt atc gcc aca aac ccg gtc gac atc ctg     384
Gly Phe Asp Gly Ile Phe Leu Ile Ala Thr Asn Pro Val Asp Ile Leu
            115                 120                 125 acc tat gcc acc tgg aag ttc tcg ggc ctc cct aag gaa cgc gtc atc     432
Thr Tyr Ala Thr Trp Lys Phe Ser Gly Leu Pro Lys Glu Arg Val Ile
        130                 135                 140 gga tct ggc acc acg ctc gac tcg gcg cgt ttc cgc tac atg ctc tcc     480
Gly Ser Gly Thr Thr Leu Asp Ser Ala Arg Phe Arg Tyr Met Leu Ser
145                 150                 155                 160
```

```
gaa tac ttc ggc gct gcg ccc caa aac gtc cat gcc cac atc ata ggc    528
Glu Tyr Phe Gly Ala Ala Pro Gln Asn Val His Ala His Ile Ile Gly
            165                 170                 175 gag cac ggc gac acc gag ctg ccg gtc tgg tcc cac gcg aac gtg ggt    576
Glu His Gly Asp Thr Glu Leu Pro Val Trp Ser His Ala Asn Val Gly
        180                 185                 190 ggc gtc ccc gtg tcg gag ttg gtg gag aag aat gac gcg tat aag caa    624
Gly Val Pro Val Ser Glu Leu Val Glu Lys Asn Asp Ala Tyr Lys Gln
    195                 200                 205 gaa gaa ctg gac cag atc gtc gat gac gtg aag aac gcg gcc tac cat    672
Glu Glu Leu Asp Gln Ile Val Asp Asp Val Lys Asn Ala Ala Tyr His
210                 215                 220 atc att gag aag aaa ggc gcg acc tac tac ggt gtc gca atg tcc ctg    720
Ile Ile Glu Lys Lys Gly Ala Thr Tyr Tyr Gly Val Ala Met Ser Leu
225                 230                 235                 240 gcg cgg atc acc aag gcc atc ctg cat aac gag aat tca atc ctc acg    768
Ala Arg Ile Thr Lys Ala Ile Leu His Asn Glu Asn Ser Ile Leu Thr
            245                 250                 255 gtg agt acc tat ttg gac ggc cag tat ggg gcc gac gat gtc tac atc    816
Val Ser Thr Tyr Leu Asp Gly Gln Tyr Gly Ala Asp Asp Val Tyr Ile
        260                 265                 270 gga gtt cca gcg gta gtc aac cgg ggt ggc atc gcc ggg atc acc gaa    864
Gly Val Pro Ala Val Val Asn Arg Gly Gly Ile Ala Gly Ile Thr Glu
    275                 280                 285 ctc aac ctg aac gaa aag gaa aag gaa cag ttc ctg cac agc gcc ggt    912
Leu Asn Leu Asn Glu Lys Glu Lys Glu Gln Phe Leu His Ser Ala Gly
290                 295                 300 gtg ctg aag aac att ctg aag ccg cat ttt gcc gag cag aaa gtg aac    960
Val Leu Lys Asn Ile Leu Lys Pro His Phe Ala Glu Gln Lys Val Asn
305                 310                 315                 320 taa                                                                963
```

<210> SEQ ID NO 36
<211> LENGTH: 320
<212> TYPE: PRT
<213> ORGANISM: Artificial
<220> FEATURE:
<223> OTHER INFORMATION: Synthetic Construct

<400> SEQUENCE: 36

```
Met Asn Lys His Val Asn Lys Val Ala Leu Ile Gly Ala Gly Phe Val
1               5                   10                  15

Gly Ser Ser Tyr Ala Phe Ala Leu Ile Asn Gln Gly Ile Thr Asp Glu
            20                  25                  30

Leu Val Val Ile Asp Val Asn Lys Glu Lys Ala Met Gly Asp Val Met
        35                  40                  45

Asp Leu Asn His Gly Lys Ala Phe Ala Pro Gln Pro Val Lys Thr Ser
    50                  55                  60

Tyr Gly Thr Tyr Glu Asp Cys Lys Asp Ala Asp Ile Val Cys Ile Cys
65                  70                  75                  80

Ala Gly Ala Asn Gln Lys Pro Gly Glu Thr Arg Leu Glu Leu Val Glu
            85                  90                  95

Lys Asn Leu Lys Ile Phe Lys Gly Ile Val Ser Glu Val Met Ala Ser
        100                 105                 110

Gly Phe Asp Gly Ile Phe Leu Ile Ala Thr Asn Pro Val Asp Ile Leu
    115                 120                 125

Thr Tyr Ala Thr Trp Lys Phe Ser Gly Leu Pro Lys Glu Arg Val Ile
130                 135                 140
```

```
Gly Ser Gly Thr Thr Leu Asp Ser Ala Arg Phe Arg Tyr Met Leu Ser
145                 150                 155                 160

Glu Tyr Phe Gly Ala Ala Pro Gln Asn Val His Ala His Ile Ile Gly
                165                 170                 175

Glu His Gly Asp Thr Glu Leu Pro Val Trp Ser His Ala Asn Val Gly
            180                 185                 190

Gly Val Pro Val Ser Glu Leu Val Glu Lys Asn Asp Ala Tyr Lys Gln
        195                 200                 205

Glu Glu Leu Asp Gln Ile Val Asp Asp Val Lys Asn Ala Ala Tyr His
    210                 215                 220

Ile Ile Glu Lys Lys Gly Ala Thr Tyr Tyr Gly Val Ala Met Ser Leu
225                 230                 235                 240

Ala Arg Ile Thr Lys Ala Ile Leu His Asn Glu Asn Ser Ile Leu Thr
                245                 250                 255

Val Ser Thr Tyr Leu Asp Gly Gln Tyr Gly Ala Asp Asp Val Tyr Ile
            260                 265                 270

Gly Val Pro Ala Val Val Asn Arg Gly Gly Ile Ala Gly Ile Thr Glu
        275                 280                 285

Leu Asn Leu Asn Glu Lys Glu Lys Glu Gln Phe Leu His Ser Ala Gly
    290                 295                 300

Val Leu Lys Asn Ile Leu Lys Pro His Phe Ala Glu Gln Lys Val Asn
305                 310                 315                 320

<210> SEQ ID NO 37
<211> LENGTH: 945
<212> TYPE: DNA
<213> ORGANISM: Artificial
<220> FEATURE:
<223> OTHER INFORMATION: Synthetic construct (Enterococcus faecium LDH)
<220> FEATURE:
<221> NAME/KEY: CDS
<222> LOCATION: (1)..(945)

<400> SEQUENCE: 37 atg aag aaa acg agc cgc aaa gtc gtg atc gtc ggg acc ggc ttc gtc      48
Met Lys Lys Thr Ser Arg Lys Val Val Ile Val Gly Thr Gly Phe Val
1               5                   10                  15 ggc acc tcc atc gct tac gcc atg atc aat cag ggt att tcg aac gaa      96
Gly Thr Ser Ile Ala Tyr Ala Met Ile Asn Gln Gly Ile Ser Asn Glu
            20                  25                  30 ctg gtg ctg atc gac gtg aat cag gaa aag gcc gaa ggt gag gca ctg     144
Leu Val Leu Ile Asp Val Asn Gln Glu Lys Ala Glu Gly Glu Ala Leu
        35                  40                  45 gat ctg ctg gat ggc atg gcc tgg ggc gac gag aac gtg gcg gtc tgg     192
Asp Leu Leu Asp Gly Met Ala Trp Gly Asp Glu Asn Val Ala Val Trp
    50                  55                  60 agc ggt ggc tat gaa gag tgc aaa gac gcc gac att gtg gtc gtc acc     240
Ser Gly Gly Tyr Glu Glu Cys Lys Asp Ala Asp Ile Val Val Val Thr
65                  70                  75                  80 gcc ggt atc aac caa aag ccg gga cag tct agg ttg gat ctg gtc aag     288
Ala Gly Ile Asn Gln Lys Pro Gly Gln Ser Arg Leu Asp Leu Val Lys
                85                  90                  95 acg aat gcc tcc atc atg cgg cag atc gtc aaa gaa atc atg ggg tcc     336
Thr Asn Ala Ser Ile Met Arg Gln Ile Val Lys Glu Ile Met Gly Ser
            100                 105                 110 gga ttc gac ggc atc atc gtg gtg gcg tcg aac cct gta gac atc ctc     384
Gly Phe Asp Gly Ile Ile Val Val Ala Ser Asn Pro Val Asp Ile Leu
        115                 120                 125
```

```
acc tac atc gcg tgg aac gag tcc ggg ctg ccg acg agc cgg gtg atc       432
Thr Tyr Ile Ala Trp Asn Glu Ser Gly Leu Pro Thr Ser Arg Val Ile
    130                 135                 140 ggg acg ggc acg acc ctg gac acc acc cgg ttc cgg aag gaa atc gcg       480
Gly Thr Gly Thr Thr Leu Asp Thr Thr Arg Phe Arg Lys Glu Ile Ala
145                 150                 155                 160 ctc aag ctc aag gtc gac ccc cgc tcg gtc cat ggc tat atc ctg ggc       528
Leu Lys Leu Lys Val Asp Pro Arg Ser Val His Gly Tyr Ile Leu Gly
                165                 170                 175 gag cat ggc gac agc gaa gtg gcg gcc tgg agc cac aca acg gtg ggc       576
Glu His Gly Asp Ser Glu Val Ala Ala Trp Ser His Thr Thr Val Gly
            180                 185                 190 ggc aag ccc gtc ttt gag atc gtt gaa aag gac cac cgt atc gcg aaa       624
Gly Lys Pro Val Phe Glu Ile Val Glu Lys Asp His Arg Ile Ala Lys
        195                 200                 205 gac gag ttg gat gtc ata gcc gat aag gtc cgc aac gcg gcc tat gaa       672
Asp Glu Leu Asp Val Ile Ala Asp Lys Val Arg Asn Ala Ala Tyr Glu
    210                 215                 220 atc atc gac cgc aag aaa gcc acc tac tac ggg atc ggc atg tcg acc       720
Ile Ile Asp Arg Lys Lys Ala Thr Tyr Tyr Gly Ile Gly Met Ser Thr
225                 230                 235                 240 gcg cgg atc gtg aag gcc ata ctg aat aac gaa cag gcc gtg ctg ccg       768
Ala Arg Ile Val Lys Ala Ile Leu Asn Asn Glu Gln Ala Val Leu Pro
                245                 250                 255 gtt tca gct tac ctg acc gga gag tac aac gag aaa gac atc ttc acc       816
Val Ser Ala Tyr Leu Thr Gly Glu Tyr Asn Glu Lys Asp Ile Phe Thr
            260                 265                 270 ggc gtt ccg tcg atc gtg gat gag aac ggc gtg cga gaa gtc gtg gag       864
Gly Val Pro Ser Ile Val Asp Glu Asn Gly Val Arg Glu Val Val Glu
        275                 280                 285 ctc agt att aac gaa gaa gag aaa gcg atg ttc tcc aag agc acc tcc       912
Leu Ser Ile Asn Glu Glu Glu Lys Ala Met Phe Ser Lys Ser Thr Ser
    290                 295                 300 gca ctt cgc gag gta ctg aac act gtc ctc taa                           945
Ala Leu Arg Glu Val Leu Asn Thr Val Leu
305                 310
```

<210> SEQ ID NO 38
<211> LENGTH: 314
<212> TYPE: PRT
<213> ORGANISM: Artificial
<220> FEATURE:
<223> OTHER INFORMATION: Synthetic Construct

<400> SEQUENCE: 38

```
Met Lys Lys Thr Ser Arg Lys Val Val Ile Val Gly Thr Gly Phe Val
1               5                   10                  15

Gly Thr Ser Ile Ala Tyr Ala Met Ile Asn Gln Gly Ile Ser Asn Glu
            20                  25                  30

Leu Val Leu Ile Asp Val Asn Gln Glu Lys Ala Glu Gly Glu Ala Leu
        35                  40                  45

Asp Leu Leu Asp Gly Met Ala Trp Gly Asp Glu Asn Val Ala Val Trp
    50                  55                  60

Ser Gly Gly Tyr Glu Glu Cys Lys Asp Ala Asp Ile Val Val Val Thr
65                  70                  75                  80

Ala Gly Ile Asn Gln Lys Pro Gly Gln Ser Arg Leu Asp Leu Val Lys
                85                  90                  95

Thr Asn Ala Ser Ile Met Arg Gln Ile Val Lys Glu Ile Met Gly Ser
            100                 105                 110
```

-continued

```
Gly Phe Asp Gly Ile Ile Val Val Ala Ser Asn Pro Val Asp Ile Leu
            115                 120                 125
Thr Tyr Ile Ala Trp Asn Glu Ser Gly Leu Pro Thr Ser Arg Val Ile
130                 135                 140
Gly Thr Gly Thr Thr Leu Asp Thr Thr Arg Phe Arg Lys Glu Ile Ala
145                 150                 155                 160
Leu Lys Leu Lys Val Asp Pro Arg Ser Val His Gly Tyr Ile Leu Gly
                165                 170                 175
Glu His Gly Asp Ser Glu Val Ala Ala Trp Ser His Thr Thr Val Gly
            180                 185                 190
Gly Lys Pro Val Phe Glu Ile Val Glu Lys Asp His Arg Ile Ala Lys
        195                 200                 205
Asp Glu Leu Asp Val Ile Ala Asp Lys Val Arg Asn Ala Ala Tyr Glu
    210                 215                 220
Ile Ile Asp Arg Lys Lys Ala Thr Tyr Tyr Gly Ile Gly Met Ser Thr
225                 230                 235                 240
Ala Arg Ile Val Lys Ala Ile Leu Asn Asn Glu Gln Ala Val Leu Pro
                245                 250                 255
Val Ser Ala Tyr Leu Thr Gly Glu Tyr Asn Glu Lys Asp Ile Phe Thr
            260                 265                 270
Gly Val Pro Ser Ile Val Asp Glu Asn Gly Val Arg Glu Val Val Glu
        275                 280                 285
Leu Ser Ile Asn Glu Glu Glu Lys Ala Met Phe Ser Lys Ser Thr Ser
    290                 295                 300
Ala Leu Arg Glu Val Leu Asn Thr Val Leu
305                 310
```

<210> SEQ ID NO 39
<211> LENGTH: 951
<212> TYPE: DNA
<213> ORGANISM: Artificial
<220> FEATURE:
<223> OTHER INFORMATION: Synthetic construct (Bacillus thuriengensis LDH)
<220> FEATURE:
<221> NAME/KEY: CDS
<222> LOCATION: (1)..(951)

<400> SEQUENCE: 39

```
atg aaa cgg cat acc cgg aaa ata gcc atc atc ggc acg ggc ctg gtg      48
Met Lys Arg His Thr Arg Lys Ile Ala Ile Ile Gly Thr Gly Leu Val
1               5

```
            100                 105                 110
ggg  tt t  gac  ggc  atc  ttc  ctt  ctc  gcc  agt  aat  ccg  gtg  gac  atc  atc       384
Gly  Phe  Asp  Gly  Ile  Phe  Leu  Leu  Ala  Ser  Asn  Pro  Val  Asp  Ile  Ile
           115                 120                      125 acc  tat  caa  gtc  tgg  aag  ttg  tcg  ggc  ctc  ccc  agg  aat  cga  gtg  atc       432
Thr  Tyr  Gln  Val  Trp  Lys  Leu  Ser  Gly  Leu  Pro  Arg  Asn  Arg  Val  Ile
130                      135                           140 ggg  acc  ggc  acc  agc  ctg  gac  agc  tca  cgg  ctg  cgt  acc  atc  ctg  tcg       480
Gly  Thr  Gly  Thr  Ser  Leu  Asp  Ser  Ser  Arg  Leu  Arg  Thr  Ile  Leu  Ser
145                      150                           155                 160 gaa  atg  ctg  cac  gtc  gat  ccg  cgc  agc  atc  cac  ggc  tac  agc  ctc  ggc       528
Glu  Met  Leu  His  Val  Asp  Pro  Arg  Ser  Ile  His  Gly  Tyr  Ser  Leu  Gly
                     165                      170                 175 gag  cac  ggc  gac  tcg  cag  atg  gtc  gcc  tgg  agt  cac  gtc  acc  gtc  ggc       576
Glu  His  Gly  Asp  Ser  Gln  Met  Val  Ala  Trp  Ser  His  Val  Thr  Val  Gly
                180                      185                      190 gga  aag  ccc  atc  ctg  cag  atc  ctc  gaa  gaa  cag  aaa  gag  cgt  ttc  ggc       624
Gly  Lys  Pro  Ile  Leu  Gln  Ile  Leu  Glu  Glu  Gln  Lys  Glu  Arg  Phe  Gly
           195                      200                      205 gag  att  gac  ctg  gac  gag  atc  gtg  gaa  aag  act  gcc  aag  gcc  ggt  tgg       672
Glu  Ile  Asp  Leu  Asp  Glu  Ile  Val  Glu  Lys  Thr  Ala  Lys  Ala  Gly  Trp
           210                      215                      220 gag  atc  tat  aag  cgc  aag  ggg  aca  acg  tac  tat  ggc  atc  ggc  aac  tcc       720
Glu  Ile  Tyr  Lys  Arg  Lys  Gly  Thr  Thr  Tyr  Tyr  Gly  Ile  Gly  Asn  Ser
225                      230                      235                      240 ctg  gcc  tat  atc  gcg  tcg  tct  atc  ttc  aac  gac  gac  cat  cgc  gta  atc       768
Leu  Ala  Tyr  Ile  Ala  Ser  Ser  Ile  Phe  Asn  Asp  Asp  His  Arg  Val  Ile
                     245                      250                      255 gcg  gtg  agc  gcc  atc  ctg  gac  ggc  gag  tac  ggt  gaa  tac  gat  att  tgc       816
Ala  Val  Ser  Ala  Ile  Leu  Asp  Gly  Glu  Tyr  Gly  Glu  Tyr  Asp  Ile  Cys
                260                      265                      270 acc  ggc  gtg  ccg  gcc  att  atc  acc  cgg  gat  gga  ata  cgc  gaa  gtc  gtg       864
Thr  Gly  Val  Pro  Ala  Ile  Ile  Thr  Arg  Asp  Gly  Ile  Arg  Glu  Val  Val
           275                      280                      285 gag  ttg  aac  ctg  acg  gaa  gat  gaa  gag  tcc  cgg  ttc  gcg  aag  tcc  aat       912
Glu  Leu  Asn  Leu  Thr  Glu  Asp  Glu  Glu  Ser  Arg  Phe  Ala  Lys  Ser  Asn
           290                      295                      300 gac  atc  ctg  cgc  gac  tat  atg  aaa  acc  atc  ggc  tac  taa                      951
Asp  Ile  Leu  Arg  Asp  Tyr  Met  Lys  Thr  Ile  Gly  Tyr
305                      310                      315

<210> SEQ ID NO 40
<211> LENGTH: 316
<212> TYPE: PRT
<213> ORGANISM: Artificial
<220> FEATURE:
<223> OTHER INFORMATION: Synthetic Construct

<400> SEQUENCE: 40

Met  Lys  Arg  His  Thr  Arg  Lys  Ile  Ala  Ile  Ile  Gly  Thr  Gly  Leu  Val
1                 5                       10                      15

Gly  Ser  Ser  Cys  Ala  Tyr  Ser  Ile  Val  Asn  Gln  Gly  Ile  Cys  Glu  Glu
                20                      25                      30

Leu  Leu  Leu  Ile  Asp  Ile  Asn  His  Glu  Arg  Ala  Val  Gly  Glu  Ala  Met
           35                      40                      45

Asp  Leu  Ser  His  Cys  Ile  Asn  Phe  Thr  Asn  Thr  Arg  Thr  Lys  Val  Tyr
           50                      55                      60

Ala  Gly  Ser  Tyr  Glu  Asp  Cys  Lys  Asp  Met  Asp  Ile  Val  Ile  Ile  Thr
65                      70                      75                      80
```

```
Ala Gly Pro Ala Pro Lys Pro Gly Gln Ser Arg Leu Asp Thr Leu Gly
                85                  90                  95

Ala Ser Ala Lys Ile Met Glu Ser Val Val Gly Gly Val Met Glu Ser
            100                 105                 110

Gly Phe Asp Gly Ile Phe Leu Leu Ala Ser Asn Pro Val Asp Ile Ile
        115                 120                 125

Thr Tyr Gln Val Trp Lys Leu Ser Gly Leu Pro Arg Asn Arg Val Ile
    130                 135                 140

Gly Thr Gly Thr Ser Leu Asp Ser Ser Arg Leu Arg Thr Ile Leu Ser
145                 150                 155                 160

Glu Met Leu His Val Asp Pro Arg Ser Ile His Gly Tyr Ser Leu Gly
                165                 170                 175

Glu His Gly Asp Ser Gln Met Val Ala Trp Ser His Val Thr Val Gly
            180                 185                 190

Gly Lys Pro Ile Leu Gln Ile Leu Glu Glu Gln Lys Glu Arg Phe Gly
        195                 200                 205

Glu Ile Asp Leu Asp Glu Ile Val Glu Lys Thr Ala Lys Ala Gly Trp
    210                 215                 220

Glu Ile Tyr Lys Arg Lys Gly Thr Thr Tyr Tyr Gly Ile Gly Asn Ser
225                 230                 235                 240

Leu Ala Tyr Ile Ala Ser Ser Ile Phe Asn Asp Asp His Arg Val Ile
                245                 250                 255

Ala Val Ser Ala Ile Leu Asp Gly Glu Tyr Gly Glu Tyr Asp Ile Cys
            260                 265                 270

Thr Gly Val Pro Ala Ile Ile Thr Arg Asp Gly Ile Arg Glu Val Val
        275                 280                 285

Glu Leu Asn Leu Thr Glu Asp Glu Ser Arg Phe Ala Lys Ser Asn
    290                 295                 300

Asp Ile Leu Arg Asp Tyr Met Lys Thr Ile Gly Tyr
305                 310                 315

<210> SEQ ID NO 41
<211> LENGTH: 954
<212> TYPE: DNA
<213> ORGANISM: Artificial
<220> FEATURE:
<223> OTHER INFORMATION: Synthetic construct (Geobacillus
      stearothermophilus LDH)
<220> FEATURE:
<221> NAME/KEY: CDS
<222> LOCATION: (1)..(954)

<400> SEQUENCE: 41 atg aag aat aat ggt ggc gca agg gta gtg gta atc gga gcg ggg ttt      48
Met Lys Asn Asn Gly Gly Ala Arg Val Val Val Ile Gly Ala Gly Phe
1               5                   10                  15 gtg gga gcg tct tat gtg ttc gcg ctc atg aac cag ggc atc gcc gac      96
Val Gly Ala Ser Tyr Val Phe Ala Leu Met Asn Gln Gly Ile Ala Asp
            20                  25                  30 gag atc gtg ctc atc gac gcc aac gag agc aag gct atc ggc gat gcg     144
Glu Ile Val Leu Ile Asp Ala Asn Glu Ser Lys Ala Ile Gly Asp Ala
        35                  40                  45 atg gac ttc aat cat ggc aag gtc ttt gcg ccc aaa ccg gtg gat atc     192
Met Asp Phe Asn His Gly Lys Val Phe Ala Pro Lys Pro Val Asp Ile
    50                  55                  60 tgg cac ggt gac tac gat gac tgc cgg gac gcc gac ctg gtt gtc atc     240
Trp His Gly Asp Tyr Asp Asp Cys Arg Asp Ala Asp Leu Val Val Ile
65                  70                  75                  80
```

| | | |
|---|---|---|
| tgc gct ggc gct aac caa aag ccc ggg gaa acc cgg ctg gac ttg gtc<br>Cys Ala Gly Ala Asn Gln Lys Pro Gly Glu Thr Arg Leu Asp Leu Val<br>                       85                      90                    95 | 288 |
| gat aag aac atc gcg att ttc cga agc atc gtg gag tcc gtc atg gcg<br>Asp Lys Asn Ile Ala Ile Phe Arg Ser Ile Val Glu Ser Val Met Ala<br>               100                    105                  110 | 336 |
| tcg ggc ttc cag ggc ctg ttc ctg gtg gcc aca aac ccg gtc gac ata<br>Ser Gly Phe Gln Gly Leu Phe Leu Val Ala Thr Asn Pro Val Asp Ile<br>           115                    120                    125 | 384 |
| ctc acg tat gcc acc tgg aag ttc tcc gga ctg ccg cac gaa cgg gtc<br>Leu Thr Tyr Ala Thr Trp Lys Phe Ser Gly Leu Pro His Glu Arg Val<br>   130                    135                  140 | 432 |
| atc ggg agc ggt acg att ctg gac acg gca cgc ttc cgc ttc ctg ttg<br>Ile Gly Ser Gly Thr Ile Leu Asp Thr Ala Arg Phe Arg Phe Leu Leu<br>145                   150                  155                  160 | 480 |
| ggc gag tac ttc tcg gtc gcc cct cag aac gtc cat gcc tac atc atc<br>Gly Glu Tyr Phe Ser Val Ala Pro Gln Asn Val His Ala Tyr Ile Ile<br>               165                    170                  175 | 528 |
| ggc gag cac ggc gat acc gaa ctg cca gtg tgg tcg cag gcc tat atc<br>Gly Glu His Gly Asp Thr Glu Leu Pro Val Trp Ser Gln Ala Tyr Ile<br>        180                    185                  190 | 576 |
| ggc gtc atg ccc atc cgc aaa ctg gtg gag tcg aag ggc gaa gaa gcc<br>Gly Val Met Pro Ile Arg Lys Leu Val Glu Ser Lys Gly Glu Glu Ala<br>   195                    200                  205 | 624 |
| cag aaa gac ctg gaa cgc atc ttc gtc aat gtg cgc gat gca gcg tac<br>Gln Lys Asp Leu Glu Arg Ile Phe Val Asn Val Arg Asp Ala Ala Tyr<br>210                   215                  220 | 672 |
| cag atc att gaa aag aaa ggg gcc acc tat tac ggg atc gcg atg ggc<br>Gln Ile Ile Glu Lys Lys Gly Ala Thr Tyr Tyr Gly Ile Ala Met Gly<br>225                   230                  235                  240 | 720 |
| ctc gcc cgt gtc act cgg gcg atc ctc cac aac gag aac gcc atc ttg<br>Leu Ala Arg Val Thr Arg Ala Ile Leu His Asn Glu Asn Ala Ile Leu<br>               245                    250                  255 | 768 |
| acc gtc agc gcc tat ctg gac ggc ctt tac ggc gaa cgc gac gtg tac<br>Thr Val Ser Ala Tyr Leu Asp Gly Leu Tyr Gly Glu Arg Asp Val Tyr<br>            260                    265                  270 | 816 |
| atc ggc gtt ccg gcc gtg atc aat cgg aac ggt atc cgc gag gtg atc<br>Ile Gly Val Pro Ala Val Ile Asn Arg Asn Gly Ile Arg Glu Val Ile<br>       275                    280                  285 | 864 |
| gaa atc gag ctc aac gat gac gag aaa aac cgg ttc cat cac agt gcg<br>Glu Ile Glu Leu Asn Asp Asp Glu Lys Asn Arg Phe His His Ser Ala<br>   290                    295                  300 | 912 |
| gcc acc ctg aag tcc gtc ctg gcc cgt gcc ttc acc cgc taa<br>Ala Thr Leu Lys Ser Val Leu Ala Arg Ala Phe Thr Arg<br>305                   310                  315 | 954 |

<210> SEQ ID NO 42
<211> LENGTH: 317
<212> TYPE: PRT
<213> ORGANISM: Artificial
<220> FEATURE:
<223> OTHER INFORMATION: Synthetic Construct

<400> SEQUENCE: 42

Met Lys Asn Asn Gly Gly Ala Arg Val Val Ile Gly Ala Gly Phe
1               5                   10                  15

Val Gly Ala Ser Tyr Val Phe Ala Leu Met Asn Gln Gly Ile Ala Asp
                20                  25                  30

Glu Ile Val Leu Ile Asp Ala Asn Glu Ser Lys Ala Ile Gly Asp Ala
            35                  40                  45

```
Met Asp Phe Asn His Gly Lys Val Phe Ala Pro Lys Pro Val Asp Ile
    50                  55                  60

Trp His Gly Asp Tyr Asp Asp Cys Arg Asp Ala Asp Leu Val Val Ile
65                  70                  75                  80

Cys Ala Gly Ala Asn Gln Lys Pro Gly Glu Thr Arg Leu Asp Leu Val
                85                  90                  95

Asp Lys Asn Ile Ala Ile Phe Arg Ser Ile Val Glu Ser Val Met Ala
            100                 105                 110

Ser Gly Phe Gln Gly Leu Phe Leu Val Ala Thr Asn Pro Val Asp Ile
            115                 120                 125

Leu Thr Tyr Ala Thr Trp Lys Phe Ser Gly Leu Pro His Glu Arg Val
        130                 135                 140

Ile Gly Ser Gly Thr Ile Leu Asp Thr Ala Arg Phe Arg Phe Leu Leu
145                 150                 155                 160

Gly Glu Tyr Phe Ser Val Ala Pro Gln Asn Val His Ala Tyr Ile Ile
                165                 170                 175

Gly Glu His Gly Asp Thr Glu Leu Pro Val Trp Ser Gln Ala Tyr Ile
            180                 185                 190

Gly Val Met Pro Ile Arg Lys Leu Val Glu Ser Lys Gly Glu Glu Ala
        195                 200                 205

Gln Lys Asp Leu Glu Arg Ile Phe Val Asn Val Arg Asp Ala Ala Tyr
    210                 215                 220

Gln Ile Ile Glu Lys Lys Gly Ala Thr Tyr Tyr Gly Ile Ala Met Gly
225                 230                 235                 240

Leu Ala Arg Val Thr Arg Ala Ile Leu His Asn Glu Asn Ala Ile Leu
                245                 250                 255

Thr Val Ser Ala Tyr Leu Asp Gly Leu Tyr Gly Glu Arg Asp Val Tyr
            260                 265                 270

Ile Gly Val Pro Ala Val Ile Asn Arg Asn Gly Ile Arg Glu Val Ile
        275                 280                 285

Glu Ile Glu Leu Asn Asp Asp Glu Lys Asn Arg Phe His His Ser Ala
    290                 295                 300

Ala Thr Leu Lys Ser Val Leu Ala Arg Ala Phe Thr Arg
305                 310                 315

<210> SEQ ID NO 43
<211> LENGTH: 915
<212> TYPE: DNA
<213> ORGANISM: Artificial
<220> FEATURE:
<223> OTHER INFORMATION: Synthetic construct (Deinococcus radiodurans
      LDH)
<220> FEATURE:
<221> NAME/KEY: CDS
<222> LOCATION: (1)..(915)

<400> SEQUENCE: 43 atg aaa gtc ggg gta gtc ggt acg gga ttt gta ggt tca aca gca gcg      48
Met Lys Val Gly Val Val Gly Thr Gly Phe Val Gly Ser Thr Ala Ala
1               5                   10                  15 ttc gct ctt gtt ctc agg ggc agc tgc agc gaa ctg gtg ctc gtc gac      96
Phe Ala Leu Val Leu Arg Gly Ser Cys Ser Glu Leu Val Leu Val Asp
                20                  25                  30 cgc gat gaa gat cgg gcc caa gcg gaa gcc gag gac atc gcg cac gcc     144
Arg Asp Glu Asp Arg Ala Gln Ala Glu Ala Glu Asp Ile Ala His Ala
            35                  40                  45 gcc ccg gtg agt cac ggc acc cgc gtg tgg cat ggc ggc cac tcg gaa     192
Ala Pro Val Ser His Gly Thr Arg Val Trp His Gly Gly His Ser Glu
```

```
ctc gcg gac gcc cag gtc gtg att ctg acc gca ggc gcc aac cag aaa    240
Leu Ala Asp Ala Gln Val Val Ile Leu Thr Ala Gly Ala Asn Gln Lys
 65                  70                  75                  80 ccg ggc gag agc cgg ctg gac ctg ttg gag aag aac gcg gac atc ttc    288
Pro Gly Glu Ser Arg Leu Asp Leu Leu Glu Lys Asn Ala Asp Ile Phe
                 85                  90                  95 cgc gag ctc gtc ccc cag atc acc cgt gcg gct ccc gac gcg gtc ttg    336
Arg Glu Leu Val Pro Gln Ile Thr Arg Ala Ala Pro Asp Ala Val Leu
            100                 105                 110 ctc gtg acc agc aac cct gtc gat ctg ttg acc gac ctg gcc act cag    384
Leu Val Thr Ser Asn Pro Val Asp Leu Leu Thr Asp Leu Ala Thr Gln
        115                 120                 125 ctg gca ccc ggc cag ccg gtg ata ggc tcc ggc acg gtc ctc gac tct    432
Leu Ala Pro Gly Gln Pro Val Ile Gly Ser Gly Thr Val Leu Asp Ser
    130                 135                 140 gcc cgg ttc cga cat ctg atg gcc caa cac gcc ggg gtc gac gga acc    480
Ala Arg Phe Arg His Leu Met Ala Gln His Ala Gly Val Asp Gly Thr
145                 150                 155                 160 cat gca cac ggt tat gtg ctg ggc gag cac ggc gat tcc gaa gtg ctg    528
His Ala His Gly Tyr Val Leu Gly Glu His Gly Asp Ser Glu Val Leu
                165                 170                 175 gcc tgg tcg tcc gcc atg gtg gcc ggc atg cca gtg gcg gac ttc atg    576
Ala Trp Ser Ser Ala Met Val Ala Gly Met Pro Val Ala Asp Phe Met
            180                 185                 190 cag gcc cag aac ctc ccg tgg aat gaa cag gtt cgc gcg aag atc gac    624
Gln Ala Gln Asn Leu Pro Trp Asn Glu Gln Val Arg Ala Lys Ile Asp
        195                 200                 205 gaa ggc acc cgt aat gcg gcc gcg tcg atc atc gag ggc aaa cgc gcc    672
Glu Gly Thr Arg Asn Ala Ala Ala Ser Ile Ile Glu Gly Lys Arg Ala
    210                 215                 220 acc tat tac ggc atc ggt gcc gcg ctg gcc cgg atc acc gag gcc gtc    720
Thr Tyr Tyr Gly Ile Gly Ala Ala Leu Ala Arg Ile Thr Glu Ala Val
225                 230                 235                 240 ctg cgc gat cgc cgt gcc gtg ctg acc gtc agc gct ccg acg ccg gag    768
Leu Arg Asp Arg Arg Ala Val Leu Thr Val Ser Ala Pro Thr Pro Glu
                245                 250                 255 tac gga gtg agc ctg tcc ctt ccc cgg gtg gtc gga cgc cag ggc gtc    816
Tyr Gly Val Ser Leu Ser Leu Pro Arg Val Val Gly Arg Gln Gly Val
            260                 265                 270 ttg tcg acg ctc cat ccg aag ctg acg ggg gat gag cag cag aag ctg    864
Leu Ser Thr Leu His Pro Lys Leu Thr Gly Asp Glu Gln Gln Lys Leu
        275                 280                 285 gaa cag tcg gcg ggt gtc ctg cgg ggg ttc aag caa cag ctg ggg ctg    912
Glu Gln Ser Ala Gly Val Leu Arg Gly Phe Lys Gln Gln Leu Gly Leu
    290                 295                 300 taa                                                                915
```

<210> SEQ ID NO 44
<211> LENGTH: 304
<212> TYPE: PRT
<213> ORGANISM: Artificial
<220> FEATURE:
<223> OTHER INFORMATION: Synthetic Construct

<400> SEQUENCE: 44

```
Met Lys Val Gly Val Val Gly Thr Gly Phe Val Gly Ser Thr Ala Ala
1               5                   10                  15

Phe Ala Leu Val Leu Arg Gly Ser Cys Ser Glu Leu Val Leu Val Asp
            20                  25                  30
```

Arg Asp Glu Asp Arg Ala Gln Ala Glu Ala Glu Asp Ile Ala His Ala
         35                  40                  45

Ala Pro Val Ser His Gly Thr Arg Val Trp His Gly Gly His Ser Glu
 50                  55                  60

Leu Ala Asp Ala Gln Val Val Ile Leu Thr Ala Gly Ala Asn Gln Lys
 65                  70                  75                  80

Pro Gly Glu Ser Arg Leu Asp Leu Leu Glu Lys Asn Ala Asp Ile Phe
             85                  90                  95

Arg Glu Leu Val Pro Gln Ile Thr Arg Ala Ala Pro Asp Ala Val Leu
            100                 105                 110

Leu Val Thr Ser Asn Pro Val Asp Leu Leu Thr Asp Leu Ala Thr Gln
            115                 120                 125

Leu Ala Pro Gly Gln Pro Val Ile Gly Ser Gly Thr Val Leu Asp Ser
        130                 135                 140

Ala Arg Phe Arg His Leu Met Ala Gln His Ala Gly Val Asp Gly Thr
145                 150                 155                 160

His Ala His Gly Tyr Val Leu Gly Glu His Gly Asp Ser Glu Val Leu
                165                 170                 175

Ala Trp Ser Ser Ala Met Val Ala Gly Met Pro Val Ala Asp Phe Met
            180                 185                 190

Gln Ala Gln Asn Leu Pro Trp Asn Glu Gln Val Arg Ala Lys Ile Asp
        195                 200                 205

Glu Gly Thr Arg Asn Ala Ala Ala Ser Ile Ile Glu Gly Lys Arg Ala
    210                 215                 220

Thr Tyr Tyr Gly Ile Gly Ala Ala Leu Ala Arg Ile Thr Glu Ala Val
225                 230                 235                 240

Leu Arg Asp Arg Arg Ala Val Leu Thr Val Ser Ala Pro Thr Pro Glu
                245                 250                 255

Tyr Gly Val Ser Leu Ser Leu Pro Arg Val Val Gly Arg Gln Gly Val
            260                 265                 270

Leu Ser Thr Leu His Pro Lys Leu Thr Gly Asp Glu Gln Gln Lys Leu
        275                 280                 285

Glu Gln Ser Ala Gly Val Leu Arg Gly Phe Lys Gln Gln Leu Gly Leu
    290                 295                 300

<210> SEQ ID NO 45
<211> LENGTH: 948
<212> TYPE: DNA
<213> ORGANISM: Artificial
<220> FEATURE:
<223> OTHER INFORMATION: Synthetic construct (Plasmodium ovale LDH
      variant)
<220> FEATURE:
<221> NAME/KEY: CDS
<222> LOCATION: (1)..(948)

<400> SEQUENCE: 45 atg gca cct aaa ccc aaa att gta cta gtc gga agc ggc atg atc ggc      48
Met Ala Pro Lys Pro Lys Ile Val Leu Val Gly Ser Gly Met Ile Gly
  1               5                  10                  15 gga gta atg gca acc ctc atc gtc cag aag aat ctg ggc gat gtc gtc      96
Gly Val Met Ala Thr Leu Ile Val Gln Lys Asn Leu Gly Asp Val Val
             20                  25                  30 atg ttc gat atc gtc aag aac atg ccc ctc ggc aag gcc ctg gac acc     144
Met Phe Asp Ile Val Lys Asn Met Pro Leu Gly Lys Ala Leu Asp Thr
         35                  40                  45 tca cat acc aac gtg atg gcc tac tcc aac tgc cag gtg acc ggc agc     192

```
Ser His Thr Asn Val Met Ala Tyr Ser Asn Cys Gln Val Thr Gly Ser
    50                  55                  60 aat acc tac gag gac ttg aag ggt gcg gac gtg gtg gtg aca gcc ggc      240
Asn Thr Tyr Glu Asp Leu Lys Gly Ala Asp Val Val Val Thr Ala Gly
 65              70                  75                  80 ttc acg aag gct ccg ggc aag tcc gac aag gaa tgg aac cgc gac gat      288
Phe Thr Lys Ala Pro Gly Lys Ser Asp Lys Glu Trp Asn Arg Asp Asp
                 85                  90                  95 ctg ctc ccg ctg aat aac aag att atg atc gag atc ggc ggt cac atc      336
Leu Leu Pro Leu Asn Asn Lys Ile Met Ile Glu Ile Gly Gly His Ile
                100                 105                 110 aag aac tat tgt ccg aac gcg ttc atc atc gtg gtc act aac cca gcc      384
Lys Asn Tyr Cys Pro Asn Ala Phe Ile Ile Val Val Thr Asn Pro Ala
            115                 120                 125 gac gtg atg gtg cag ctg ctg cac cag cat agc ggc gtg agc aag aac      432
Asp Val Met Val Gln Leu Leu His Gln His Ser Gly Val Ser Lys Asn
        130                 135                 140 aag atc gtc ggc ctg ggt ggt gtg ctg gat acc tcc cgg ctg aag tat      480
Lys Ile Val Gly Leu Gly Gly Val Leu Asp Thr Ser Arg Leu Lys Tyr
145                 150                 155                 160 tac atc tcg cag aag ctc aat gtc tgc ccc cgt gac gtc aac gcg cac      528
Tyr Ile Ser Gln Lys Leu Asn Val Cys Pro Arg Asp Val Asn Ala His
                165                 170                 175 atc gtc ggg gcg cac ggg aac aaa atg gtc gtt ctg aag cgc tat atc      576
Ile Val Gly Ala His Gly Asn Lys Met Val Val Leu Lys Arg Tyr Ile
                180                 185                 190 acc gtg ggg ggc atc ccg ctg caa gag ttc atc aac aac aaa aag atc      624
Thr Val Gly Gly Ile Pro Leu Gln Glu Phe Ile Asn Asn Lys Lys Ile
            195                 200                 205 acc gac gcc gag ctc gat gcg ata ttc gat cgg acg gtc aat acg gcc      672
Thr Asp Ala Glu Leu Asp Ala Ile Phe Asp Arg Thr Val Asn Thr Ala
        210                 215                 220 ctt gag atc gtc aac tac cac gcc agt ccg tac gtg gct ccg gcc gcg      720
Leu Glu Ile Val Asn Tyr His Ala Ser Pro Tyr Val Ala Pro Ala Ala
225                 230                 235                 240 gcc atc atc gag atg gcc gag tcg tat ttg aaa gac ctg aaa aaa gtg      768
Ala Ile Ile Glu Met Ala Glu Ser Tyr Leu Lys Asp Leu Lys Lys Val
                245                 250                 255 ctg att tgc tcg acc ctg ttg gaa ggc cag tac ggc cat acg ggc gtg      816
Leu Ile Cys Ser Thr Leu Leu Glu Gly Gln Tyr Gly His Thr Gly Val
                260                 265                 270 ttt ggc ggg acg ccc ctg gtc ctc gga tgc aat ggc gtc gaa cag gtt      864
Phe Gly Gly Thr Pro Leu Val Leu Gly Cys Asn Gly Val Glu Gln Val
            275                 280                 285 ttc gaa ctc cag ctg aac gcg gaa gaa aag aaa atg ttc gac gac gcc      912
Phe Glu Leu Gln Leu Asn Ala Glu Glu Lys Lys Met Phe Asp Asp Ala
        290                 295                 300 atc gcc gaa acc aag cgc atg aag gcc ctg gcg taa                      948
Ile Ala Glu Thr Lys Arg Met Lys Ala Leu Ala
305                 310                 315

<210> SEQ ID NO 46
<211> LENGTH: 315
<212> TYPE: PRT
<213> ORGANISM: Artificial
<220> FEATURE:
<223> OTHER INFORMATION: Synthetic Construct

<400> SEQUENCE: 46

Met Ala Pro Lys Pro Lys Ile Val Leu Val Gly Ser Gly Met Ile Gly
 1               5                  10                  15
```

```
Gly Val Met Ala Thr Leu Ile Val Gln Lys Asn Leu Gly Asp Val Val
            20                  25                  30

Met Phe Asp Ile Val Lys Asn Met Pro Leu Gly Lys Ala Leu Asp Thr
        35                  40                  45

Ser His Thr Asn Val Met Ala Tyr Ser Asn Cys Gln Val Thr Gly Ser
    50                  55                  60

Asn Thr Tyr Glu Asp Leu Lys Gly Ala Asp Val Val Thr Ala Gly
65                  70                  75                  80

Phe Thr Lys Ala Pro Gly Lys Ser Asp Lys Glu Trp Asn Arg Asp Asp
                85                  90                  95

Leu Leu Pro Leu Asn Asn Lys Ile Met Ile Glu Ile Gly Gly His Ile
                100                 105                 110

Lys Asn Tyr Cys Pro Asn Ala Phe Ile Ile Val Val Thr Asn Pro Ala
            115                 120                 125

Asp Val Met Val Gln Leu Leu His Gln His Ser Gly Val Ser Lys Asn
130                 135                 140

Lys Ile Val Gly Leu Gly Gly Val Leu Asp Thr Ser Arg Leu Lys Tyr
145                 150                 155                 160

Tyr Ile Ser Gln Lys Leu Asn Val Cys Pro Arg Asp Val Asn Ala His
                165                 170                 175

Ile Val Gly Ala His Gly Asn Lys Met Val Val Leu Lys Arg Tyr Ile
            180                 185                 190

Thr Val Gly Gly Ile Pro Leu Gln Glu Phe Ile Asn Asn Lys Lys Ile
        195                 200                 205

Thr Asp Ala Glu Leu Asp Ala Ile Phe Asp Arg Thr Val Asn Thr Ala
210                 215                 220

Leu Glu Ile Val Asn Tyr His Ala Ser Pro Tyr Val Ala Pro Ala Ala
225                 230                 235                 240

Ala Ile Ile Glu Met Ala Glu Ser Tyr Leu Lys Asp Leu Lys Lys Val
                245                 250                 255

Leu Ile Cys Ser Thr Leu Leu Glu Gly Gln Tyr Gly His Thr Gly Val
            260                 265                 270

Phe Gly Gly Thr Pro Leu Val Leu Gly Cys Asn Gly Val Glu Gln Val
        275                 280                 285

Phe Glu Leu Gln Leu Asn Ala Glu Glu Lys Lys Met Phe Asp Asp Ala
290                 295                 300

Ile Ala Glu Thr Lys Arg Met Lys Ala Leu Ala
305                 310                 315
```

<210> SEQ ID NO 47
<211> LENGTH: 933
<212> TYPE: DNA
<213> ORGANISM: Artificial
<220> FEATURE:
<223> OTHER INFORMATION: Synthetic construct (Thermus thermophilus LDH)
<220> FEATURE:
<221> NAME/KEY: CDS
<222> LOCATION: (1)..(933)

<400> SEQUENCE: 47

```
atg aaa gta gga ata gtc ggc tct gga atg gtt gga tcg gca acg gca      48
Met Lys Val Gly Ile Val Gly Ser Gly Met Val Gly Ser Ala Thr Ala
1               5                   10                  15 tac gca ctc gca ctc ctc ggc gtg gcg cgg gaa gtc gtg ctg gtc gat      96
Tyr Ala Leu Ala Leu Leu Gly Val Ala Arg Glu Val Val Leu Val Asp
            20                  25                  30
```

```
ctc gac cgc aag ctg gcg cag gcc cat gcc gag gat atc ctg cac gcg      144
Leu Asp Arg Lys Leu Ala Gln Ala His Ala Glu Asp Ile Leu His Ala
         35                  40                  45 acc ccg ttc gcg cat ccc gtg tgg gtc cgt gcc ggc agc tat ggc gac      192
Thr Pro Phe Ala His Pro Val Trp Val Arg Ala Gly Ser Tyr Gly Asp
 50                  55                  60 ctg gaa ggg gcg aga gcg gtc gtc ctg gcg gcc ggg gtg gcc cag cgg      240
Leu Glu Gly Ala Arg Ala Val Val Leu Ala Ala Gly Val Ala Gln Arg
 65                  70                  75                  80 cca ggc gaa acc cgc ctc cag ctg ctc gat cgc aac gcc cag gtg ttt      288
Pro Gly Glu Thr Arg Leu Gln Leu Leu Asp Arg Asn Ala Gln Val Phe
             85                  90                  95 gcc caa gtg gta ccg cgg gtt ctg gaa gct gcc ccc gaa gcc gtg ttg      336
Ala Gln Val Val Pro Arg Val Leu Glu Ala Ala Pro Glu Ala Val Leu
        100                 105                 110 ctg gtc gcc acc aat ccc gtc gac gtg atg acc cag gtc gcc tac cgc      384
Leu Val Ala Thr Asn Pro Val Asp Val Met Thr Gln Val Ala Tyr Arg
            115                 120                 125 ctg agc ggt ctg ccg ccg gga agg gtc gtg ggg agc ggc acg atc ctg      432
Leu Ser Gly Leu Pro Pro Gly Arg Val Val Gly Ser Gly Thr Ile Leu
130                 135                 140 gac aca gcg cgg ttc cgg gcc ttg ctt gcc gag tat ctg cgg gtg gct      480
Asp Thr Ala Arg Phe Arg Ala Leu Leu Ala Glu Tyr Leu Arg Val Ala
145                 150                 155                 160 ccg cag tcg gtc cac gcg tac gtg ctc ggc gaa cac ggc gac tcg gaa      528
Pro Gln Ser Val His Ala Tyr Val Leu Gly Glu His Gly Asp Ser Glu
                165                 170                 175 gtc ctc gtg tgg agc tcc gcg caa gtc ggg ggt gtg ccg ctt ctg gag      576
Val Leu Val Trp Ser Ser Ala Gln Val Gly Gly Val Pro Leu Leu Glu
            180                 185                 190 ttc gcg gaa gcg cgt ggg cgt gcc cta tcg cct gag gac agg gct cgg      624
Phe Ala Glu Ala Arg Gly Arg Ala Leu Ser Pro Glu Asp Arg Ala Arg
        195                 200                 205 atc gac gag ggc gtg cga cgg gcc gcc tac cgc atc atc gag ggc aag      672
Ile Asp Glu Gly Val Arg Arg Ala Ala Tyr Arg Ile Ile Glu Gly Lys
    210                 215                 220 ggc gcg act tat tac ggc atc ggt gcc ggc ctg gcg cgt ctg gtc cgc      720
Gly Ala Thr Tyr Tyr Gly Ile Gly Ala Gly Leu Ala Arg Leu Val Arg
225                 230                 235                 240 gcg atc ttg acc gac gag aaa ggc gtc tat acg gtg tcc gcc ttc acc      768
Ala Ile Leu Thr Asp Glu Lys Gly Val Tyr Thr Val Ser Ala Phe Thr
                245                 250                 255 ccc gag gtt gag ggt gtg ctg gaa gtc agt ctg tcc ttg ccg cgc att      816
Pro Glu Val Glu Gly Val Leu Glu Val Ser Leu Ser Leu Pro Arg Ile
            260                 265                 270 ctc ggc gcc ggc ggc gtc gag ggc acc gtg tac ccg tcc ctg tca ccc      864
Leu Gly Ala Gly Gly Val Glu Gly Thr Val Tyr Pro Ser Leu Ser Pro
        275                 280                 285 gag gaa cgc gag gcc ctg cgc cgc agc gcc gaa atc ctc aag gaa gcg      912
Glu Glu Arg Glu Ala Leu Arg Arg Ser Ala Glu Ile Leu Lys Glu Ala
    290                 295                 300 gcg ttc gcc ctg ggt ttc taa                                          933
Ala Phe Ala Leu Gly Phe
305                 310

<210> SEQ ID NO 48
<211> LENGTH: 310
<212> TYPE: PRT
<213> ORGANISM: Artificial
<220> FEATURE:
<223> OTHER INFORMATION: Synthetic Construct
```

<400> SEQUENCE: 48

```
Met Lys Val Gly Ile Val Gly Ser Gly Met Val Gly Ser Ala Thr Ala
1               5                   10                  15

Tyr Ala Leu Ala Leu Leu Gly Val Ala Arg Glu Val Val Leu Val Asp
            20                  25                  30

Leu Asp Arg Lys Leu Ala Gln Ala His Ala Glu Asp Ile Leu His Ala
        35                  40                  45

Thr Pro Phe Ala His Pro Val Trp Val Arg Ala Gly Ser Tyr Gly Asp
    50                  55                  60

Leu Glu Gly Ala Arg Ala Val Val Leu Ala Ala Gly Val Ala Gln Arg
65                  70                  75                  80

Pro Gly Glu Thr Arg Leu Gln Leu Leu Asp Arg Asn Ala Gln Val Phe
                85                  90                  95

Ala Gln Val Val Pro Arg Val Leu Glu Ala Ala Pro Glu Ala Val Leu
            100                 105                 110

Leu Val Ala Thr Asn Pro Val Asp Val Met Thr Gln Val Ala Tyr Arg
        115                 120                 125

Leu Ser Gly Leu Pro Pro Gly Arg Val Val Gly Ser Gly Thr Ile Leu
    130                 135                 140

Asp Thr Ala Arg Phe Arg Ala Leu Leu Ala Glu Tyr Leu Arg Val Ala
145                 150                 155                 160

Pro Gln Ser Val His Ala Tyr Val Leu Gly Glu His Gly Asp Ser Glu
                165                 170                 175

Val Leu Val Trp Ser Ser Ala Gln Val Gly Gly Val Pro Leu Leu Glu
            180                 185                 190

Phe Ala Glu Ala Arg Gly Arg Ala Leu Ser Pro Glu Asp Arg Ala Arg
        195                 200                 205

Ile Asp Glu Gly Val Arg Arg Ala Ala Tyr Arg Ile Ile Glu Gly Lys
    210                 215                 220

Gly Ala Thr Tyr Tyr Gly Ile Gly Ala Gly Leu Ala Arg Leu Val Arg
225                 230                 235                 240

Ala Ile Leu Thr Asp Glu Lys Gly Val Tyr Thr Val Ser Ala Phe Thr
                245                 250                 255

Pro Glu Val Glu Gly Val Leu Glu Val Ser Leu Ser Leu Pro Arg Ile
            260                 265                 270

Leu Gly Ala Gly Gly Val Glu Gly Thr Val Tyr Pro Ser Leu Ser Pro
        275                 280                 285

Glu Glu Arg Glu Ala Leu Arg Arg Ser Ala Glu Ile Leu Lys Glu Ala
    290                 295                 300

Ala Phe Ala Leu Gly Phe
305                 310
```

<210> SEQ ID NO 49
<211> LENGTH: 229
<212> TYPE: DNA
<213> ORGANISM: Methanococcus capsulatus Bath MDH promoter

<400> SEQUENCE: 49

```
tttgcctcga tcggcggtcc ttgtgacagg gagatattcc cgacggatcc ggggcattcg     60
agcggaaccg cccgccgtgg gagttttttcc agcgagcatt cgagagtttt tcaaggcggc   120
ttcgaggggt tattccgtaa cgccgccgac atgatctgtc ccagaatctc cgccgctgtt   180
cgtagagcgc cgatgcaggg tcggcatcaa tcattcttgg aggagacac                229
```

<210> SEQ ID NO 50
<211> LENGTH: 114
<212> TYPE: DNA
<213> ORGANISM: Methylosinus trichosporium OB3b promoter region for sga

<400> SEQUENCE: 50 tttttttgaga ccacgcggcc cgacgcgcaa ggaagctttc gggcgcgcgc gcgtccggcg    60
aagacaactc gaaccgatga gctcgaaggg agccctagac aggaggtaaa aatg         114

<210> SEQ ID NO 51
<211> LENGTH: 707
<212> TYPE: DNA
<213> ORGANISM: Methylomonas sp. 16a maxF promoter

<400> SEQUENCE: 51
gcgccgtatg ctttcgaatc cgccaagacc gggcatggat aaatccatga ccaccacatc    60
gggcaattgc tttgaataga gttggcaagc ggtctcgcca cgatcggctt catagatctc   120
gccgatacga tccgacagcg atagataggt cttgtagccg gtacgaacca cggcgtgatc   180
atctaccaat aaaacgctga ttttactcgc cactggaaaa tttcctcctc aggtcgtcaa   240
gggataaaga tatgggacaa gtccagtctg atgccaggcg acttggtgt gcctttttt    300 atgatgacgc tttatccgtg cttaaaccat gggagctttt cccgtttcca atttcgatcc   360
ttggcgagat aggaatattt ccgtgcatga ttgcgtcgat ttcacatcga tttcatggat   420
tgttccgtaa cgttagccag cccggcttct ataacatttg cgccagcgtg gcctggtggt   480
cggtaacccg tgatgcggtt atgatcaaca aagctggttt tcaacgacta attctgatct   540
tcaggtcgcg cctcacttat agcgataaaa atcctggagg aaacatgcaa caactcgatt   600
tgcgcatagt cgggaaaacc gcggccttgt tggctggtgg ccttctgagc gtggcgcaac   660
ccgcatcggc gaacaaggag ctggaacagc tcggaggatt taaaatg               707

<210> SEQ ID NO 52
<211> LENGTH: 281
<212> TYPE: DNA
<213> ORGANISM: Methylomonas sp. 16a hps promoter

<400> SEQUENCE: 52
cagatagtaa gcgctaagga ttggggtgcg tcgccggtcg cggcggcgct cctcgacggc    60
agagttggtg ccaggttggc ggatgattga tgccgaatat tacgcgacca attctcgagg   120
caaatgaact gtgagctact gagttgcagg cattgacagc catcccatt ctatcataca   180 gttacggacg catcacgagt aggtgataag cctagcagat tgcggcagtt ggcaaaatca   240
gctattacta ataattaaaa actttcggag cacatcaaat g                      281

<210> SEQ ID NO 53
<211> LENGTH: 317
<212> TYPE: PRT
<213> ORGANISM: Staphylococcus simiae

<400> SEQUENCE: 53

Met Asn Gln Phe Lys Gly Asn Lys Val Val Leu Ile Gly Asn Gly Ala
1               5                   10                  15

Val Gly Ser Ser Tyr Ala Phe Ser Leu Val Asn Gln Ser Ile Val Asp
                20                  25                  30

Glu Leu Val Ile Ile Asp Leu Asp Thr Glu Lys Val Lys Gly Asp Val
            35                  40                  45

Met Asp Leu Lys His Ala Thr Pro Tyr Ser Pro Thr Val Arg Val
50                  55                  60

Lys Ala Gly Glu Tyr Ser Asp Cys His Asp Ala Asp Leu Val Val Ile
65                  70                  75                  80

Cys Ala Gly Ala Ala Gln Lys Pro Gly Glu Thr Arg Leu Asp Leu Val
                85                  90                  95

Ser Lys Asn Leu Lys Ile Phe Lys Ser Ile Val Asp Glu Val Met Ala
                100                 105                 110

Ser Gln Phe Asp Gly Ile Phe Leu Val Ala Thr Asn Pro Val Asp Ile
                115                 120                 125

Leu Ser Tyr Ala Thr Trp Lys Phe Ser Gly Leu Pro Lys Glu Arg Val
130                 135                 140

Ile Gly Ser Gly Thr Ile Leu Asp Ser Ala Arg Phe Arg Leu Leu Leu
145                 150                 155                 160

Ser Glu Glu Phe Asp Val Ala Pro Ser Ser Val His Ala Gln Ile Ile
                165                 170                 175

Gly Glu His Gly Asp Thr Glu Leu Ala Val Trp Ser His Ala Asn Ile
                180                 185                 190

Ala Gly Gln Pro Leu Lys Glu Ile Leu Glu Lys Arg Pro Gln Glu Lys
                195                 200                 205

Glu Lys Val Glu Gln Ile Phe Val Gln Thr Arg Asp Ala Ala Tyr Asp
210                 215                 220

Ile Ile Lys Ala Lys Gly Ala Thr Tyr Tyr Gly Val Ala Met Gly Leu
225                 230                 235                 240

Thr Arg Ile Thr Glu Ala Ile Phe Arg Asn Glu Asp Ala Val Leu Thr
                245                 250                 255

Ile Ser Ala Leu Leu Glu Gly Glu Tyr Gly Gln Glu Asp Leu Tyr Ile
                260                 265                 270

Gly Val Pro Ala Val Ile Asn Arg Gly Gly Ile Arg Asn Val Val Glu
                275                 280                 285

Thr Pro Leu Asn Glu Glu Arg Thr Gln Phe Ala His Ser Ala His
                290                 295                 300

Thr Leu Lys Asp Ile Met Ser Lys Ala Asp Glu Leu Lys
305                 310                 315

<210> SEQ ID NO 54
<211> LENGTH: 317
<212> TYPE: PRT
<213> ORGANISM: Staphylococcus vitulinus

<400> SEQUENCE: 54

Met Lys Gln Phe Lys Gly Lys Lys Val Val Leu Val Gly Asn Gly Ala
1                   5                   10                  15

Val Gly Ser Ser Tyr Ala Phe Ser Met Ile Asn Gln Gly Ile Cys Asp
                20                  25                  30

Glu Phe Val Ile Ile Asp Leu Asp Lys Lys Val Asn Gly Asp Val
                35                  40                  45

Met Asp Leu Asn His Gly Thr Val Tyr Gly Pro Ser Pro Ile Lys Val
50                  55                  60

Lys Ala Gly Glu Tyr Lys Asp Cys Asn Asp Ala Asp Leu Val Val Ile
65                  70                  75                  80

Cys Ala Gly Ala Ala Gln Lys Pro Gly Glu Thr Arg Leu Asp Leu Val
                85                  90                  95

Ala Lys Asn Met Lys Ile Phe Lys Ser Ile Val Asp Glu Ile Met Arg
                100                 105                 110

Ser Gly Phe Asp Gly Ile Phe Leu Ile Ala Thr Asn Pro Val Asp Val
        115                 120                 125

Leu Thr Tyr Ala Thr Met Lys Phe Ser Gly Leu Pro Lys Glu Arg Val
        130                 135                 140

Ile Gly Ser Gly Thr Ile Leu Asp Thr Ala Arg Phe Arg Tyr Leu Leu
145                 150                 155                 160

Ser Glu Glu Phe Asp Val Ala Pro Gln Ser Val His Ala Asn Ile Ile
        165                 170                 175

Gly Glu His Gly Asp Ser Glu Leu Pro Val Trp Ser His Ala Asn Ile
        180                 185                 190

Ala Gly Lys Pro Leu Arg Ser Ile Ile Glu Gln Asp Asp Ser Arg Lys
        195                 200                 205

His Arg Val Glu Glu Ile Phe Val Gln Thr Arg Asp Ala Ala Tyr Glu
        210                 215                 220

Ile Ile Glu Ala Lys Gly Ala Thr Tyr Tyr Gly Val Ala Met Gly Leu
225                 230                 235                 240

Met Arg Ile Thr Lys Ala Ile Leu Asn Asn Gln Asp Val Val Leu Thr
        245                 250                 255

Val Ser Ala Tyr Leu Glu Gly Glu Tyr Gly His Glu Gly Val Tyr Ile
        260                 265                 270

Gly Val Pro Ala Leu Ile Asn Arg Ser Gly Ile Lys Glu Val Ile Glu
        275                 280                 285

Ile Pro Leu Asp Glu Glu Thr Ser Leu Phe Asn His Ser Val Lys
        290                 295                 300

Val Leu Lys Asp Ile Gln Asp Pro Phe Glu Lys Glu Phe
305                 310                 315

<210> SEQ ID NO 55
<211> LENGTH: 318
<212> TYPE: PRT
<213> ORGANISM: Staphylococcus lentus

<400> SEQUENCE: 55

Met Lys Gln Phe Lys Gly Asn Lys Val Val Leu Val Gly Asn Gly Phe
1               5                   10                  15

Val Gly Ser Ser Tyr Ala Phe Ser Met Ile Asn Gln Gly Ile Cys Asp
        20                  25                  30

Glu Phe Val Ile Ile Asp Leu Asp Lys Lys Val Asn Gly Asp Val
        35                  40                  45

Met Asp Leu Asn His Gly Ser Val Tyr Gly Pro Ser Pro Met Lys Val
50                  55                  60

Lys Ala Gly Glu Tyr Lys Asp Cys Glu Asp Ala Asp Leu Val Val Ile
65                  70                  75                  80

Cys Ala Gly Ala Ala Gln Lys Pro Gly Glu Thr Arg Leu Asp Leu Val
        85                  90                  95

Ala Lys Asn Met Lys Ile Phe Lys Asn Ile Val Thr Glu Ile Met Asp
        100                 105                 110

Ser Gly Phe Asp Gly Ile Phe Leu Ile Ala Thr Asn Pro Val Asp Ile
        115                 120                 125

Leu Ser Tyr Ala Thr Met Lys Phe Ser Gly Leu Pro Lys Glu Arg Val
        130                 135                 140

Ile Gly Ser Gly Thr Ile Leu Asp Thr Ala Arg Phe Lys Tyr Leu Leu
145                 150                 155                 160

Ser Glu Glu Phe Asp Val Ala Pro Gln Ser Val His Ala Asn Ile Ile

```
              165                 170                 175
Gly Glu His Gly Asp Ser Glu Leu Ala Val Trp Ser His Ala Asn Ile
            180                 185                 190

Ala Gly Lys Pro Leu Arg Ser Ile Ile Glu Lys Asp Glu Thr Arg Lys
            195                 200                 205

His Arg Val Glu Glu Ile Phe Val Glu Thr Arg Asp Ala Ala Tyr Glu
        210                 215                 220

Ile Ile Glu Ser Lys Gly Ala Thr Phe Tyr Gly Val Ala Met Gly Leu
225                 230                 235                 240

Met Arg Ile Thr Lys Ala Ile Leu Asn Asn Gln Asp Val Val Leu Thr
                245                 250                 255

Val Ser Ala Tyr Leu Glu Gly Glu Tyr Gly His Glu Asp Val Tyr Ile
            260                 265                 270

Gly Val Pro Ala Leu Val Asn Arg Thr Gly Val Arg Glu Val Ile Glu
        275                 280                 285

Met Pro Leu Asn Asp Glu Glu Thr Arg Leu Phe Asp Asn Ser Val Lys
    290                 295                 300

Val Leu Lys Asp Ile Gln Ala Pro Phe Glu Lys Glu Phe Lys
305                 310                 315

<210> SEQ ID NO 56
<211> LENGTH: 315
<212> TYPE: PRT
<213> ORGANISM: Macrococcus caseolyticus

<400> SEQUENCE: 56

Met Glu Lys Phe Lys Gly Asn Lys Val Val Leu Val Gly Asn Gly Ala
1               5                   10                  15

Val Gly Ser Ser Tyr Ala Phe Ala Met Leu Asn Gln Gly Ala Cys Asp
            20                  25                  30

Glu Phe Val Ile Ile Asp Leu Asn Glu Asp Lys Ala Lys Gly Asp Ala
        35                  40                  45

Met Asp Leu Asn His Gly Val Val Tyr Ala Pro Ser Pro Met Gln Val
    50                  55                  60

Lys Tyr Gly Thr Tyr Glu Asp Cys His Asp Ala Ser Leu Ile Val Ile
65                  70                  75                  80

Cys Ala Gly Ala Ala Gln Lys Pro Gly Glu Thr Arg Leu Asp Leu Val
                85                  90                  95

Gly Lys Asn Met Lys Ile Phe Lys Ser Ile Val Asp Glu Ile Met Lys
            100                 105                 110

Ser Gly Phe Asp Gly Ile Phe Leu Ile Ala Thr Asn Pro Val Asp Val
        115                 120                 125

Leu Thr Tyr Ala Val Gln Lys Phe Ser Gly Leu Pro Glu Asn Gln Val
    130                 135                 140

Ile Gly Ser Gly Thr Ile Leu Asp Thr Ala Arg Phe Arg His Leu Leu
145                 150                 155                 160

Ser Gln Glu Phe Asn Val Ser Pro Asn Ser Val His Gly Tyr Ile Ile
                165                 170                 175

Gly Glu His Gly Asp Ser Glu Leu Ala Val Trp Ser Gly Thr Asn Ile
            180                 185                 190

Ala Gly Asn Ser Leu Tyr Asp Ile Leu Asn Glu Asn Pro Glu Lys Gln
            195                 200                 205

Lys Leu Ile Glu Glu Ile Phe Val Asn Thr Arg Asp Ala Ala Tyr Glu
        210                 215                 220
```

```
Ile Ile Lys Ala Lys Gly Ala Thr Tyr Tyr Gly Val Ala Met Gly Leu
225                 230                 235                 240

Met Arg Ile Ser Lys Ala Ile Leu Asn Asn Glu Asn Val Val Leu Thr
                245                 250                 255

Val Ser Ala Lys Leu Asn Gly Glu Tyr Gly His Asp Asp Val Tyr Ile
            260                 265                 270

Gly Val Pro Ala Ile Ile Asn Arg Asn Gly Ile Arg Glu Val Leu Glu
                275                 280                 285

Thr Pro Leu Asn Thr Glu Glu Lys Glu Lys Phe Ala Lys Ser Val Glu
            290                 295                 300

Thr Leu Lys Ala Ile Gln Thr Pro Phe Phe Ser
305                 310                 315
```

<210> SEQ ID NO 57
<211> LENGTH: 314
<212> TYPE: PRT
<213> ORGANISM: Bacillus thuringiensis

<400> SEQUENCE: 57

```
Met Lys Lys Gly Ile Asn Arg Val Val Leu Val Gly Thr Gly Ala Val
1               5                   10                  15

Gly Cys Ser Tyr Ala Tyr Ser Met Ile Asn Gln Gly Val Ala Glu Glu
                20                  25                  30

Phe Val Leu Val Asp Val Asn Glu Ala Lys Ala Glu Gly Glu Ala Met
            35                  40                  45

Asp Leu Ser His Ala Val Pro Phe Ser Pro Ser Pro Thr Lys Val Trp
50                  55                  60

Ser Gly Ser Tyr Ala Asp Cys Lys Asp Ala Asp Leu Val Val Ile Thr
65                  70                  75                  80

Ala Gly Leu Pro Gln Lys Pro Gly Glu Thr Arg Leu Asp Leu Val Glu
                85                  90                  95

Lys Asn Thr Lys Ile Phe Lys Gln Ile Val Arg Gly Ile Met Asp Ser
                100                 105                 110

Gly Phe Asp Gly Ile Phe Leu Ile Ala Thr Asn Pro Val Asp Ile Leu
            115                 120                 125

Thr Tyr Val Thr Trp Lys Glu Ser Gly Leu Pro Lys Glu Arg Val Ile
130                 135                 140

Gly Ser Gly Thr Thr Leu Asp Ser Ala Arg Phe Arg Tyr Met Leu Gly
145                 150                 155                 160

Asp Tyr Leu Asp Val Asp Pro Arg Asn Val His Ala Tyr Ile Val Gly
                165                 170                 175

Glu His Gly Asp Thr Glu Leu Pro Val Trp Ser His Ala Thr Ile Gly
            180                 185                 190

Val Gln Lys Leu Glu Thr Ile Leu Ala Asn Asn Glu Gln Tyr Lys Gln
        195                 200                 205

Glu Asp Leu Asp Lys Ile Phe Glu Asn Val Arg Asp Ala Ala Tyr His
210                 215                 220

Ile Ile Glu Arg Lys Gly Ala Thr Tyr Tyr Gly Ile Gly Met Ser Leu
225                 230                 235                 240

Leu Arg Val Thr Lys Ala Ile Leu Asn Asn Glu Asn Ser Val Leu Thr
                245                 250                 255

Val Ser Ala Tyr Leu Glu Gly Gln Tyr Gly Glu Lys Asp Ala Tyr Val
            260                 265                 270

Gly Val Pro Ala Val Ile Asn Arg Glu Gly Val Arg Glu Ile Val Glu
                275                 280                 285
```

Leu Glu Leu Asn Glu Glu Lys Ala Lys Phe Ala His Ser Val Lys
    290                 295                 300

Val Leu Lys Glu Thr Met Ala Pro Val Leu
305                 310

<210> SEQ ID NO 58
<211> LENGTH: 314
<212> TYPE: PRT
<213> ORGANISM: Bacillus thuringiensis

<400> SEQUENCE: 58

Met Lys Lys Gly Ile Asn Arg Val Val Leu Val Gly Thr Gly Ala Val
1               5                   10                  15

Gly Cys Ser Tyr Ala Tyr Ser Met Ile Asn Gln Gly Val Ala Glu Glu
            20                  25                  30

Phe Val Leu Val Asp Val Asn Glu Ala Lys Ala Glu Gly Glu Ala Met
        35                  40                  45

Asp Leu Ser His Ala Val Pro Phe Ser Pro Ser Thr Lys Val Trp
    50                  55                  60

Ser Gly Ser Tyr Ala Asp Cys Lys Asp Ala Asp Leu Val Val Ile Thr
65                  70                  75                  80

Ala Gly Leu Pro Gln Lys Pro Gly Glu Thr Arg Leu Asp Leu Val Glu
                85                  90                  95

Lys Asn Thr Lys Ile Phe Lys Gln Ile Val Arg Gly Ile Met Asp Ser
            100                 105                 110

Gly Phe Asp Gly Ile Phe Leu Ile Ala Thr Asn Pro Val Asp Ile Leu
        115                 120                 125

Thr Tyr Val Thr Trp Lys Glu Ser Gly Leu Pro Lys Glu Arg Val Ile
    130                 135                 140

Gly Ser Gly Thr Thr Leu Asp Ser Ala Arg Phe Arg Tyr Met Leu Gly
145                 150                 155                 160

Asp Tyr Leu Asp Val Asp Pro Arg Asn Val His Ala Tyr Ile Val Gly
                165                 170                 175

Glu His Gly Asp Thr Glu Leu Pro Val Trp Ser His Ala Thr Ile Gly
            180                 185                 190

Val Gln Lys Leu Glu Thr Ile Leu Ala Asn Asn Glu Gln Tyr Asn Gln
        195                 200                 205

Glu Asp Leu Asp Lys Ile Phe Glu Asn Val Arg Asp Ala Ala Tyr His
    210                 215                 220

Ile Ile Glu Arg Lys Gly Ala Thr Tyr Tyr Gly Ile Gly Met Ser Leu
225                 230                 235                 240

Leu Arg Val Thr Lys Ala Ile Leu Asn Asn Glu Asn Ser Val Leu Thr
                245                 250                 255

Val Ser Ala Tyr Leu Glu Gly Gln Tyr Gly Glu Lys Asp Ala Tyr Val
            260                 265                 270

Gly Val Pro Ala Val Ile Asn Arg Glu Gly Val Arg Glu Ile Val Glu
        275                 280                 285

Leu Glu Leu Asn Glu Asp Glu Lys Ala Lys Phe Ala His Ser Val Lys
    290                 295                 300

Val Leu Lys Glu Thr Met Ala Pro Val Leu
305                 310

<210> SEQ ID NO 59
<211> LENGTH: 320
<212> TYPE: PRT

<213> ORGANISM: Bacillus mycoides

<400> SEQUENCE: 59

Met Lys Gly Glu Ile Asn Met Lys Lys Gly Ile Asn Arg Val Val Leu
1               5                   10                  15

Val Gly Thr Gly Ala Val Gly Cys Ser Tyr Ala Tyr Ser Met Ile Asn
            20                  25                  30

Gln Gly Val Ala Glu Glu Phe Val Leu Val Asp Val Asn Glu Ala Lys
        35                  40                  45

Ala Glu Gly Glu Ala Met Asp Leu Ser His Ala Val Pro Phe Ser Pro
    50                  55                  60

Ala Pro Thr Lys Val Trp Ser Gly Ser Tyr Ala Asp Cys Lys Asp Ala
65                  70                  75                  80

Asp Leu Val Val Ile Thr Ala Gly Leu Pro Gln Lys Pro Gly Glu Thr
                85                  90                  95

Arg Leu Asp Leu Val Glu Lys Asn Thr Lys Ile Phe Lys Gln Ile Val
            100                 105                 110

Arg Gly Ile Met Asp Ser Gly Phe Asp Gly Ile Phe Leu Ile Ala Thr
        115                 120                 125

Asn Pro Val Asp Ile Leu Thr Tyr Val Thr Trp Lys Glu Ser Gly Leu
    130                 135                 140

Pro Lys Glu Arg Val Ile Gly Ser Gly Thr Thr Leu Asp Ser Ala Arg
145                 150                 155                 160

Phe Arg Tyr Met Leu Gly Asp Tyr Leu Asp Val Asp Pro Arg Asn Val
                165                 170                 175

His Ala Tyr Ile Val Gly Glu His Gly Asp Thr Glu Leu Pro Val Trp
            180                 185                 190

Ser His Ala Thr Val Gly Val Gln Lys Leu Glu Thr Ile Leu Ala Asn
        195                 200                 205

Asn Glu Gln Tyr Asn Gln Glu Asp Leu Asp Lys Ile Phe Glu Asn Val
    210                 215                 220

Arg Asp Ala Ala Tyr His Ile Ile Glu Arg Lys Gly Ala Thr Tyr Tyr
225                 230                 235                 240

Gly Ile Gly Met Ser Leu Leu Arg Val Thr Lys Ala Ile Leu Ser Asn
                245                 250                 255

Glu Asn Ser Val Leu Thr Val Ser Ala Tyr Leu Glu Gly Gln Tyr Gly
            260                 265                 270

Glu Lys Asp Ala Phe Val Gly Val Pro Ala Val Ile Asn Arg Glu Gly
        275                 280                 285

Val Arg Glu Ile Val Glu Leu Glu Leu Asn Glu Glu Lys Ala Lys
    290                 295                 300

Phe Ala His Ser Val Lys Val Leu Lys Glu Thr Met Ala Pro Val Leu
305                 310                 315                 320

<210> SEQ ID NO 60
<211> LENGTH: 312
<212> TYPE: PRT
<213> ORGANISM: Lactobacillus rhamnosus

<400> SEQUENCE: 60

Met Gln His Ser Gly Asn Ile Ile Leu Ile Gly Asp Gly Ala Ile Gly
1               5                   10                  15

Ser Ser Phe Ala Phe Asn Cys Leu Thr Thr Gly Val Gly Gln Ser Leu
            20                  25                  30

Gly Ile Ile Asp Val Asn Glu Lys Arg Val Gln Gly Asp Val Glu Asp

```
            35                  40                  45
Leu Ser Asp Ala Leu Pro Tyr Thr Ser Gln Lys Asn Ile Tyr Ala Ala
 50                  55                  60

Ser Tyr Glu Asp Cys Lys Tyr Ala Asp Ile Ile Val Ile Thr Ala Gly
 65                  70                  75                  80

Ile Ala Gln Lys Pro Gly Gln Thr Arg Leu Glu Leu Leu Ser Ile Asn
                 85                  90                  95

Ala Lys Ile Ile Lys Glu Ile Thr His Asn Ile Met Ala Ser Gly Phe
                100                 105                 110

Asn Gly Phe Ile Leu Val Ala Ser Asn Pro Val Asp Val Leu Ala Glu
            115                 120                 125

Leu Val Leu Glu Glu Ser Gly Leu Pro Arg Asn Gln Val Leu Gly Ser
        130                 135                 140

Gly Thr Ala Leu Asp Ser Ala Arg Leu Arg Ser Glu Ile Gly Leu Arg
145                 150                 155                 160

Tyr Asn Val Asp Ala Arg Ile Val His Gly Tyr Ile Met Gly Glu His
                165                 170                 175

Gly Asp Ser Glu Phe Pro Val Trp Asp Tyr Thr Asn Ile Gly Gly Lys
            180                 185                 190

Pro Ile Leu Asp Trp Ile Pro Lys Asn Arg Gln Ala Ser Asp Leu Ala
        195                 200                 205

Glu Ile Ser His Arg Val Lys Thr Ala Ala Tyr Gly Ile Ile Glu Lys
    210                 215                 220

Lys Gly Ala Thr Phe Tyr Gly Ile Ala Ala Ser Leu Thr Arg Leu Thr
225                 230                 235                 240

Ser Ala Phe Leu Asn Asp Asp Arg Ala Ala Phe Ala Met Ser Val His
                245                 250                 255

Leu Asp Gly Glu Tyr Gly Leu Ser Gly Val Ser Ile Gly Val Pro Val
            260                 265                 270

Ile Leu Gly Ala Asn Gly Leu Glu Arg Ile Ile Glu Leu Asp Leu Asn
        275                 280                 285

Ala Glu Asp His Lys Arg Leu Ala Asp Ser Ala Ala Ile Leu Lys Asp
    290                 295                 300

Asn Leu Lys Lys Ala Gln Glu Ala
305                 310

<210> SEQ ID NO 61
<211> LENGTH: 313
<212> TYPE: PRT
<213> ORGANISM: Lactobacillus fermentum

<400> SEQUENCE: 61

Met Ala Arg Lys Val Ala Val Val Gly Met Gly Asn Val Gly Ala Thr
  1               5                  10                  15

Val Ala His Tyr Leu Val Ala Gly Gly Phe Thr Asp Asp Leu Val Leu
                 20                  25                  30

Ile Asp Pro Arg Glu Glu Lys Val Ala Asp Ala Val Asp Phe Glu
             35                  40                  45

Asp Ala Met Ala Asn Leu Glu Tyr His Thr Asn Ile Phe Val Asn Asp
 50                  55                  60

Tyr Glu Ala Leu Ala Asp Ala Asp Val Val Ser Ala Leu Gly Asn
 65                  70                  75                  80

Ile Lys Leu Gln Asp Asn Pro Asp Asp Asp Arg Phe Ala Glu Leu Pro
                 85                  90                  95
```

```
Tyr Thr Arg Val Gln Val Lys Lys Val Ala Thr Lys Leu Lys Glu Val
            100                 105                 110

Gly Phe Asn Gly Ile Ile Val Ala Ile Thr Asn Pro Val Asp Val Ile
        115                 120                 125

Thr Ser Leu Tyr Gln Glu Ile Thr Gly Leu Pro Lys Asn His Val Ile
130                 135                 140

Gly Thr Gly Thr Leu Leu Asp Ser Ala Arg Met Lys Arg Ala Val Ala
145                 150                 155                 160

Lys Lys Leu Asn Leu Asp Pro Arg Ser Val Ala Gly Tyr Asn Leu Gly
                165                 170                 175

Glu His Gly Asn Ser Gln Phe Thr Ala Trp Ser Thr Val Arg Val Leu
            180                 185                 190

Gly Lys Pro Ile Glu Gln Ile Ala Asp Gln Lys Gly Leu Asp Leu Val
        195                 200                 205

Asp Leu Asp Lys Ala Ala Arg Glu Gly Gly Phe Ile Val Phe Arg Gly
210                 215                 220

Lys Lys Tyr Thr Ser Tyr Gly Val Ala Thr Ala Ala Val Arg Leu Val
225                 230                 235                 240

Asn Thr Ile Leu Ser Asn Ala Leu Thr Glu Leu Pro Val Ser Asn Tyr
                245                 250                 255

Arg Glu Glu Tyr Gly Val Tyr Leu Ser Tyr Pro Ala Val Val Gly Arg
            260                 265                 270

Asp Gly Ile Val Glu Gln Cys Gln Leu Asp Leu Thr Ala Glu Glu Leu
        275                 280                 285

Gln Lys Leu Gln Val Ser Ala Asp Phe Ile Lys Gln Lys Phe Ala Glu
290                 295                 300

Ser Leu Glu Ala Ala Asp Gln Glu Asp
305                 310

<210> SEQ ID NO 62
<211> LENGTH: 307
<212> TYPE: PRT
<213> ORGANISM: Lactobacillus delbrueckii

<400> SEQUENCE: 62

Met Ser Arg Lys Val Leu Leu Val Gly Asp Gly Ala Val Gly Ser Asn
1               5                   10                  15

Phe Ala Asn Asp Leu Leu Gln Thr Thr Arg Val Asp Glu Leu Val Ile
            20                  25                  30

Cys Asp Leu Asn Lys Asp Arg Ala Ala Gly Asp Cys Leu Asp Leu Glu
        35                  40                  45

Asp Met Thr Tyr Phe Thr Gly Gln Thr Lys Leu Arg Ala Gly Asp Tyr
    50                  55                  60

Ser Asp Ala Ala Asp Ala Asp Val Val Ile Thr Ala Gly Val Pro
65                  70                  75                  80

Arg Lys Pro Gly Glu Ser Arg Leu Asp Leu Ile Lys Lys Asn Glu Ala
                85                  90                  95

Ile Leu Arg Ser Ile Val Asp Pro Val Val Ala Ser Gly Phe Ser Gly
            100                 105                 110

Ile Phe Val Val Ser Ala Asn Pro Val Asp Ile Leu Thr Thr Leu Thr
        115                 120                 125

Gln Lys Leu Ser Gly Phe Pro Lys Lys Arg Val Ile Gly Thr Gly Thr
130                 135                 140

Ser Leu Asp Ser Ala Ser Leu Arg Val Glu Leu Ala Lys Arg Leu Gln
145                 150                 155                 160
```

-continued

Val Pro Ile Glu Ser Val Asn Ala Trp Val Leu Gly Glu His Gly Asp
                165                 170                 175

Ser Ser Phe Glu Asn Phe Ser Ser Ala Val Val Asn Gly Lys Pro Leu
            180                 185                 190

Leu Asp Tyr Pro Gly Met Thr Glu Ala Ala Leu Asp Glu Ile Glu Ala
        195                 200                 205

His Val Arg Glu Lys Gly Ser Glu Ile Ile Val Lys Lys Gly Ala Thr
    210                 215                 220

Tyr Tyr Gly Val Ala Met Met Leu Ala Lys Ile Val Thr Ala Ile Leu
225                 230                 235                 240

Glu Asn Asn Asp Leu Ala Leu Pro Leu Ser Ala Pro Leu His Gly Glu
                245                 250                 255

Tyr Gly Ile Lys Asp Glu Ile Tyr Leu Gly Thr Leu Ala Ile Ile Asn
            260                 265                 270

Gly Gln Gly Ile Ser His Val Leu Glu Leu Pro Leu Asn Asp Ser Glu
        275                 280                 285

Leu Ala Lys Met Arg Ala Ser Ala Ala Thr Ile Lys Ala Thr Leu Asp
    290                 295                 300

Ser Leu Gly
305

<210> SEQ ID NO 63
<211> LENGTH: 325
<212> TYPE: PRT
<213> ORGANISM: Lactococcus lactis

<400> SEQUENCE: 63

Met Ala Asp Lys Gln Arg Lys Lys Val Ile Leu Val Gly Asp Gly Ala
1               5                   10                  15

Val Gly Ser Ser Tyr Ala Phe Ala Leu Val Asn Gln Gly Ile Ala Gln
            20                  25                  30

Glu Leu Gly Ile Val Asp Leu Phe Lys Glu Lys Thr Gln Gly Asp Ala
        35                  40                  45

Glu Asp Leu Ser His Ala Leu Ala Phe Thr Ser Pro Lys Lys Ile Tyr
    50                  55                  60

Ser Ala Asp Tyr Ser Asp Ala Ser Asp Ala Asp Leu Val Val Leu Thr
65                  70                  75                  80

Ser Gly Ala Pro Gln Lys Pro Gly Glu Thr Arg Leu Asp Leu Val Glu
                85                  90                  95

Lys Asn Leu Arg Ile Thr Lys Asp Val Val Thr Lys Ile Val Ala Ser
            100                 105                 110

Gly Phe Lys Gly Ile Phe Leu Val Ala Ala Asn Pro Val Asp Ile Leu
        115                 120                 125

Thr Tyr Ala Thr Trp Lys Phe Ser Gly Phe Pro Lys Asn Arg Val Val
    130                 135                 140

Gly Ser Gly Thr Ser Leu Asp Thr Ala Arg Phe Arg Gln Ala Leu Ala
145                 150                 155                 160

Glu Lys Val Asp Val Asp Ala Arg Ser Ile His Ala Tyr Ile Met Gly
                165                 170                 175

Glu His Gly Asp Ser Glu Phe Ala Val Trp Ser His Ala Asn Val Ala
            180                 185                 190

Gly Val Lys Leu Glu Gln Trp Phe Gln Glu Asn Asp Tyr Leu Asn Glu
        195                 200                 205

Ala Glu Ile Val Glu Leu Phe Glu Ser Val Arg Asp Ala Ala Tyr Ser

```
                      210                   215                     220
Ile Ile Ala Lys Lys Gly Ala Thr Phe Tyr Gly Val Ala Val Ala Leu
225                 230                 235                 240

Ala Arg Ile Thr Lys Ala Ile Leu Asp Asp Glu His Ala Val Leu Pro
                245                 250                 255

Val Ser Val Phe Gln Asp Gly Gln Tyr Gly Val Ser Asp Cys Tyr Leu
                260                 265                 270

Gly Gln Pro Ala Val Gly Ala Glu Gly Val Val Asn Pro Ile His
            275                 280                 285

Ile Pro Leu Asn Asp Ala Glu Met Gln Lys Met Glu Ala Ser Gly Ala
            290                 295                 300

Gln Leu Lys Ala Ile Ile Asp Glu Ala Phe Ala Lys Glu Glu Phe Ala
305                 310                 315                 320

Ser Ala Val Lys Asn
                325

<210> SEQ ID NO 64
<211> LENGTH: 1014
<212> TYPE: DNA
<213> ORGANISM: Lactobacillus helveticus LDH
<220> FEATURE:
<221> NAME/KEY: CDS
<222> LOCATION: (1)..(1014)

<400> SEQUENCE: 64 atg aca aag gtt ttt gct tac gct att cga aaa gac gaa gaa cca ttc      48
Met Thr Lys Val Phe Ala Tyr Ala Ile Arg Lys Asp Glu Glu Pro Phe
1               5                   10                  15 ttg aat gaa tgg aag gaa gct cac aag gat atc gat gtt gat tac act      96
Leu Asn Glu Trp Lys Glu Ala His Lys Asp Ile Asp Val Asp Tyr Thr
            20                  25                  30 gat aaa ctt ttg act cct gaa act gct aag cta gct aag ggt gct gac     144
Asp Lys Leu Leu Thr Pro Glu Thr Ala Lys Leu Ala Lys Gly Ala Asp
        35                  40                  45 ggt gtt gtt gtt tac caa caa tta gac tac act gca gat act ctt caa     192
Gly Val Val Val Tyr Gln Gln Leu Asp Tyr Thr Ala Asp Thr Leu Gln
    50                  55                  60 gct tta gca gac gct ggc gta act aag atg tca tta cgt aac gtt ggt     240
Ala Leu Ala Asp Ala Gly Val Thr Lys Met Ser Leu Arg Asn Val Gly
65                  70                  75                  80 gtt gac aac att gat atg gac aag gct aag gaa tta ggt ttc caa att     288
Val Asp Asn Ile Asp Met Asp Lys Ala Lys Glu Leu Gly Phe Gln Ile
                85                  90                  95 acc aat gtt cct gtt tac tca cca aac gct att gct gaa cat gct gct     336
Thr Asn Val Pro Val Tyr Ser Pro Asn Ala Ile Ala Glu His Ala Ala
            100                 105                 110 att cag gct gca cgt gta tta cgt caa gac aag cgc atg gac gaa aag     384
Ile Gln Ala Ala Arg Val Leu Arg Gln Asp Lys Arg Met Asp Glu Lys
        115                 120                 125 atg gct aaa cgt gac tta cgt tgg gca cca act atc ggc cgt gaa gtt     432
Met Ala Lys Arg Asp Leu Arg Trp Ala Pro Thr Ile Gly Arg Glu Val
    130                 135                 140 cgt gac caa gtt gtc ggt gtt gtt ggt act ggt cac att ggt caa gta     480
Arg Asp Gln Val Val Gly Val Val Gly Thr Gly His Ile Gly Gln Val
145                 150                 155                 160 ttt atg cgt att atg gaa ggt ttc ggt gca aag gtt att gct tac gat     528
Phe Met Arg Ile Met Glu Gly Phe Gly Ala Lys Val Ile Ala Tyr Asp
                165                 170                 175 atc ttc aag aac cca gaa ctt gaa aag aag ggt tac tac gtt gac tca     576
```

```
Ile Phe Lys Asn Pro Glu Leu Glu Lys Lys Gly Tyr Tyr Val Asp Ser
                180                 185                 190 ctt gac gac ttg tac aag caa gct gat gta att tca ctt cac gta cca        624
Leu Asp Asp Leu Tyr Lys Gln Ala Asp Val Ile Ser Leu His Val Pro
            195                 200                 205 gat gtt cca gct aac gtt cac atg atc aac gac aag tca atc gct gaa        672
Asp Val Pro Ala Asn Val His Met Ile Asn Asp Lys Ser Ile Ala Glu
        210                 215                 220 atg aaa gac ggc gtt gta att gta aac tgc tca cgt ggt cga ctt gtt        720
Met Lys Asp Gly Val Val Ile Val Asn Cys Ser Arg Gly Arg Leu Val
225                 230                 235                 240 gac act gac gct gta atc cgt ggt ttg gac tca ggc aag atc ttc ggc        768
Asp Thr Asp Ala Val Ile Arg Gly Leu Asp Ser Gly Lys Ile Phe Gly
                245                 250                 255 ttc gtt atg gat act tac gaa gac gaa gtt ggt gta ttt aac aag gat        816
Phe Val Met Asp Thr Tyr Glu Asp Glu Val Gly Val Phe Asn Lys Asp
            260                 265                 270 tgg gaa ggt aaa gaa ttc cca gac aag cgt ttg gca gac tta att gat        864
Trp Glu Gly Lys Glu Phe Pro Asp Lys Arg Leu Ala Asp Leu Ile Asp
        275                 280                 285 cgt cca aac gta ttg gta act cca cac acc gcc ttc tac act act cac        912
Arg Pro Asn Val Leu Val Thr Pro His Thr Ala Phe Tyr Thr Thr His
    290                 295                 300 gct gta cgt aac atg gtt gtt aag gca ttc aac aac aac ttg aag tta        960
Ala Val Arg Asn Met Val Val Lys Ala Phe Asn Asn Asn Leu Lys Leu
305                 310                 315                 320 atc aac ggc gaa aag cca gat tct cca gtt gct ttg aac aag aac aag       1008
Ile Asn Gly Glu Lys Pro Asp Ser Pro Val Ala Leu Asn Lys Asn Lys
                325                 330                 335 ttt taa                                                                1014
Phe

<210> SEQ ID NO 65
<211> LENGTH: 337
<212> TYPE: PRT
<213> ORGANISM: Lactobacillus helveticus LDH

<400> SEQUENCE: 65

Met Thr Lys Val Phe Ala Tyr Ala Ile Arg Lys Asp Glu Glu Pro Phe
1               5                   10                  15

Leu Asn Glu Trp Lys Glu Ala His Lys Asp Ile Asp Val Asp Tyr Thr
            20                  25                  30

Asp Lys Leu Leu Thr Pro Glu Thr Ala Lys Leu Ala Lys Gly Ala Asp
        35                  40                  45

Gly Val Val Val Tyr Gln Gln Leu Asp Tyr Thr Ala Asp Thr Leu Gln
    50                  55                  60

Ala Leu Ala Asp Ala Gly Val Thr Lys Met Ser Leu Arg Asn Val Gly
65                  70                  75                  80

Val Asp Asn Ile Asp Met Asp Lys Ala Lys Glu Leu Gly Phe Gln Ile
                85                  90                  95

Thr Asn Val Pro Val Tyr Ser Pro Asn Ala Ile Ala Glu His Ala Ala
            100                 105                 110

Ile Gln Ala Ala Arg Val Leu Arg Gln Asp Lys Arg Met Asp Glu Lys
        115                 120                 125

Met Ala Lys Arg Asp Leu Arg Trp Ala Pro Thr Ile Gly Arg Glu Val
    130                 135                 140

Arg Asp Gln Val Val Gly Val Val Gly Thr Gly His Ile Gly Gln Val
145                 150                 155                 160
```

```
Phe Met Arg Ile Met Glu Gly Phe Gly Ala Lys Val Ile Ala Tyr Asp
                165                 170                 175

Ile Phe Lys Asn Pro Glu Leu Glu Lys Lys Gly Tyr Tyr Val Asp Ser
            180                 185                 190

Leu Asp Asp Leu Tyr Lys Gln Ala Asp Val Ile Ser Leu His Val Pro
        195                 200                 205

Asp Val Pro Ala Asn Val His Met Ile Asn Asp Lys Ser Ile Ala Glu
    210                 215                 220

Met Lys Asp Gly Val Val Ile Val Asn Cys Ser Arg Gly Arg Leu Val
225                 230                 235                 240

Asp Thr Asp Ala Val Ile Arg Gly Leu Asp Ser Gly Lys Ile Phe Gly
                245                 250                 255

Phe Val Met Asp Thr Tyr Glu Asp Glu Val Gly Val Phe Asn Lys Asp
            260                 265                 270

Trp Glu Gly Lys Glu Phe Pro Asp Lys Arg Leu Ala Asp Leu Ile Asp
        275                 280                 285

Arg Pro Asn Val Leu Val Thr Pro His Thr Ala Phe Tyr Thr Thr His
    290                 295                 300

Ala Val Arg Asn Met Val Val Lys Ala Phe Asn Asn Asn Leu Lys Leu
305                 310                 315                 320

Ile Asn Gly Glu Lys Pro Asp Ser Pro Val Ala Leu Asn Lys Asn Lys
                325                 330                 335

Phe
```

<210> SEQ ID NO 66
<211> LENGTH: 996
<212> TYPE: DNA
<213> ORGANISM: Leuconostoc mesenteroides LDH
<220> FEATURE:
<221> NAME/KEY: CDS
<222> LOCATION: (1)..(996)

<400> SEQUENCE: 66

```
atg aag att ttt gct tac ggc att cgt gat gat gaa aag cca tca ctt    48
Met Lys Ile Phe Ala Tyr Gly Ile Arg Asp Asp Glu Lys Pro Ser Leu
1               5                   10                  15 gaa gaa tgg aaa gcg gct aac cca gag att gaa gtg gac tac aca caa    96
Glu Glu Trp Lys Ala Ala Asn Pro Glu Ile Glu Val Asp Tyr Thr Gln
                20                  25                  30 gag cta ttg aca cct gaa aca gtt aag ttg gct gag gga tca gat tca    144
Glu Leu Leu Thr Pro Glu Thr Val Lys Leu Ala Glu Gly Ser Asp Ser
            35                  40                  45 gct gtt gtt tac caa caa ctg gac tat aca cgt gaa aca ttg aca gct    192
Ala Val Val Tyr Gln Gln Leu Asp Tyr Thr Arg Glu Thr Leu Thr Ala
        50                  55                  60 tta gct aac gtt ggt ggt act aac ttg tca ttg cgt aac gtt ggt aca    240
Leu Ala Asn Val Gly Gly Thr Asn Leu Ser Leu Arg Asn Val Gly Thr
65                  70                  75                  80 gat aac att gat ttt gat gca gca cgt gaa ttt aac ttt aac att tca    288
Asp Asn Ile Asp Phe Asp Ala Ala Arg Glu Phe Asn Phe Asn Ile Ser
                85                  90                  95 aat gtt cct gtt tat tca cca aat gct att gca gaa cac tca atg att    336
Asn Val Pro Val Tyr Ser Pro Asn Ala Ile Ala Glu His Ser Met Ile
                100                 105                 110 caa tta tct cgt ttg cta cgt cgc acg aaa gca ttg gat gcc aaa att    384
Gln Leu Ser Arg Leu Leu Arg Arg Thr Lys Ala Leu Asp Ala Lys Ile
            115                 120                 125
```

```
gct aag cac gac ttg cgc tgg gca cca aca att gga cgt gaa atg cgt    432
Ala Lys His Asp Leu Arg Trp Ala Pro Thr Ile Gly Arg Glu Met Arg
    130                 135                 140 atg caa aca gtt ggt gtt att ggt aca ggc cat att ggc cgt gtt gct    480
Met Gln Thr Val Gly Val Ile Gly Thr Gly His Ile Gly Arg Val Ala
145                 150                 155                 160 att aac att ttg aaa ggc ttt ggg gca aag gtt att gct tat gat aag    528
Ile Asn Ile Leu Lys Gly Phe Gly Ala Lys Val Ile Ala Tyr Asp Lys
                165                 170                 175 tac cca aat gct gaa ttg caa gca gaa ggt ttg tac gtt gac aca tta    576
Tyr Pro Asn Ala Glu Leu Gln Ala Glu Gly Leu Tyr Val Asp Thr Leu
            180                 185                 190 gac gaa tta tat gca caa gct gat gca att tca ttg tat gtt cct ggt    624
Asp Glu Leu Tyr Ala Gln Ala Asp Ala Ile Ser Leu Tyr Val Pro Gly
        195                 200                 205 gtg cct gaa aac cat cat cta atc aat gca gag gct att gct aag atg    672
Val Pro Glu Asn His His Leu Ile Asn Ala Glu Ala Ile Ala Lys Met
    210                 215                 220 aat gat ggc gtg gtt atc atg aat gct gcg cgt ggt aat ttg atg gac    720
Asn Asp Gly Val Val Ile Met Asn Ala Ala Arg Gly Asn Leu Met Asp
225                 230                 235                 240 att gat gct att att gat ggt ttg aat tct ggt aag att tca gac ttc    768
Ile Asp Ala Ile Ile Asp Gly Leu Asn Ser Gly Lys Ile Ser Asp Phe
                245                 250                 255 ggt atg gac gtt tat gaa aat gaa gtt ggc ttg ttc aat gaa gat tgg    816
Gly Met Asp Val Tyr Glu Asn Glu Val Gly Leu Phe Asn Glu Asp Trp
            260                 265                 270 tct ggt aaa gaa ttc cca gat gct aag att gct gac ttg att tca cgc    864
Ser Gly Lys Glu Phe Pro Asp Ala Lys Ile Ala Asp Leu Ile Ser Arg
        275                 280                 285 gaa aat gta ttg gtt acg cca cat acg gct ttc tat aca act aaa gct    912
Glu Asn Val Leu Val Thr Pro His Thr Ala Phe Tyr Thr Thr Lys Ala
    290                 295                 300 gtt cta gaa atg gtt cac caa tca ttt gat gca gca gtt gct ttc gcc    960
Val Leu Glu Met Val His Gln Ser Phe Asp Ala Ala Val Ala Phe Ala
305                 310                 315                 320 aaa ggt gag aag cca gct att gct gtt gaa tat taa                    996
Lys Gly Glu Lys Pro Ala Ile Ala Val Glu Tyr
                325                 330

<210> SEQ ID NO 67
<211> LENGTH: 331
<212> TYPE: PRT
<213> ORGANISM: Leuconostoc mesenteroides LDH

<400> SEQUENCE: 67

Met Lys Ile Phe Ala Tyr Gly Ile Arg Asp Asp Glu Lys Pro Ser Leu
1               5                   10                  15

Glu Glu Trp Lys Ala Ala Asn Pro Glu Ile Glu Val Asp Tyr Thr Gln
            20                  25                  30

Glu Leu Leu Thr Pro Glu Thr Val Lys Leu Ala Glu Gly Ser Asp Ser
        35                  40                  45

Ala Val Val Tyr Gln Gln Leu Asp Tyr Thr Arg Glu Thr Leu Thr Ala
    50                  55                  60

Leu Ala Asn Val Gly Gly Thr Asn Leu Ser Leu Arg Asn Val Gly Thr
65                  70                  75                  80

Asp Asn Ile Asp Phe Asp Ala Ala Arg Glu Phe Asn Phe Asn Ile Ser
                85                  90                  95

Asn Val Pro Val Tyr Ser Pro Asn Ala Ile Ala Glu His Ser Met Ile
```

-continued

```
                   100                 105                 110
Gln Leu Ser Arg Leu Leu Arg Arg Thr Lys Ala Leu Asp Ala Lys Ile
            115                 120                 125

Ala Lys His Asp Leu Arg Trp Ala Pro Thr Ile Gly Arg Glu Met Arg
            130                 135                 140

Met Gln Thr Val Gly Val Ile Gly Thr Gly His Ile Gly Arg Val Ala
145                 150                 155                 160

Ile Asn Ile Leu Lys Gly Phe Gly Ala Lys Val Ile Ala Tyr Asp Lys
                165                 170                 175

Tyr Pro Asn Ala Glu Leu Gln Ala Glu Gly Leu Tyr Val Asp Thr Leu
            180                 185                 190

Asp Glu Leu Tyr Ala Gln Ala Asp Ala Ile Ser Leu Tyr Val Pro Gly
            195                 200                 205

Val Pro Glu Asn His His Leu Ile Asn Ala Glu Ala Ile Ala Lys Met
            210                 215                 220

Asn Asp Gly Val Val Ile Met Asn Ala Ala Arg Gly Asn Leu Met Asp
225                 230                 235                 240

Ile Asp Ala Ile Ile Asp Gly Leu Asn Ser Gly Lys Ile Ser Asp Phe
                245                 250                 255

Gly Met Asp Val Tyr Glu Asn Glu Val Gly Leu Phe Asn Glu Asp Trp
                260                 265                 270

Ser Gly Lys Glu Phe Pro Asp Ala Lys Ile Ala Asp Leu Ile Ser Arg
            275                 280                 285

Glu Asn Val Leu Val Thr Pro His Thr Ala Phe Tyr Thr Thr Lys Ala
            290                 295                 300

Val Leu Glu Met Val His Gln Ser Phe Asp Ala Ala Val Ala Phe Ala
305                 310                 315                 320

Lys Gly Glu Lys Pro Ala Ile Ala Val Glu Tyr
                325                 330
```

COMPOSITIONS AND METHODS FOR BIOLOGICAL PRODUCTION OF LACTATE FROM $C_1$ COMPOUNDS USING LACTATE DEHYDROGENASE TRANSFORMANTS

CROSS-REFERENCE TO RELATED APPLICATIONS

This application claims the benefit of provisional applications U.S. Application No. 61/836,609, filed Jun. 18, 2013, and U.S. Application No. 61/928,390, filed Jan. 16, 2014, pursuant 35 U.S.C. § 119(e), both of which are incorporated herein by reference in their entirety.

REFERENCE TO SEQUENCE LISTING

The "Sequence Listing" submitted electronically concurrently herewith pursuant 37 C.F.R. § 1.821 in computer readable form (CRF) via EFS-Web as file name 200206_414USPC_SEQUENCE_LISTING.txt is incorporated herein by reference. The electronic copy of the Sequence Listing was created on Dec. 15, 2015, and the size on disk is 221 KB.

BACKGROUND

Lactic acid, which can be produced chemically or biologically, is a widely used chemical compound that ranges from use in the cosmetic industry to use in the food industry to the pharmaceutical and chemical industries. Since lactic acid contains two reactive functional groups, a carboxylic group and a hydroxyl group, it can undergo a variety of chemical conversions into potentially useful chemicals, such as propylene oxide, acetaldehyde, acrylic acid, propanoic acid, 2,3-pentanedione, and lactide (Varadarajan and Miller, *Biotechnol. Progr.* 15:845, 1999). Recently, increased attention has been directed at the use of lactic acid to produce polylactic acid (PLA), which is a renewable raw material used in the manufacture of bioplastics that offers a more sustainable alternative to petrochemical resources. Optically pure lactic acid can be polymerized into a high molecular mass PLA through the serial reactions of polycondensation, depolymerization, and ring-opening polymerization (Södergård and Stolt, *Prog. Polym. Sci.* 27:1123, 2002). The resultant PLA polymer has various uses in wide ranging applications, including protective clothing, food packaging, mulch film, trash bags, rigid containers, shrink wrap, and short shelf-life trays (Drumright et al., *Adv. Mater.* 12:1841, 2000; Vink et al., *Polym. Degrad. Stabil.* 80:403, 2003).

The carbohydrate feedstocks currently used in biological lactate production are relatively expensive. Other feedstocks, such as methane, are available cheaply in large quantities. The conversion of methane potentially represents a route to significantly lower cost lactic acid production. However, a practical way of achieving this has not yet been developed.

BRIEF SUMMARY

In one embodiment, the present invention provides a non-naturally occurring $C_1$ metabolizing bacteria comprising an exogenous nucleic acid encoding a lactate dehydrogenase (LDH).

In another embodiment, the present invention provides a non-naturally occurring $C_1$ metabolizing microorganism comprising an exogenous nucleic acid encoding a lactate dehydrogenase, wherein the $C_1$ metabolizing microorganism is a methanotroph.

In a further embodiment, the present invention provides a non-naturally occurring $C_1$ metabolizing microorganism comprising an exogenous nucleic acid encoding a lactate dehydrogenase, wherein the $C_1$ metabolizing microorganism is capable of converting a carbon feedstock into lactate, and wherein the carbon feedstock is selected from the group consisting of methane, carbon dioxide, carbon monoxide, natural gas, and syngas.

In certain embodiments, the present invention provides a non-naturally occurring $C_1$ metabolizing microorganism comprising an exogenous nucleic acid encoding a lacate dehydrogenase, wherein the $C_1$ metabolizing microorganism is not a yeast.

In other embodiments, the present invention provides a non-naturally occurring $C_1$ metabolizing microorganism comprising an exogenous nucleic acid encoding a lactate dehydrogenase, wherein the non-naturally occurring $C_1$ metabolizing microorganism is capable of producing more lactate as compared to that of a corresponding reference $C_1$ metabolizing microorganism when cultured in the presence of a $C_1$ substrate under at least one set of culture conditions.

DETAILED DESCRIPTION

Figure 1:
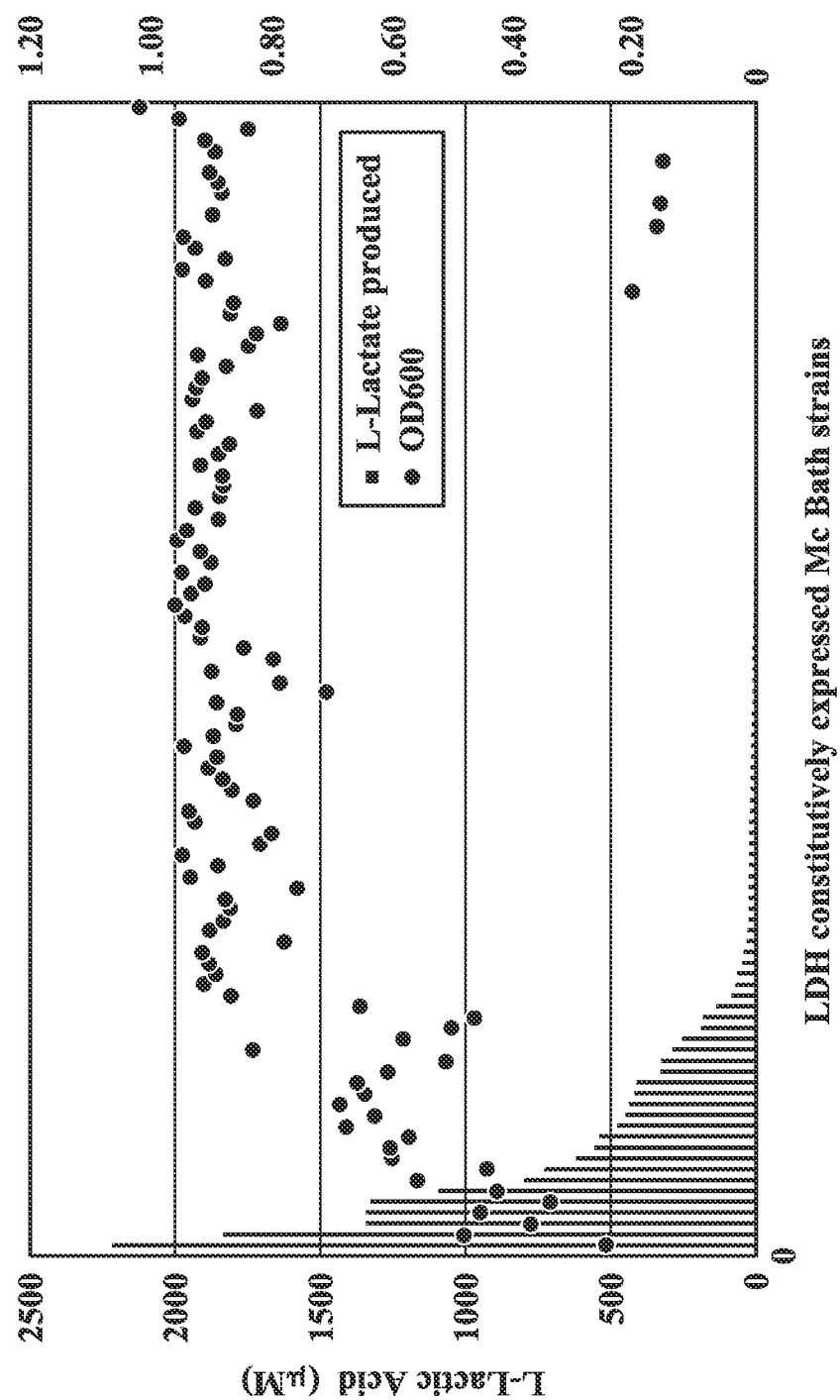
FIG. 1 depicts the level of lactate production for certain recombinant *Methylococcus capsulatus* Bath expressing a heterologous lactate dehydrogenase (ldh) nucleic acid as compared to the $OD_{600}$ after 72 hours of growth.

The instant disclosure provides non-naturally occurring $C_1$ metabolizing microorganisms, and related compositions and methods for the biosynthesis of lactate from a carbon feedstock. Typically, the carbon feedstock comprises a $C_1$ substrate. In a specific embodiment, the present invention provides a non-naturally occurring $C_1$ metabolizing bacteria comprising an exogenous nucleic acid encoding a lactate dehydrogenase (LDH). The present invention also provides a non-naturally occurring $C_1$ metabolizing microorganism comprising an exogenous nucleic acid encoding a lactate dehydrogenase, wherein the $C_1$ metabolizing microorganism is a methanotroph. In a specific embodiment, the present disclosure provides a non-naturally occurring $C_1$ metabolizing microorganism comprising an exogenous nucleic acid encoding a lactate dehydrogenase, wherein the $C_1$ metabolizing microorganism is capable of converting a carbon feedstock into lactate. Typically, the carbon feedstock is selected from the group consisting of methane, carbon dioxide, carbon monoxide, syngas, and natural gas. The present invention further provides a non-naturally occurring $C_1$ metabolizing microorganism comprising an exogenous nucleic acid encoding a lactate dehydrogenase, wherein the $C_1$ metabolizing microorganism is not a yeast. In a still further embodiment, the present invention provides a non-naturally occurring $C_1$ metabolizing microorganism comprising an exogenous nucleic acid encoding a lactate dehydrogenase, wherein the non-naturally occurring $C_1$ metabolizing microorganism is capable of producing more lactate as compared to that of a corresponding reference $C_1$ metabolizing microorganism when cultured in the presence of a $C_1$ substrate under at least one set of culture conditions. In a further embodiment, the present invention provides non-naturally occurring $C_1$ metabolizing microorganism comprising an exogenous nucleic acid encoding a lactate dehydrogenase, wherein the non-naturally occurring $C_1$ metabolizing microorganism is capable of producing more lactate as compared to that of a corresponding reference $C_1$ metabolizing microorganism when cultured in the presence of a $C_1$ substrate under at least one set of culture conditions.

Prior to setting forth this disclosure in more detail, it may be helpful to an understanding thereof to provide definitions of certain terms to be used herein. Additional definitions are set forth throughout this disclosure.

In the present description, the disclosure of any range herein is intended to be a disclosure of any number within the range, and a disclosure of any range formed by any number within the range, inclusive of the endpoints. As used herein, the term "about" means±20% of the indicated range, value, or structure, unless otherwise indicated. The term "consisting essentially of" limits the scope of a claim to the specified materials or steps, or to those that do not materially affect the basic and novel characteristics of the claimed invention. It should be understood that the terms "a" and "an" as used herein refer to "one or more" of the enumerated components. The use of the alternative, "or", should be understood to mean either one, both, or any combination thereof of the alternatives. As used herein, the terms "include," "have" and "comprise" do not preclude the presence of other elements not otherwise specifically excluded.

When used in connection with a polypeptide, the terms "lactate dehydrogenase" and "LDH" are used interchangeably herein to refer to a polypeptide having lactate dehydrogenase activity, i.e., is capable of catalyzing the reduction of pyruvate to lactate. In some embodiments, the lactate dehydrogenase is an L-lactate dehydrogenase, which catalyzes the reduction of pyruvate to L-lactate (EC 1.1.1.27). In other embodiments, the lactate dehydrogenase is a D-lactate dehydrogenase, which catalyzes the reduction of pyruvate to D-lactate (EC 1.1.1.28).

The term "carbon feedstock" refers herein to any carbon compound(s) capable of being metabolized by the non-naturally occurring $C_1$ metabolizing microorganisms of the present invention, such as, for example, a $C_1$ substrate.

As used herein, the term "$C_1$ substrate" refers to any carbon containing molecule that lacks a carbon-carbon bond. $C_1$ substrates can be found in natural gas, unconventional natural gas, syngas, and include molecules, such as, for example, methane, methanol, formaldehyde, formic acid (formate), carbon monoxide, carbon dioxide, methylated amines (e.g., methylamine, dimethylamine, trimethylamine, etc.), methylated thiols, methyl halogens (e.g., bromomethane, chloromethane, iodomethane, dichloromethane, etc.), cyanide, and the like.

As used herein, the term "methane" refers to the simplest ($C_1$) alkane compound with the chemical formula $CH_4$, which is a colorless and odorless gas at room temperature and pressure.

As used herein, the term "natural gas" refers to naturally occurring subterranean gas mixtures that contain methane. Natural gas may be accessible from porous reservoirs by conventional processes (e.g., drilling, waterflooding). While primarily made up of methane, natural gas may also comprise other light alkane gases (e.g., ethane, propane, butane, pentane), carbon dioxide, nitrogen, hydrogen sulfide, or the like, or any combination thereof.

The term, "unconventional natural gas", refers herein to naturally occurring gas mixtures created in formations with low permeability that must be accessed by unconventional methods, such as hydraulic fracturing, horizontal drilling or directional drilling. Exemplary unconventional natural gas deposits include tight gas sands formed in sandstone or carbonate, coal bed methane formed in coal deposits and adsorbed in coal particles, shale gas formed in fine-grained shale rock and adsorbed in clay particles or held within small pores or microfractures, methane hydrates that are a crystalline combination of natural gas and water formed at low temperature and high pressure in places such as under the oceans and permafrost. Unconventional natural gas tends to have a more variable composition, including having potentially higher levels of ethane, propane, butane, $CO_2$, or any combination thereof, as compared to conventional natural gas.

As used herein, the terms "synthesis gas" or "syngas" refers to a synthetically produced gas mixture containing primarily carbon monoxide (CO) and hydrogen ($H_2$). Syngas may be produced by, for example, steam reforming of natural gas or liquid hydrocarbons, or by gasification of coal, biomass or waste. Syngas may also include methane, $CO_2$, $H_2S$, and other gases in smaller quantities relative to CO and $H_2$.

As used herein, "$C_1$ metabolizing microorganism" refers to any microorganism having the ability to use (i.e., metabolize) a $C_1$ substrate as a source of energy, biomass, and may or may not use other carbon substrates (such as sugars and complex carbohydrates) for energy and biomass. $C_1$ metabolizing microorganisms include bacteria (such as methanotrophs and methylotrophs) and yeast. In certain embodiments, a $C_1$ metabolizing microorganism does not include a photosynthetic microorganism, such as algae. In certain embodiments, a $C_1$ metabolizing microorganism will be an "obligate $C_1$ metabolizing microorganism," meaning it requires $C_1$ substrates as its source of energy. In further embodiments, a $C_1$ metabolizing microorganism (e.g., methanotroph) will be cultured in the presence of a $C_1$ substrate (i.e., using the $C_1$ substrate as a source of energy).

As used herein, the terms "methanotroph," "methanotrophic bacterium" or "methanotrophic bacteria" refer interchangeably herein to methylotrophic bacteria capable of utilizing methane. For example, methane from natural gas can be used as the carbon and energy source for growth. As used herein, the term "methanotrophic bacteria" include "obligate methanotrophic bacteria" that can only utilize methane (e.g., from natural gas) for carbon and energy sources and "facultative methanotrophic bacteria" that are naturally able to use multi-carbon substrates, such as acetate, pyruvate, succinate, malate, or ethanol, in addition to methane as their carbon and energy source.

As used herein, the term "methylotroph" or "methylotrophic bacteria" refers to any bacteria capable of using one-carbon compounds (i.e., compounds that do not contain carbon-carbon bonds). In certain embodiments, a methylotrophic bacterium may be a methanotroph. For example, "methanotrophic bacteria" refers to any methylotrophic bacteria that have the ability to utilize methane as it primary source of carbon and energy. Exemplary methanotrophic bacteria include *Methylomonas, Methylobacter, Methylococcus, Methylosinus, Methylocystis, Methylomicrobium*, or *Methanomonas*. In certain other embodiments, the methylotrophic bacterium is an "obligate methylotrophic bacterium," which refers to bacteria that are limited to the use of $C_1$ substrates for the generation of energy.

As used herein, the term "host" refers to a cell or microorganism (e.g., methanotroph) that may be genetically modified with an exogenous nucleic acid to produce a polypeptide of interest (e.g., lactate dehydrogenase). In certain embodiments, a host cell may optionally already possess or be modified to include other genetic modifications that confer desired properties that are related or unrelated to the exogenous LDH encoded by the exogenous nucleic acid (e.g., deleted pyruvate decarboxylase). For example, a host cell may possess genetic modifications that: minimize or reduce the utilization of the lactate product being produced, minimize or reduce production of host cell growth inhibitors, provide high growth, provide tolerance of contaminants or particular culture conditions (e.g., acid tolerance, biocide resistance), confer the ability to metabolize additional carbon substrates, or confer the ability to synthesize further desirable products or intermediates.

As used herein, the terms "nucleic acid molecule" and "nucleic acid" are used interchangeably to refer to a polymeric compound comprised of covalently linked subunits of nucleotides. Synthetic production of nucleic acids includes chemical and biological methods of reproducing nucleic acids. Nucleic acids include polyribonucleic acid (RNA), polydeoxyribonucleic acid (DNA), both of which may be single or double stranded. DNA includes cDNA, genomic DNA, synthetic DNA, semi-synthetic DNA, or the like. The terms "LDH nucleic acid" and "LDH-encoding nucleic acid" are used interchangeably herein to a nucleic acid that encodes a polypeptide having LDH activity.

The terms "polypeptide" and "protein" are used interchangeably herein to refer to a polymer of amino acids.

As used herein, the terms "recombinant" or "non-natural" (or "non-naturally occurring") refer interchangeably to an organism, microorganism, cell, nucleic acids, or vector that includes at least one genetic alteration or has been modified by introduction of an exogenous nucleic acid, or refers to a cell that has been altered such that the expression of an endogenous nucleic acid or gene can be controlled, where such alterations or modifications are introduced or induced by genetic engineering. Genetic alterations include, for example, modifications introducing expressible nucleic acids encoding proteins or enzymes, or other nucleic acid additions, deletions, substitutions or other functional disruption of a cell's genetic material or modifications achieved by classical strain evolution or directed molecular evolution methods that are known in the art. Such modifications include, for example, modifications in coding regions (and functional fragments thereof) and non-coding regulatory regions in which the modifications alter expression of a gene or operon.

As used herein, the terms "transformation" and "transforming" refers to the introduction of a nucleic acid (e.g., exogenous or heterologous nucleic acid) into a host cell. The transformed host cell may carry the exogenous or heterologous nucleic acid extra-chromosomally or integrated in the chromosome. Integration into a host cell genome and self-replicating vectors generally result in genetically stable inheritance of the transformed nucleic acid molecule. Host cells containing the transformed nucleic acids are referred to interchangeably as "recombinant" or "non-naturally occurring" or "genetically engineered" or "transformed" or "transgenic" cells (e.g., bacteria).

As used herein, the term "corresponding reference $C_1$ metabolizing microorganism" refers to the corresponding $C_1$ metabolizing microorganism without the LDH-encoding exogenous nucleic acid.

When used in connection with a nucleic acid, polypeptide, compound, or activity, the terms "endogenous" or "native" are used interchangeably to refer to a nucleic acid, polypeptide, compound or activity that is present in the wild type host cell. When used in connection with a cell, the term "native" refers to the wild type cell.

As used herein, "heterologous" or "exogenous" nucleic acid, construct or sequence are used interchangeably herein to refer to a nucleic acid molecule or portion of a nucleic acid molecule that is not native to a host cell, or a nucleic acid molecule or portion of a nucleic acid molecule native to a host cell that has been altered or mutated, or a nucleic acid molecule with an altered expression as compared to the native expression levels under similar conditions. In addition, the terms "heterologous" and "exogenous" can refer to a biological activity that is different or altered from that found endogenous to a host cell, or is not native to a host cell but instead is encoded by a nucleic acid molecule introduced into the host cell.

The "percent identity" between two or more nucleic acid sequences or two or more amino acid sequences is a function of the number of identical positions shared by the sequences (i.e., % identity=number of identical positions/total number of positions×100), taking into account the number of gaps, and the length of each gap that needs to be introduced to optimize alignment of two or more sequences. Two sequences are optimally aligned when they are aligned using defined parameters, i.e., a defined amino acid substitution matrix, a gap existence penalty (also termed a gap open penalty), and gap extension penalty, so as to arrive at the highest similarity score possible for that pair of sequences.

"Optimal alignment" for the determination of percent identity between two or more sequences is accomplished using a mathematical algorithm, such as the BLAST algorithm (e.g., Altschul et al., *J. Mol. Biol.* 215:403, 1990; see also BLASTN at the world wide web ncbi.nlm.nih.gov/BLAST). For amino acid sequences, the BLOSUM62 matrix (Henikoff and Henikoff (1992) *Proc. Natl. Acad. Sci. USA* 89(22):10916-10919) is used as a default scoring substitution matrix in amino acid sequence alignment algorithms, such as BLASTP. The gap existence penalty is imposed for the introduction of a single amino acid gap in one of the aligned sequences, and the gap extension penalty is imposed for each residue position in the gap. Optimal alignment of amino acid sequences is carried out using BLASTP with the following alignment parameters: BLOSUM62 scoring matrix, gap existence penalty=11, and gap extension penalty=1. For optimal alignment of nucleic acid sequences, BLASTN is used with the following alignment parameters: Match/Mismatch Scores=1/−3, and gap existence penalty=5, and gap extension penalty=2. The similarity score is defined by the amino acid or nucleotide positions of each sequence at which the alignment begins and ends (e.g., the alignment window), and optionally by the insertion of a gap or multiple gaps into one or both sequences so as to arrive at the highest possible similarity score.

A "conservative substitution" is recognized in the art as a substitution of one amino acid for another amino acid that has similar properties. Exemplary conservative substitutions are well known in the art (see, e.g., WO 97/09433, page 10, published Mar. 13, 1997; Lehninger, Biochemistry, Second Edition; Worth Publishers, Inc. NY:NY (1975), pp. 71-77;

Lewin, Genes IV, Oxford University Press, NY and Cell Press, Cambridge, Mass. (1990), p. 8).

As used herein, "overexpressed" when used in reference to a nucleic acid or a protein refers to an increase in expression or activity of the nucleic acid or protein. Increased expression or activity includes expression or activity of a nucleic acid or protein being increased above the level of a wild-type (non-genetically engineered) control or reference microorganism. A nucleic acid or protein is overexpressed if the expression or activity is in a microorganism where it is not normally expressed or active. A nucleic acid or protein is overexpressed if the expression or activity is extended or present longer in the recombinant microorganism than in a wild-type control or reference microorganism.

"Inhibit" or "inhibited," as used herein, refers to an alteration, reduction, down regulation, abrogation or deletion, directly or indirectly, in the expression of a target gene or in the activity of a target molecule relative to a control, endogenous or reference molecule, wherein the alteration, reduction, down regulation or abrogation is statistically, biologically, industrially, or clinically significant.

As used herein, the term "derivative" refers to a modification of a compound by chemical or biological means (e.g., with or without an enzyme), which modified compound is structurally similar to a parent compound and (actually or theoretically) derivable from that parent compound. A derivative may have different chemical, biological or physical properties from the parent compound, such as being more hydrophilic or having altered reactivity as compared to the parent compound. Derivatization (i.e., modification) may involve substitution of one or more moieties within the molecule (e.g., a change in functional group). For example, a hydrogen may be substituted with a halogen, such as fluorine or chlorine, or a hydroxyl group (—OH) may be replaced with a carboxylic acid moiety (—COOH). Other exemplary derivatizations include polymerization, glycosylation, alkylation, acylation, acetylation, ubiquitination, esterification, and amidation.

The term "derivative" also refers to all solvates, for example, hydrates or adducts (e.g., adducts with alcohols), active metabolites, and salts of a parent compound. The type of salt depends on the nature of the moieties within the compound. For example, acidic groups, such as carboxylic acid groups, can form alkali metal salts or alkaline earth metal salts (e.g., sodium salts, potassium salts, magnesium salts, calcium salts, and also salts with physiologically tolerable quaternary ammonium ions and acid addition salts with ammonia and physiologically tolerable organic amines such as, for example, triethylamine, ethanolamine or tris-(2-hydroxyethyl)amine). Basic groups can form acid addition salts with, for example, inorganic acids such as hydrochloric acid, sulfuric acid or phosphoric acid, or with organic carboxylic acids or sulfonic acids such as acetic acid, citric acid, lactic acid, benzoic acid, maleic acid, fumaric acid, tartaric acid, methanesulfonic acid or p-toluenesulfonic acid. Compounds that simultaneously contain a basic group and an acidic group, for example, a carboxyl group in addition to basic nitrogen atoms, can be present as zwitterions. Salts can be obtained by customary methods known to those skilled in the art, for example, by combining a compound with an inorganic or organic acid or base in a solvent or diluent, or from other salts by cation exchange or anion exchange.

As used herein, the term "lactate" refers to all forms of lactic acid, including all derivative forms such as a lactic acid salt, lactic acid ion, lactic acid ester, a lactic acid solvate, and/or an oligomer of lactic acid or a lactic acid ester.

The term "expression control sequence" means a nucleic acid sequence that directs transcription of a nucleic acid to which it is operatively linked, such as, for example, a promoter or an enhancer.

The term "operably linked" refers herein to a configuration in which a control sequence is appropriately placed at a position relative to the exogenous LDH-encoding nucleic acid such that the control sequence influences the expression of the encoded LDH.

As used herein, the term "corresponding parental lactate dehydrogenase" refers to a naturally occurring lactate dehydrogenase or otherwise known lactate dehydrogenase from which the amino acid sequence of an LDH sequence variant is based on.

$C_1$ Metabolizing Microorganisms—Host Cells

Non-naturally occurring $C_1$ metabolizing microorganisms of the present invention are prepared by introducing the desired exogenous LDH-encoding nucleic acid into the desired host cell. The $C_1$ metabolizing microorganism that will be genetically modified may be a natural strain, strain adapted (e.g., performing fermentation to select for strains with reduced lactate utilization, improved growth rates, or increased total biomass yield compared to the parent strain), or previously recombinantly modified to convert alkanes or alkenes to lactate, to have reduced or minimal pyruvate decarboxylase activity, to have increased growth rates, or any combination thereof. In certain preferred embodiments, the $C_1$ metabolizing microorganisms are not photosynthetic microorganisms, such as algae or plants. Often, the $C_1$ metabolizing microorganism of the present invention is not yeast, and typically, is not a fungi. In some embodiments, the $C_1$ metabolizing microorganism of the present invention is not a photosynthetic microorganism, or a fungi.

In certain embodiments, the $C_1$ metabolizing microorganism of the present invention is a prokaryote or bacteria which is a genetically modified cell from one or more of the genera *Methylomonas, Methylobacter, Methylococcus, Methylosinus, Methylocystis, Methylomicrobium, Methanomonas, Methylophilus, Methylobacillus, Methylobacterium, Hyphomicrobium, Xanthobacter, Bacillus, Paracoccus, Nocardia, Arthrobacter, Rhodopseudomonas,* or *Pseudomonas.*

In further embodiments, the $C_1$ metabolizing bacteria is a methanotroph or a methylotroph. In specific embodiments, the $C_1$ metabolizing microorganism of the present invention is a methanotroph which is a genetically modified cell from one or more of the genera *Methylomonas, Methylobacter, Methylococcus, Methylosinus, Methylocystis, Methylomicrobium, Methanomonas,* or *Methylocella.* In other embodiments, the $C_1$ metabolizing microorganism of the present invention is a methylotroph which is a genetically modified cell from one or more of the species *Methylobacterium extorquens, Methylobacterium radiotolerans, Methylobacterium populi, Methylobacterium chloromethanicum,* or *Methylobacterium nodulans.*

In some preferred embodiments, the non-naturally occurring $C_1$ metabolizing microorganism of the present invention is a genetically modified methanotrophic bacteria, which has the ability to use methane as a carbon and energy source. Methanotrophic bacteria are classified into three groups based on their carbon assimilation pathways and internal membrane structure: type I (gamma proteobacteria), type II (alpha proteobacteria), and type X (gamma proteobacteria). In some embodiments, the non-naturally occurring $C_1$ metabolizing microorganism of the present invention is a genetically modified Type I methanotroph. In certain specific embodiments, the non-naturally occurring $C_1$ metabolizing microorganism of the present invention is a genetically modified Type II methanotroph. Type I methanotrophs use the ribulose monophosphate (RuMP) pathway for carbon assimilation whereas type II methanotrophs use the serine pathway. The non-naturally occurring $C_1$ metabolizing microorganism of the present invention may be a genetically modified Type X methanotroph. Type X methanotrophs use the RuMP pathway but also express low levels of enzymes of the serine pathway.

The non-naturally occurring $C_1$ metabolizing microorganism of the present invention may be either a genetically modified facultative methanotroph or a genetically modified obligate methanotroph. For example, the $C_1$ metabolizing microorganism of the present invention may be a facultative methanotroph which is a genetically modified cell from one or more of the genera and/or species: *Methylocella, Methylocystis*, and *Methylocapsa* (e.g., *Methylocella silvestris, Methylocella palustris, Methylocella tundrae, Methylocystis daltona* strain SB2, *Methylocystis bryophila*, and *Methylocapsa aurea* KYG), *Methylobacterium organophilum* (ATCC 27,886), *Methylibium petroleiphilum*, or high growth variants thereof. Exemplary obligate methanotrophic bacteria include *Methylococcus capsulatus* Bath, *Methylomonas* 16a (ATCC PTA 2402), *Methylosinus trichosporium* OB3b (NRRL B-11,196), *Methylomicrobium buryatense* 5G (Taxonomy ID: 675511, *Syst. Appl. Microbiol.* 24(2):166-76 (July 2001)), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylomonas Flagellata* sp AJ-3670 (FERM P-2400), *Methylacidiphilum infernorum, Methylacidiphilum fumariolicum, Methyloacida kamchatkensis, Methylomicrobium alcaliphilum*, or high growth variants thereof.

In still further embodiments, the non-naturally occurring $C_1$ metabolizing microorganism of the present invention is a syngas metabolizing bacteria which is a genetically modified cell from one or more of the genera: *Clostridium, Moorella, Pyrococcus, Eubacterium, Desulfobacterium, Carboxydothermus, Acetogenium, Acetobacterium, Acetoanaerobium, Butyribaceterium*, or *Peptostreptococcus*. In specific embodiments, the $C_1$ metabolizing microorganism of the present invention is a syngas metabolizing bacteria from one or more of the species: *Clostridium autoethanogenum, Clostridium ljungdahli, Clostridium ragsdalei, Clostridium carboxydivorans, Butyribacterium methylotrophicum, Clostridium woodii, Clostridium neopropanologen*, or a combination thereof.

In certain other embodiments, the non-naturally occurring $C_1$ metabolizing microorganism of the present invention is a eukaryote such as a yeast which is a genetically modified cell from one or more of the genera: *Candida, Yarrowia, Hansenula, Pichia, Torulopsis*, or *Rhodotorula*.

Expression Systems and Vectors; Transformation Methods

Any of the recombinant $C_1$ metabolizing microorganisms described herein may be transformed to comprise at least one exogenous nucleic acid encoding a lactate dehydrogenase to provide the host with a new lactate dehydrogenase or enhanced lactate dehydrogenase activity or may be genetically modified to remove or substantially reduce an endogenous gene function using any of a variety of methods known in the art.

A number of expression systems and expression vectors useful for the expression of heterologous nucleic acids in $C_1$ metabolizing microorganisms are known in the art. In certain embodiments, the exogenous nucleic acid molecule encoding an lactic dehydrogenase is operatively linked to an expression control sequence, such as, for example, a promoter.

Promoters suitable for use in the practice of the present invention may be constitutive, leaky, or inducible, and native or non-native to the host cell employed. Exemplary promoters include a pyruvate decarboxylase (PDC) a promoter, a deoxy-xylulose phosphate synthase promoter, a methanol dehydrogenase promoter (MDH) (such as, for example, the promoter in the upstream intergenic region of the mxaF gene from *Methylococcus capsulatus* Bath (Acc. No. MCA0779) or the MDH promoter from *M. extorquens* (See Springer et al., *FEMS Microbiol. Lett.* 160:119 (1998)), a hexulose 6-phosphate synthase promoter, a ribosomal protein S16 promoter, a serine hydroxymethyl transferase promoter, a serine-glyoxylate aminotransferase promoter, a phosphoenolpyruvate carboxylase promoter, a T5 promoter, Trc promoter, a promoter for PHA synthesis (Foellner et al., *Appl. Microbiol. Biotechnol.* 40:284, 1993), a pyruvate decarboxylase promoter (Tokuhiro et al., *Appl. Biochem. Biotechnol.* 131:795, 2006), the lac operon Plac promoter (Toyama et al., *Microbiol.* 143:595, 1997), a hybrid promoter such as Ptrc (Brosius et al., *Gene* 27:161, 1984), promoters identified from native plasmid in methylotrophs (EP 296484), methanotrophs, and the like.

Additionally, suitable homologous or heterologous promoters for high expression of exogenous nucleic acid molecules may be utilized. For example, U.S. Pat. No. 7,098, 005 describes the use of promoters for high expression in the presence of methane or methanol of a heterologous coding nucleic acid in $C_1$ metabolizing bacteria.

In certain embodiments, regulated expression of exogenous nucleic acids encoding one or more lactate biosynthesis enzymes may be desirable to optimize growth rate of the non-naturally occurring methanotrophic bacteria and may improve bacterial growth in a variety of carbon source conditions. This may be achieved through the use of an inducible promoter system.

In certain embodiments, a nucleic acid encoding LDH is operatively linked to an inducible promoter. Inducible promoter systems employed in the practice of the present invention include those known in the art and include tetracycline inducible promoter system; IPTG/lac operon inducible promoter system, heat shock inducible promoter system; metal-responsive promoter systems; nitrate inducible promoter system; light inducible promoter system; ecdysone inducible promoter system, the inducible/regulatable system described for use in methylotrophic and methanotrophic bacteria (see, e.g., U.S. Patent Appl. No. US 2010/0221813, which is incorporated herein by reference), and the like. For example, in one embodiment, the non-naturally occurring $C_1$ metabolizing microorganism (e.g., methanotroph, methylotroph) comprises: (1) an exogenous nucleic acid encoding LDH, operatively linked to a promoter flanked by lacO operator sequences, and (2) an exogenous nucleic acid encoding a lad repressor protein operatively linked to a constitutive promoter (e.g., hexulose-6-phosphate synthase promoter). Induction is initiated when Lad repressor protein binds to lacO operator sequences flanking the LDH or other promoter, preventing transcription. IPTG binds lad repressor and releases it from lacO sequences, allowing transcription. By using an inducible promoter system, lactate synthesis may be controlled by the addition of an inducer.

The expression systems and expression vectors employed in the practice of the present invention optionally contain genetic elements, such as, for example, one or more ribosome binding sites for translation intiation and a transcription termination site, polyadenylation signals, restriction enzyme sites, multiple cloning sites, other coding segments, and the like.

Expression systems and vectors employed in the practice of the present invention may further contain genetic elements that facilitate integration by either homologous or non-homologous recombination. Genetic elements that facilitate integration by homologous recombination have sequence homology to targeted integration sites in the genomic sequence of the desired host cell. Genetic elements or techniques which facilitate integration by non-homologous recombination include restriction enzyme-mediated integration (REMI) (see Manivasakam et al., *Mol. Cell Biol.* (1998) 18(3):1736-1745, which is incorporated herein by reference), transposon-mediate integration, and other elements and methods that are well known in the art.

Recombinant methods for expression of exogenous or heterologous nucleic acids in microbial organisms are well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999), which are incorporated herein by reference.

In certain embodiments, the strength and timing of expression of the lactic dehydrogenases may be modulated using methods known in the art to improve lactate production. For example, varying promoter strength or nucleic acid copy number may be used to modulate expression levels. In another example, timing of expression may be modulated by using inducible promoter systems or polycistronic operons. For example, expression of LDH may occur during growth phase and stationary phase of culture or during stationary phase only. In another example, LDH may undergo ordered co-expression with other genes of interest.

Introduction of the exogenous LDH-encoding nucleic acid into the host cell can be achieved in a variety of ways that are known in the art. For example, electroporation of $C_1$ metabolizing bacteria has been previously described in, for example, Toyama et al., *FEMS Microbiol. Lett.* 166:1, 1998; Kim and Wood, *Appl. Microbiol. Biotechnol.* 48:105, 1997; Yoshida et al., *Biotechnol. Lett.* 23:787, 2001, and U.S. Patent Appl. Pub. No. 2008/0026005.

Bacterial conjugation, which refers to a particular type of transformation involving direct contact of donor and recipient cells, is more frequently used for the transfer of nucleic acids into $C_1$ metabolizing microorganisms. Bacterial conjugation involves mixing "donor" and "recipient" cells together in close contact with each other. Conjugation occurs by formation of cytoplasmic connections between donor and recipient bacteria, with unidirectional transfer of newly synthesized donor nucleic acid molecules into the recipient cells. A recipient in a conjugation reaction is any cell that can accept nucleic acids through horizontal transfer from a donor bacterium. A donor in a conjugation reaction is a bacterium that contains a conjugative plasmid, conjugative transposon, or mobilized plasmid. The physical transfer of the donor plasmid can occur through a self-transmissible plasmid or with the assistance of a "helper" plasmid. Conjugations involving $C_1$ metabolizing bacteria have been previously described in Stolyar et al., *Mikrobiologiya* 64:686, 1995; Motoyama et al., *Appl. Micro. Biotech.* 42:67, 1994; Lloyd et al., *Arch. Microbiol.* 171:364, 1999; PCT Publication No. WO 02/18617; and Ali et al., *Microbiol.* 152:2931, 2006.

Expression of heterologous nucleic acids in $C_1$ metabolizing bacteria is known in the art (see, e.g., U.S. Pat. No. 6,818,424, U.S. Patent Appl. Pub. No. 2003/0003528). Mu transposon based transformation of methylotrophic bacteria has been described (Akhverdyan et al., *Appl. Microbiol. Biotechnol.* 91:857, 2011). A mini-Tn7 transposon system for single and multicopy expression of heterologous nucleic acids without insertional inactivation of host genes in *Methylobacterium* has been described (U.S. Patent Appl. Pub. No. 2008/0026005).

Further genetic modifications to the $C_1$ metabolizing microorganism may be desired as described herein, which can be imparted using known methods. For example, various methods for inactivating, knocking-out, or deleting endogenous gene function in $C_1$ metabolizing bacteria may be used. Allelic exchange using suicide vectors to construct deletion/insertional mutants in slow growing $C_1$ metabolizing bacteria have also been described in, for example, Toyama and Lidstrom, *Microbiol.* 144:183, 1998; Stolyar et al., *Microbiol.* 145:1235, 1999; Ali et al., *Microbiol.* 152:2931, 2006; Van Dien et al., *Microbiol.* 149:601, 2003.

$C_1$ Metabolizing Microorganisms—Recombinant

As described hereinabove, the $C_1$ metabolizing microorganisms of this disclosure are recombinantly modified to include exogenous nucleic acids that express or over-express the lactate dehydrogenase(s) of interest, resulting in recombinant microorganisms useful for producing lactate. In certain embodiments, the present disclosure provides non-naturally occurring methanotrophic bacteria comprising an exogenous nucleic acid encoding a lactate dehydrogenase (LDH), wherein the methanotrophic bacteria are capable of converting a carbon feedstock into lactate. Typically, the carbon feedstock is methane, Exogenous nucleic acids employed in the practice of the present invention may encode a naturally occurring or otherwise known lactate dehydrogenase, or a sequence- or truncation-variant of such corresponding parental lactate dehydrogenase. Such encoded lactate dehydrogenase variants may exhibit improved solubility, expression, stability, catalytic activity, turnover rate or any combination thereof or may be conservatively modified variants of known lactate dehydrogenase sequences, and the lactate dehydrogenase sequences described herein.

Exogenous nucleic acids encoding a lactate dehydrogenase suitable for use in the practice of the present invention include wildtype nucleic acid sequences encoding LDHs as well as variants thereof. The term "nucleic acid variant" refers herein to a nucleic acid that may contain one or more substitutions, additions, deletions, insertions, or may be or comprise fragment(s) of a reference nucleic acid. A reference nucleic acid refers to a selected wild-type (parent nucleic acid) encoding a particular LDH enzyme (e.g., LdhA). Due to redundancy in the genetic code, nucleic acid variants may or may not affect amino acid sequence.

Typically, exogenous LDH-encoding nucleic acids to be introduced into a host as described herein are subjected to codon optimization prior to introduction into the host to ensure protein expression is effective or enhanced. Codon optimization refers to alteration of codons in nucleic acids or coding regions of nucleic acids before transformation to reflect the typical codon usage of the host without altering the polypeptide encoded by the non-natural DNA molecule. Codon optimization methods for optimum nucleic acid expression in heterologous hosts have been previously described (see, e.g., Welch et al., *PLoS One* 4:e7002, 2009; Gustafsson et al., *Trends Biotechnol.* 22:346, 2004; Wu et al., *Nucl. Acids Res.* 35:D76, 2007; Villalobos et al., *BMC*

*Bioinformatics* 7:285, 2006; U.S. Patent Publication Nos. 2011/0111413 and 2008/0292918; disclosure of which are incorporated herein by reference, in their entirety).

A nucleic acid variant may encode an LDH amino acid sequence comprising one or more conservative substitutions compared to a corresponding parental LDH amino acid sequence. A conservative substitution may occur naturally in the polypeptide (e.g., naturally occurring genetic variants) or may be introduced when the polypeptide is recombinantly produced.

Suitable exogenous nucleic acids encoding an LDH that may be employed in the practice of the present invention include nucleic acids encoding an LDH from other organisms (i.e., lactate dehydrogenases and/or lactate dehydrogenase encoding nucleic acids that are not native to the host $C_1$ microorganism). Such exogenous nucleic acid may encode any of a number of LDH amino acid sequences that are known in the art. In addition, the corresponding LDH encoding nucleic acids which have been isolated and cloned from a number of these organisms, such as, for example, from bacteria, plants, yeast, fungi, and animals, may be suitable for use in the practice of the present invention. With the complete genome sequence available for hundreds of organisms, the identification of nucleic acids encoding lactate dehydrogenase in related or distant species, including for example, homologs, orthologs, paralogs, etc., is well known in the art. These may be codon optimized for optimal expression from the desired $C_1$ metabolizing microorganism using known methods.

In certain embodiments, the exogenous nucleic acid molecule encodes a D- or L-LDH from *Actinomyces viscosus, Acinonyx jubatus, Archilochus colubris, Bacillus anthracis, Bacillus caldolyticus, Bacillus coagulans, Bacillus megaterium, Bacillus stearothermophilus* (Q9p4b6) (also known as *Geobacillus stearothermophilus*), *Bacillus subtilis, Bacillus thuringiensis, Bacteroides pectinophilus, Bifidobacterium longum, Bos taurus, Canis familiaris, Canis lupus, Deinococcus radiodurans, Enterococcus faecalis, Enterococcus faecium, Equus ferus, Felis catus, Kluyveromyces lactis, Kluyveromyces maxxianus, Lactobacillus acidophilus, Lactobacillus bulgaricus, Lactobacillus casei, Lactobacillus coryniformis sp. torquens, Lactobacillus delbrueckii* (including subsp. *bulgaricus*), *Lactobacillus fermentum, Lactobacillus helveticus, Lactobacillus johnsonii, Lactobacillus pentosus, Lactobacillus plantarum, Lactobaillus plantaum, Lactobacillus rhamnosus, Lactococcus lactis, Leuconostoc mesenteroides, Listeria monocytogenes, Lysteria marthii, Plasmodium falciparum, Plasmodium ovale, Thermus thermophilus, Mus musculus, Oryctolagus cuniculus, Pediococcus acidilactici, Taeniopygia guttata, Rattus norvegicus, Rhizopus oryzae, Staphylococcus aureus, Streptococcus bovis, Streptococcus pasteurianus, Ruminococcus torques, Staphylococcus simiae, Staphylococcus vitulinus, Staphylococcus lentus, Macrococcus caseolyticus, Bacillus thuringiensis* seovar *konkukian* str. 97-27, *Bacillus thuringiensis* serovar *chinensis* CT-43, *Bacillus mycoides*, and the like.

In some embodiments, the exogenous nucleic acid encodes a D-lactate dehydrogenase. The sequences of many D-lactate dehydrogenases are known in the art. Illustrative exogenous nucleic acids employed in the practice of the present invention which encode a D-lactate dehydrogenase include those which encode a D-LDH from *Lactobacillus delbrueckii, Lactobacillus plantaum, Lactobacillus johnsonii, Leuconostoc mesenteroides* (see e.g., JP 2002-136263A and US 2007/0105202 (SEQ ID NO:2), both of which are incorporated herein by reference); and *Lactobacillus helveticus* (see e.g., WO 2003/102201, which is incorporated herein by reference). Typically, the exogenous LDH-encoding nucleic acid is codon optimized for optimal expression from the specific host cell employed.

In some cases, the non-naturally occurring $C_1$ metabolizing microorganism comprises an exogenous nucleic acid that encodes a D-LDH that has at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% sequence identity to a reference ("parental LDH") amino acid sequence selected from the group consisting of SEQ ID NOs:64 and 66, or an N- or C-terminally truncated variant thereof, wherein the encoded LDH comprises D-LDH activity, or wherein the non-naturally occurring $C_1$ metabolizing microorganism comprising such exogenous nucleic acid produces D-lactate (as determined, for example, using the method of Example 1 and substituting the EnzyFluo™ D-Lactate Assay Kit (Catalog No. EFDLC-100, BioAssay Systems, Hayward, Calif. 94545) for the EnzyFluo™ L-Lactate Assay Kit in the method). In some embodiments, the encoded D-LDH retains at least 50% of the D-LDH activity as compared to the parental LDH. Typically, the non-naturally occurring $C_1$ metabolizing microorganism comprising an exogenous nucleic acid encoding such D-LDH is capable of producing more lactate as compared to that of a corresponding reference $C_1$ metabolizing microorganism, when cultured in the presence of a $C_1$ substrate under at least one set of culture conditions. In some embodiments that non-naturally occurring $C_1$ metabolizing microorganism comprises an exogenous nucleic acid encoding a D-LDH having a sequence selected from the group consisting of SEQ ID NO:65 and 67, or an N- or C-terminally truncated variant thereof. In specific embodiments, the exogenous nucleic acid encodes a D-LDH having an amino acid sequence corresponding to SEQ ID N:64 or SEQ ID NO:66.

In other embodiments, the non-naturally occurring $C_1$ metabolizing microorganism comprises an exogenous nucleic acid encoding a D-LDH, wherein the exogenous nucleic acid has a nucleic acid sequence that is at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity to a nucleic acid sequence selected from the group consisting of SEQ ID NOs:64 and 66, wherein the encoded LDH comprises D-LDH activity, or wherein the non-naturally occurring $C_1$ metabolizing microorganism comprising such exogenous nucleic acid produces D-lactate (as determined, for example, using the method of Example 1 and substituting the EnzyFluo™ D-Lactate Assay Kit (Catalog No. EFDLC-100, BioAssay Systems, Hayward, Calif. 94545) for the EnzyFluo™ L-Lactate Assay Kit in the method). In some embodiments, the encoded D-LDH retains at least 50% of the D-LDH activity as compared to the parental LDH. Typically, the non-naturally occurring $C_1$ metabolizing microorganism comprising an exogenous nucleic acid encoding such D-LDH is capable of producing more lactate as compared to that of a corresponding reference $C_1$ metabolizing microorganism, when cultured in the presence of a $C_1$ substrate under at least one set of culture conditions.

In certain embodiments, the exogenous nucleic acid has a sequence corresponding to SEQ ID NO:64 or SEQ ID NO:66. In certain of these embodiments, the non-naturally occurring $C_1$ metabolizing microorganism comprising such exogenous nucleic acid is capable of producing more lactate as compared to that of the corresponding reference $C_1$ microorganism, when cultured in the presence of a $C_1$ substrate under at least one set of culture conditions.

In further embodiments, the non-naturally occurring $C_1$ metabolizing microorganism comprises an exogenous nucleic acid encoding a L-LDH. Exemplary L-LDH nucleic acids include those corresponding to Accession Nos. AEEL01000014.1 (region 176996 to 177985) (*Streptococcus bovis*), NC_010080.1 (region 957682 to 958608) (*Lactobacillus helveticus*), BC146210.1 (*Bos taurus*), AB776697.1 (*Pediococcus acidilactici*), EF152288.1 (*Rhizopus oryzae*), NC_013198.1 (region 619708 to 620646) (*Lactobacillus rhamnosus*), NC_010610.1 (region 417799 to 418740) (*Lactobacillus fermentum*), NC_008054.1 (region 99905 to 100828) (*Lactobacillus delbrueckii*), NC_002662.1 (region 1369224 to 1370201) (*Lactococcus lactis*), and NC_004668.1 (region 231275 to 232258) (*Enterococcus faecalis*). For example, the exogenous nucleic acids employed in the practice of the present invention may encode any of the following exemplary polypeptide sequences of L-LDH: Accession Nos. EFM27433.1 (*Streptococcus bovis*), YP_001577351.1 (*Lactobacillus helveticus*), AAI46211.1 (*Bos taurus*), BAM76361.1 (*Pediococcus acidilactici*), ABL84845.1 (*Rhizopus oryzae*), YP_003170352.1 (*Lactobacillus rhamnosus*), YP_001843164.1 (*Lactobacillus fermentum*), YP_618317.1 (*Lactobacillus delbrueckii*), NP_267487.1 (*Lactococcus lactis*), NP_814049.1 (*Enterococcus faecalis*); SEQ ID NOs:52 (*Staphylococcus simiae* CCM 7213), 53 (*Staphylococcus vitulinus* F1028), 54 (*Staphylococcus lentus* F1142), 55 (*Macrococcus caseolyticus* JCSC5402), 56 (*Bacillus thuringiensis* serovar *konkukian* str. 97-27), 57 (*Bacillus thuringiensis* serovar *chinensis* CT-43), and 58 (*Bacillus mycoides* DSM 2048).

In some embodiments, the non-naturally occurring $C_1$ metabolizing microorganism comprises an exogenous nucleic acid that encodes an L-LDH having at least about 50%, at least about 55%, at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, and at least about 99% sequence identity to a reference amino acid sequence selected from the group consisting of SEQ ID NOs:2, 4, 6, 8, 10, 12, 14, 16, 18, 20, 22, 24, 26, 28, 30, 32, 34, 36, 38, 40, 42, 44, 46, 48, 53, 54, 55, 56, 57, 58, 59 and an N- and C-terminally truncated variant thereof, wherein the encoded LDH comprises L-LDH activity, or wherein the non-naturally occurring $C_1$ metabolizing microorganism comprising such exogenous nucleic acid produces L-lactate (as determined, for example, using the method of Example 1). In some embodiments, the encoded L-LDH retains at least 50% of the L-LDH activity as compared to the parental LDH. Typically, the non-naturally occurring $C_1$ metabolizing microorganism comprising an exogenous nucleic acid encoding such L-LDH is capable of producing more lactate as compared to that of a corresponding reference $C_1$ metabolizing microorganism, when cultured in the presence of a $C_1$ substrate under at least one set of culture conditions.

In some embodiments, the reference amino acid sequence is selected from the group consisting of SEQ ID NOs:2, 8, 10, 12, 14, 16, 18, 20, 22, 24, 26, 28, 30, 32, 34, 36, 38, 40, 42, 44, and 48. In certain embodiments, the reference amino acid sequence is selected from the group consisting of SEQ ID NOs:34, 16, and 24. Exemplary exogenous nucleic acids include those which encode an L-LDH having an amino acid sequence selected from the group consisting of SEQ ID NOs:2 (*Streptococcus pasteurianus* LDH), 4 (*Lactobacillus helveticus* LDH), 6 (*Bos taurus* LDH variant), 8 (*Ruminococcus torques* LDH), 10 (*Rhizopus oryzae* LDH), 12 (*Enterococcus faecalis* LDH), 14 (*Lactobacillus casei* LDH), 16 (*Bacillus megaterium* LDH), 18 (*Taeniopygia guttata* LDH), 20 (*Lactobacillus plantarum* LDH), 22 (*Lactobacillus acidophilus* LDH), 24 (*Staphylococcus aureus* LDH), 26 (*Bacillus caldolyticus* LDH), 28 (*Actinomyces viscosus* LDH), 30 (*Bacillus anthracis* LDH), 32 (*Bacteroides pectinophilus* LDH), 34 (*Listeria marthii* LDH), 36 (*Bacillus subtilis* LDH), 38 (*Enterococcus faecium* LDH), 40 (*Bacillus thuringiensis* LDH), 42 (*Geobacillus stearothermophilus* LDH), 44 (*Deinococcus radiodurans* LDH), 46 (*Plasmodium ovale* LDH variant), 48 (*Thermus thermophilus* LDH), 53 (*Staphylococcus simiae* CCM 7213), 54 (*Staphylococcus vitulinus* F1028), 55 (*Staphylococcus lentus* F1142), 56 (*Macrococcus caseolyticus* JCSC5402), 57 (*Bacillus thuringiensis* serovar *konkukian* str. 97-27), 58 (*Bacillus thuringiensis* serovar *chinensis* CT-43), 59 (*Bacillus mycoides* DSM 2048), and N- and C-terminally truncated variant thereof. In some embodiments, the exogenous nucleic acid encodes an L-LDH having an amino acid sequence selected from the group consisting of SEQ ID NOs:2, 8, 10, 12, 14, 16, 18, 20, 22, 24, 26, 28, 30, 32, 34, 36, 38, 40, 42, 44, and 48. In other embodiments, the exogenous nucleic acid encodes an L-LDH having an amino acid sequence selected from the group consisting of SEQ ID NOs:34, 16, and 24.

In other embodiments, the non-naturally occurring $C_1$ metabolizing microorganism comprises an exogenous nucleic acid encoding a L-LDH, wherein the exogenous nucleic acid has a nucleic acid sequence that is at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to a reference nucleic acid sequence selected from the group consisting of SEQ ID NOs:1, 3, 5, 7, 9, 11, 13, 15, 17, 19, 21, 23, 25, 29, 31, 33, 35, 37, 39, 41, 43, 45, and 47, wherein the encoded LDH comprises L-LDH activity, or wherein the non-naturally occurring $C_1$ metabolizing microorganism comprising such exogenous nucleic acid produces L-lactate (as determined, for example, using the method of Example 1). In some embodiments, the encoded L-LDH retains at least 50% of the L-LDH activity as compared to the parental LDH. Typically, the non-naturally occurring $C_1$ metabolizing microorganism comprising an exogenous nucleic acid encoding such L-LDH is capable of producing more lactate as compared to that of a corresponding reference $C_1$ metabolizing microorganism, when cultured in the presence of a $C_1$ substrate under at least one set of culture conditions.

In certain embodiments, the reference nucleic acid sequence is selected from the group consisting of SEQ ID NOs:1, 7, 9, 11, 13, 15, 17, 19, 21, 23, 25, 27, 29, 31, 33, 35, 37, 39, 41, 43, and 47. In other embodiments, the exogenous nucleic acid encodes a reference nucleic acid sequence selected from the group consisting of SEQ ID NOs:33, 15, and 23. Illustrative exogenous nucleic acids encoding an L-LDH include those having a nucleic acid sequence selected from the group consisting of 1, 3, 5, 7, 9, 11, 13, 15, 17, 19, 21, 23, 25, 29, 31, 33, 35, 37, 39, 41, 43, 45, and 47. In some embodiments, the exogenous nucleic acid encoding an L-LDH comprises a nucleic acid sequence selected from the group consisting of 1, 7, 9, 11, 13, 15, 17, 19, 21, 23, 25, 27, 29, 31, 33, 35, 37, 39, 41, 43, and 47. In certain specific embodiments, the exogenous nucleic acid encoding an L-LDH comprises a nucleic acid sequence selected from the group consisting of SEQ ID NOs:33, 15, and 23.

Typically, truncation variants of the encoded LDHs described herein encode a corresponding reference (i.e., parental or sequence variant thereof) LDH that has been N-terminally truncated by from about 1 to about 6 amino acid residues (or from about 1 to about 5 amino acid residues, or from about 1 to about 4 amino acid residues, or from about 1 to about 3 amino acid residues, or from 1 to about 2 amino acid residues, or which is N-terminally truncated by 1 amino acid residue), and/or C-terminally truncated by from about 1 to about 30 amino acid residues (or from about 1 to about 25, about 20, about 15, about 10, or about 5 amino acid residues).

In certain embodiments of the non-naturally occurring $C_1$ metabolizing microorganisms described herein, the non-naturally occurring $C_1$ metabolizing microorganism is capable of producing at least about 1.5 times more lactate as compared to that of a corresponding reference $C_1$ metabolizing microorganism when cultured in the presence of a $C_1$ substrate (e.g., methane) under at least one set of culture conditions. In other embodiments, the non-naturally occurring $C_1$ metabolizing microorganism is capable of producing at least about 2 times, at least about 3 times, at least about 5 times, at least about 10 times, at least about 50 times, at least about 100 times, at least about 500 times, at least about 1000 times, and up to about 15,000 times or up to about 20,000 times more lactate as compared to that of a corresponding reference $C_1$ metabolizing microorganism when cultured in the presence of a $C_1$ substrate (e.g., methane) under at least one set of culture conditions.

Methods for generating exogenous nucleic acids that encode LDH variants may be designed using the phylogenetic-based methods described in the references noted above (U.S. Pat. No. 8,005,620; Gustafsson; Welch et al.; Villalobos et al.; Minshull et al.). Each LDH variant generated by these methods will retain at least 50% activity (preferably 100% or more activity) and have a polypeptide sequence that is at least 90%, at least 91%, at least 92%, at least 93%, at least 94%, at least 95%, at least 96%, at least 97%, at least 98%, at least 99% identical, or 100% identical to a reference or parental wild-type polypeptide sequence. In certain embodiments, the encoded LDH variants will include at least one amino acid substitution (e.g., 1, 2, 3, 5, 6, 7, 8, 9 or 10 or more or up to 20, 25, or 30 substitutions) at a pre-determined position relative to a reference or parental wild-type enzyme, provided that a variant retains lactate dehydrogenase activity (e.g., L- or D-lactate dehydrogenase activity or L- or D-lactate production). Exemplary assays for determining D- and L-lactate dehydrogenase activity are described herein.

In some embodiments, the non-naturally occurring $C_1$ metabolizing microorganism of the present invention comprises two or more nucleic acids, each encoding a lactate dehydrogenase, wherein the sequences of the nucleic acids and/or the sequences of the LDHs may be the same or different. In certain embodiments, multiple copies of an LDH encoding nucleic acid are introduced into a host cell, which may be two, three, four, five, six, seven, eight, nine, ten or more copies of the same LDH or different LDH encoding nucleic acids. When two or more exogenous nucleic acid molecules are introduced into a host $C_1$ metabolizing microorganism, it is understood that the two more exogenous nucleic acid molecules can be introduced as a single nucleic acid molecule (e.g., on a single vector), on separate vectors, integrated into the host chromosome at a single site or multiple sites, and each of these embodiments is still to be considered two or more exogenous nucleic acid molecules. For example, more than one heterologous or exogenous nucleic acid molecules can be introduced into a host cell, e.g., as separate nucleic acid molecules, as a polycistronic nucleic acid molecule, as a single nucleic acid molecule encoding a fusion protein, or any combination thereof, and still be considered as more than one heterologous or exogenous nucleic acid.

In certain embodiments, the exogenous nucleic acid is introduced into a host cell by conjugation, transformation, transfection, electroporation, or the like, wherein the added molecule may integrate into the host genome or can exist as extra-chromosomal genetic material (e.g., as a plasmid or other self-replicating vector).

In certain embodiments, the non-naturally occurring $C_1$ metabolizing microorganisms of the present invention further comprise additional genetic modifications. For example, a heterologous control sequence (e.g., promoter, enhancer) may be used to regulate expression of a native gene or nucleic acid in a way that is different from the way a native gene or nucleic acid is normally expressed in nature or culture. Other genetic modifications may be made, such as, for example, to reduce or inhibit endogenous pyruvate decarboxylase, methylglyoxal synthase, LDH (e.g., aerobic LDH, D-LDH), glycogen synthase, phosphoglucomutase, or any combination thereof to augment lactate production, lactate yield, or both. In such embodiments, non-natural $C_1$ metabolizing microorganisms (e.g., non-natural methanotrophic bacteria) comprising an exogenous nucleic acid encoding LDH as provided herein will have a deleted or mutated endogenous pyruvate decarboxylase gene such that the pyruvate decarboxylase activity is minimal to undetectable. In certain embodiments, non-natural $C_1$ metabolizing microorganisms (e.g., non-natural methanotrophic bacteria) comprising an exogenous nucleic acid encoding LDH as provided herein will have a deleted or mutated endogenous nucleic acid encoding methylglyoxal synthase or other methylglyoxal bypass pathway enzyme such that the methylglyoxal bypass pathway has minimal to undetectable activity to minimize accumulation of methylglyoxal (a toxic byproduct).

In certain embodiments, non-natural $C_1$ metabolizing microorganisms (e.g., non-natural methanotrophic bacteria) comprising an exogenous nucleic acid encoding an LDH as provided herein will have a deleted or mutated endogenous D-LDH to minimize or avoid synthesis of a racemic mixture of D-lactate and L-lactate, wherein the non-natural $C_1$ metabolizing microorganism produces L-lactate. In certain embodiments, non-natural $C_1$ metabolizing microorganisms (e.g., non-natural methanotrophic bacteria) are transformed with two, three, four, five, six, seven, eight, nine, ten or more copies of an exogenous nucleic acid molecule encoding LDH. In further embodiments, non-natural $C_1$ metabolizing microorganisms (e.g., non-natural methanotrophic bacteria) comprising an exogenous nucleic acid molecule encoding LDH as provided herein overexpress LDH at two, three, four, five, six, seven, eight, or more fold as compared to the normal expression level of endogenous LDH.

Non-naturally occurring $C_1$ metabolizing microorganisms (e.g., methanotrophs, methylotrophs) of the present invention may also be engineered to comprise variant lactate biosynthetic pathways or enzymes. Variation in lactate synthesis may occur at one or more individual steps of a pathway or involve an entirely new pathway. In certain embodiments, particular lactate pathway reactions are catalyzed by variant or alternative lactate enzymes, which may be in combination with inhibiting or knocking out pyruvate decarboxylase activity, alcohol dehydrogenase activity, one or more methylglyoxal bypass pathway enzymes, D-LDH, glycogen synthase, phosphoglucomutase, or any combination thereof. In certain embodiments, hybrid pathways with nucleic acids derived from two or more sources are used to enhance lactate production, yield, or both.

Various methods for inhibiting, inactivating, knocking-out, or deleting endogenous gene function in methanotrophic bacteria are known in the art. For example, targeted gene disruption is an effective method for gene down-regulation where an exogenous nucleic acid is inserted into a structural gene to disrupt transcription. Genetic cassettes comprising the exogenous insertion DNA (e.g., a genetic marker) flanked by sequence having a high degree of sequence homology to a portion of the target host gene to be disrupted are introduced into host methanotrophic bacteria. Exogenous DNA disrupts the target host gene via native DNA replication mechanisms. Allelic exchange to construct deletion/insertional mutants in $C_1$ metabolizing microorganisms, including methanotrophic bacteria, have been described in, for example, Toyama and Lidstrom, *Microbiol.* 144:183, 1998; Stolyar et al., *Microbiol.* 145:1235, 1999; Ali et al., *Microbiol.* 152:2931, 2006; Van Dien et al., *Microbiol.* 149:601, 2003; Martin and Murrell, *FEMS Microbiol. Lett.* 127:243, 2006. Culture Methods Methods of Producing Lactate Methods are provided herein for producing lactate, comprising culturing a non-naturally occurring $C_1$ metabolizing microorganism (e.g., methanotroph, methylotroph) comprising an exogenous nucleic acid encoding lactate dehydrogenase in the presence of a carbon feedstock under conditions sufficient to produce lactate. Typically, the carbon feedstock is selected from the group consisting of methane, methanol, syngas, and natural gas. More typically the carbon feedstock is selected from the group consisting of methane and natural gas. Methods for growth and maintenance of methanotrophic bacterial cultures are well known in the art. Various embodiments of non-naturally occurring methanotrophic bacteria described herein may be used in the methods of producing lactate, such as L-lactic acid and salts and esters thereof.

In certain embodiments, lactate is produced during a specific phase of cell growth (e.g., lag phase, log phase, stationary phase, or death phase). It may be desirable for carbon from feedstock to be converted to lactate rather than to growth and maintenance of $C_1$ metabolizing microorganism. In some embodiments, non-naturally occurring $C_1$ metabolizing microorganism (e.g., methanotrophs, methylotrophs) as provided herein are cultured to a low to medium cell density ($OD_{600}$) and then production of lactate is initiated. In some embodiments, lactate is produced while the $C_1$ metabolizing microorganism (e.g., methanotrophic bacteria) are no longer dividing or dividing very slowly. In some embodiments, lactate is produced only during stationary phase. In some embodiments, lactate is produced during log phase and stationary phase.

The fermenter composition comprising lactate produced by non-naturally occurring $C_1$ metabolizing microorganism (e.g., methanotrophs, methylotrophs) provided herein may further comprise other organic compounds associated with biological fermentation processes. For example, biological by-products of fermentation may include one or more of alcohols, epoxides, aldehydes, ketones, esters, or a combination thereof. In certain embodiments, the fermenter composition may contain one or more of the following alcohols: methanol, ethanol, butanol, or propanol. Other compounds, such as $H_2O$, CO, $CO_2$, CO $N_2$, $H_2$, $O_2$, and unutilized carbon feedstocks, such as methane, ethane, propane, and butane, may also be present in the fermenter off-gas.

Conditions sufficient to produce lactate include culturing the non-naturally occurring $C_1$ metabolizing microorganism at a temperature in the range of about 25° to about 50° C. In some embodiments, the culture temperature is in the range of about 37° to about 50° C., and may be in the range of about 37° C. to about 45° C. Other conditions sufficient to produce lactate include culturing the non-naturally occurring $C_1$ metabolizing microorganism at a pH in the range of about 6 to about 9, and often in the range of about 7 to about 8.

In certain embodiments, non-naturally occurring $C_1$ metabolizing microorganism (e.g., methanotrophs, methylotrophs) provided herein produce lactate at about 0.001 g/L of culture to about 500 g/L of culture. In some embodiments, the amount of lactate produced is about 1 g/L of culture to about 100 g/L of culture. In some embodiments, the amount of lactate produced is about 0.001 g/L, 0.01 g/L, 0.025 g/L, 0.05 g/L, 0.1 g/L, 0.15 g/L, 0.2 g/L, 0.25 g/L, 0.3 g/L, 0.4 g/L, 0.5 g/L, 0.6 g/L, 0.7 g/L, 0.8 g/L, 0.9 g/L, 1 g/L, 2.5 g/L, 5 g/L, 7.5 g/L, 10 g/L, 12.5 g/L, 15 g/L, 20 g/L, 25 g/L, 30 g/L, 35 g/L, 40 g/L, 45 g/L, 50 g/L, 60 g/L, 70 g/L, 80 g/L, 90 g/L, 100 g/L, 125 g/L, 150 g/L, 175 g/L, 200 g/L, 225 g/L, 250 g/L, 275 g/L, 300 g/L, 325 g/L, 350 g/L, 375 g/L, 400 g/L, 425 g/L, 450 g/L, 475 g/L, or 500 g/L.

In certain embodiments, lactate is a substantially purified liquid. Purification methods are known in the art and purity may be assessed by methods such as column chromatography, HPLC, or GC-MS analysis. In certain embodiments, lactate has at least 20%, 25%, 30%, 35%, 40%, 45%, 50%, 55%, 60%, 65%, 70%, 75%, 80%, 85%, 90%, 95%, or 99% purity by weight.

In certain embodiments, at least a portion of the gas phase that remains after one or more steps of lactate recovery is recycled back into the fermentation system.

A variety of culture methodologies may be used for recombinant methanotrophic bacteria described herein. For example, methanotrophic bacteria may be grown by batch culture or continuous culture methodologies. In certain embodiments, the cultures are grown in a controlled culture unit, such as a fermenter, bioreactor, hollow fiber membrane bioreactor, or the like.

A classical batch culturing method is a closed system where the composition of the media is set at the beginning of the culture and not subject to external alterations during the culture process. Thus, at the beginning of the culturing process, the media is inoculated with the desired $C_1$ metabolizing microorganism (e.g., methanotroph) and growth or metabolic activity is permitted to occur without adding anything to the system. Typically, however, a "batch" culture is batch with respect to the addition of carbon source and attempts are often made at controlling factors such as pH and oxygen concentration. In batch systems, the metabolite and biomass compositions of the system change constantly up to the time the culture is terminated. Within batch cultures, cells moderate through a static lag phase to a high growth logarithmic phase and finally to a stationary phase where growth rate is diminished or halted. If untreated, cells in the stationary phase will eventually die. Cells in logarithmic growth phase are often responsible for the bulk production of end product or intermediate in some systems. Stationary or post-exponential phase production can be obtained in other systems.

The Fed-Batch system is a variation on the standard batch system. Fed-Batch culture processes comprise a typical batch system with the modification that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measureable factors, such as pH, dissolved oxygen, and the partial pressure of waste gases such as $CO_2$. Batch and Fed-Batch culturing methods are common and known in the art (see, e.g., Thomas D. Brock, Biotechnology: A Textbook of Industrial Microbiology, $2^{nd}$ Ed. (1989) Sinauer Associates, Inc., Sunderland, Mass.; Deshpande, *Appl. Biochem. Biotechnol.* 36:227, 1992), which is incorporated herein by reference.

Continuous cultures are "open" systems where a defined culture media is added continuously to a bioreactor and an equal amount of conditioned media is removed simultaneously for processing. Continuous cultures generally maintain the cells at a constant high liquid phase density where cells are primarily in logarithmic phase growth. Alternatively, continuous culture may be practiced with immobilized cells where carbon and nutrients are continuously added and valuable products, by-products, and waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limited nutrient, such as the carbon source or nitrogen level, at a fixed rate and allow all other parameters to modulate. In other systems, a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art, and a variety of methods are detailed by Brock, supra.

Liquid phase bioreactors (e.g., stirred tank, packed bed, one liquid phase, two liquid phase, hollow fiber membrane) are well known in the art and may be used for growth of non-naturally occurring microorganisms and biocatalysis.

By using gas phase bioreactors, substrates for bioproduction are absorbed from a gas by non-naturally occurring microorganisms, cell lysates or cell-free fractions thereof, rather than from a liquid. Use of gas phase bioreactors with microorganisms is known in the art (e.g., U.S. Pat. Nos. 2,793,096; 4,999,302; 5,585,266; 5,079,168; and 6,143,556; U.S. Statutory Invention Registration H1430; U.S. Patent Application Publication No. 2003/0032170; *Emerging Technologies in Hazardous Waste Management III*, 1993, eds. Tedder and Pohland, pp. 411-428, all of which are incorporated herein by reference). Exemplary gas phase bioreactors include single pass system, closed loop pumping system, and fluidized bed reactor. By utilizing gas phase bioreactors, methane or other gaseous substrates is readily available for bioconversion by polypeptides with, for example, monooxygenase activity. In certain embodiments, methods for converting a gas into a lactate composition are performed in gas phase bioreactors. In further embodiments, methods for converting a gas into a lactate composition are performed in fluidized bed reactors. In a fluidized bed reactor, a fluid (i.e., gas or liquid) is passed upward through particle bed carriers, usually sand, granular-activated carbon, or diatomaceous earth, on which microorganisms can attach and grow. The fluid velocity is such that particle bed carriers and attached microorganisms are suspended (i.e., bed fluidization). The microorganisms attached to the particle bed carriers freely circulate in the fluid, allowing for effective mass transfer of substrates in the fluid to the microorganisms and increased microbial growth. Exemplary fluidized bed reactors include plug-flow reactors and completely mixed reactors. Uses of fluidized bed reactors with microbial biofilms are known in the art (e.g., Pfluger et al., *Bioresource Technol.* 102:9919, 2011; Fennell et al., *Biotechnol, Bioengin.* 40:1218, 1992; Ruggeri et al., *Water Sci. Technol.* 29:347, 1994; U.S. Pat. Nos. 4,032,407; 4,009,098; 4,009,105; and 3,846,289, all of which are incorporated herein by reference).

Methanotrophic bacteria described in the present disclosure may be grown as an isolated pure culture, with a heterologous non-methanotrophic microorganism(s) that may aid with growth, or with one or more different strains or species of methanotrophic bacteria may be combined to generate a mixed culture.

In alternative embodiments, methods described herein use recombinant $C_1$ metabolizing microorganisms of the present invention or cell lysates thereof immobilized on, within, or behind a solid matrix. In further embodiments, the non-naturally occurring $C_1$ microorganisms of the present invention, cell lysates or cell-free extracts thereof are in a substantially non-aqueous state (e.g., lyophilized). Recombinant microorganisms, cell lysates or cell-free fractions thereof are temporarily or permanently attached on, within, or behind a solid matrix within a bioreactor. Nutrients, substrates, and other required factors are supplied to the solid matrices so that the cells may catalyze the desired reactions. Recombinant microorganisms may grow on the surface of a solid matrix (e.g., as a biofilm). Recombinant microorganisms, cell lysates or cell-free fractions derived thereof may be attached on the surface or within a solid matrix without cellular growth or in a non-living state. Exemplary solid matrix supports for microorganisms include polypropylene rings, ceramic bio-rings, ceramic saddles, fibrous supports (e.g., membrane), porous glass beads, polymer beads, charcoal, activated carbon, dried silica gel, particulate alumina, Ottawa sand, clay, polyurethane cell support sheets, and fluidized bed particle carrier (e.g., sand, granular-activated carbon, diatomaceous earth, calcium alginate gel beads).

Lactate produced using the compositions and methods described herein may be further processed into other high value products using methods known in the art. For example, after recovery or purification, lactate may be changed or derivatized for various uses, such as making bioplastics.

The present invention further provides useful products, which include lactate and compositions thereof, and the non-naturally occurring $C_1$ metabolizing microorganisms of the present invention. Compositions of the present invention may be in the form of a solid (e.g., a powder) or liquid (e.g., solution, emulsion, suspension, and the like) and may comprise lactate in combination with a component selected from the group consisting of a non-naturally occurring $C_1$ metabolizing microorganism of the present invention, water, a salt, an acid, a base, a buffer, and the like.

Figure 2:
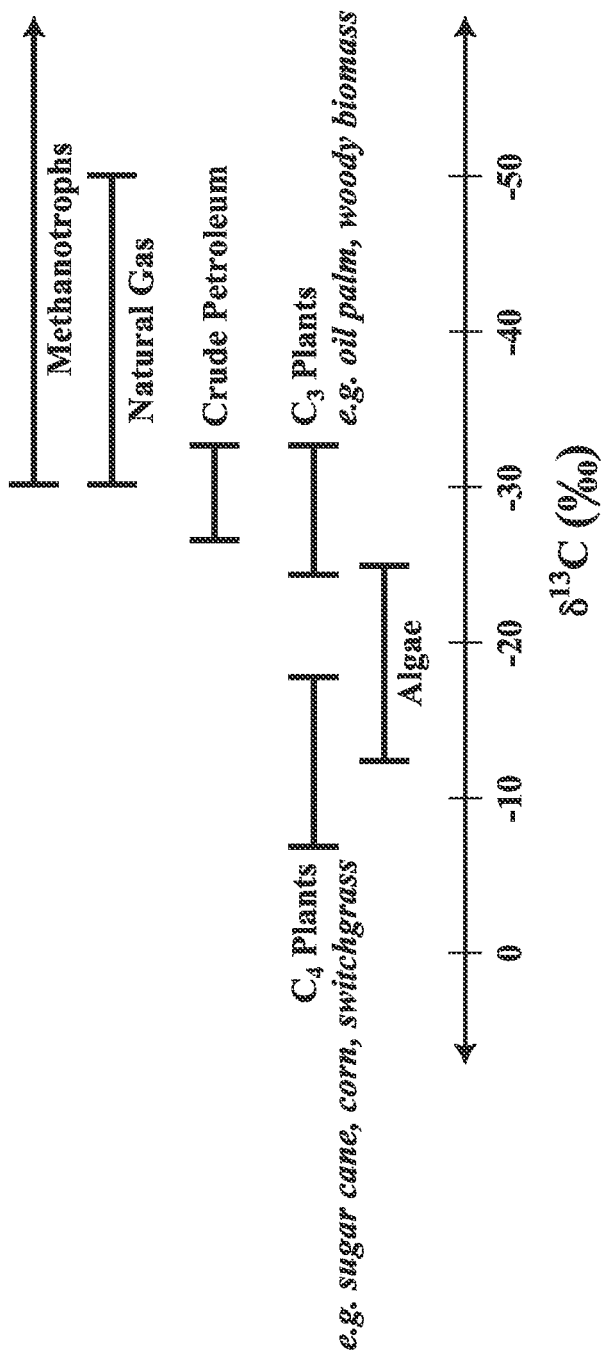
FIG. 2 depicts the $\delta^{13}C$ distribution of various carbon sources.

Lactate and compositions thereof produced using the methods provided herein may be distinguished from lactate produced from petrochemicals or from lactate biosynthesized from non-methanotrophic bacteria by carbon fingerprinting. By way of background, stable isotopic measurements and mass balance approaches are widely used to evaluate global sources and sinks of methane (see Whiticar and Faber, *Org. Geochem.* 10:759, 1986; *Whiticar, Org. Geochem.* 16: 531, 1990). A measure of the degree of carbon isotopic fractionation caused by microbial oxidation of methane can be determined by measuring the isotopic signature (i.e., ratio of stable isotopes $^{13}C:^{12}C$) value of the residual methane. For example, aerobic methanotrophs can metabolize methane through a specific enzyme, methane monoxygenase (MMO). Methanotrophs convert methane to methanol and subsequently formaldehyde. Formaldehyde can be further oxidized to $CO_2$ to provide energy to the cell in the form of reducing equivalents (NADH), or incorporated into biomass through either the RuMP or serine cycles (Hanson and Hanson, *Microbiol. Rev.* 60:439, 1996), which are directly analogous to carbon assimilation pathways in photosynthetic organisms. More specifically, a Type I methanotroph uses the RuMP pathway for biomass synthesis and generates biomass entirely from $CH_4$, whereas a Type II methanotroph uses the serine pathway that assimilates 50-70% of the cell carbon from $CH_4$ and 30-50% from $CO_2$ (Hanson and Hanson, 1996). Methods for measuring carbon isotope compositions are provided in, for example, Templeton et al. (*Geochim. Cosmochim. Acta* 70:1739, 2006), which methods are hereby incorporated by reference in their entirety. The $^{13}C/^{12}C$ stable carbon isotope ratio of lactate (reported as a $\delta^{13}C$ value in parts per thousand, ‰), varies depending on the source and purity of the $C_1$ substrate used (see, e.g., FIG. 2).

For example, lactate derived from petroleum will have a $\delta^{13}C$ distribution of about −22‰ to about −24‰. Lactate biosynthesized primarily from corn-derived glucose ($\delta^{13}C$ −10.73‰) has a $\delta^{13}C$ of about −14.66‰ to −14.85‰. Lactate biosynthesized from renewable carbon sources are expected to have $\delta^{13}C$ values that are less negative than lactate derived from petroleum. However, the $\delta^{13}C$ distribution of methane from natural gas is differentiated from most carbon sources, with a more negative $\delta^{13}C$ distribution than crude petroleum. Methanotrophic bacteria display a preference for utilizing $^{12}C$ and reducing their intake of $^{13}C$ under conditions of excess methane, resulting in further negative shifting of the $\delta^{13}C$ value. Lactate produced by methanotrophic bacteria as described herein has a $\delta^{13}C$ distribution more negative than lactate from crude petroleum or renewable carbon sources, ranging from about −30‰ to about −70‰.

In certain embodiments, a lactate composition (i.e., composition comprising a lactate) and the lactate contained therein have a $\delta^{13}C$ distribution of less than about −30‰, −40‰, or −50‰. In certain embodiments, the lactate composition and lactate contained therein have a $\delta^{13}C$ distribution from about −30‰ to about −40‰, or from about −40‰ to about −50‰. In further embodiments, the lactate composition and lactate contained therein have a $\delta^{13}C$ of less than −30‰, less than −31‰, less than −32‰, less than −33‰, less than −34‰, less than −35‰, less than −36‰, less than −37‰, less than −38‰, less than −39‰, less than −40‰, less than −41‰, less than −42‰, less than −43‰, less than −44‰, less than −45‰, less than −46‰, less than −47‰, less than −48‰, less than −49‰, less than −50‰, less than −51‰, less than −52‰, less than −53‰, less than −54‰, less than −55‰, less than −56‰, less than −57‰, less than −58‰, less than −59‰, less than −60‰, less than −61‰, less than −62‰, less than −63‰, less than −64‰, less than −65‰, less than −66‰, less than −67‰, less than −68‰, less than −69‰, or less than −70‰. In specific embodiments, the lactate in such embodiments may be the free acid (i.e., lactic acid, $CH_3CH(OH)COOH$, wherein such free acid has a $\delta^{13}C$ as described hereinabove. In other embodiments, the lactate may be a salt, anhydride, oligomer or ester that contains one or more $CH_3C(OH)C(O)$— groups (as in the case of a salt or ester) or one or more $CH_3C(O—)C(O)$—) groups (as in the case of certain esters, oligomers and anhydrides), in which the carbon atoms of the lactate group have a $\delta^{13}C$ as described herein.

Embodiments of the invention include the following:

1. A non-naturally occurring $C_1$ metabolizing microorganism comprising an exogenous nucleic acid encoding a lactate dehydrogenase (LDH), wherein the $C_1$ metabolizing microorganism is capable of converting a carbon feedstock into lactate.

2. The $C_1$ metabolizing microorganism according to embodiment 1, wherein the nucleic acid molecule encoding LDH is from *Actinomyces viscosus, Acinonyx jubatus, Archilochus colubris, Bacillus anthracis, Bacillus caldolyticus, Bacillus coagulans, Bacillus megaterium, Bacillus stearothermophilus* (Q9p4b6) (also known as *Geobacillus stearothermophilus*), *Bacillus subtilis, Bacillus thuringiensis, Bacteroides pectinophilus, Bifidobacterium longum, Bos taurus, Canis familiaris, Canis lupus, Deinococcus radiodurans, Enterococcus faecalis, Enterococcus faecium, Equus ferus, Felis catus, Kluyveromyces lactis, Kluyveromyces maxxianus, Lactobacillus acidophilus, Lactobacillus bulgaricus, Lactobacillus casei, Lactobacillus coryniformis* sp. *torquens, Lactobacillus delbrueckii* (including subsp. *bulgaricus*), *Lactobacillus fermentum, Lactobacillus helveticus, Lactobacillus johnsonii, Lactobacillus pentosus, Lactobacillus plantarum, Lactobacillus rhamnosus, Lactococcus lactis, Listeria monocytogenes, Plasmodium falciparum, Plasmodium ovale, Thermus thermophilus, Mus musculus, Oryctolagus cuniculus, Pediococcus acidilactici, Taeniopygia guttata, Rattus norvegicus, Rhizopus oryzae, Staphylococcus aureus,* or *Streptococcus bovis.*

3. The $C_1$ metabolizing microorganism according to embodiment 1, wherein the exogenous nucleic acid sequence encoding LDH is codon optimized for expression in the methanotrophic bacterium.

4. The $C_1$ metabolizing microorganism according to embodiment 1, wherein the exogenous nucleic acid molecule encodes an amino acid sequence as set forth in any one of SEQ ID NOs:2, 4, 6, 8, 10, 60, 61, 62, 63, or 12.

5. The $C_1$ metabolizing microorganism according to embodiment 1, wherein the exogenous nucleic acid encoding LDH has a sequence as set forth in any one of SEQ ID NOs:1, 3, 5, 7, 9, or 11.

6. The $C_1$ metabolizing microorganism according to embodiment 1, wherein the exogenous nucleic acid encoding LDH is operatively linked to an expression control sequence.

7. The $C_1$ metabolizing microorganism according to embodiment 6, wherein the expression control sequence is a promoter selected from a pyruvate decarboxylase promoter, methanol dehydrogenase promoter, hexulose 6-phosphate synthase promoter, ribosomal protein S16 promoter, serine hydroxymethyl transferase promoter, serine-glyoxylate aminotransferase promoter, phosphoenolpyruvate carboxylase promoter, T5 promoter, or Trc promoter.

8. The $C_1$ metabolizing microorganism according to embodiment 1, wherein the microorganism has endogenous pyruvate decarboxylase activity that is minimal, undetectable, or knocked out.

9. The $C_1$ metabolizing microorganism according to embodiment 1, wherein the microorganism has one or more endogenous methylglyoxal bypass pathway enzymes that are minimally active or knocked out.

10. The $C_1$ metabolizing microorganism according to embodiment 1, wherein the microorganism has endogenous alcohol dehydrogenase activity that is minimal, undetectable, or knocked out.

11. The $C_1$ metabolizing microorganism according to embodiment 1, wherein the microorganism has reduced or knocked out activity for endogenous pyruvate decarboxylase, alcohol dehydrogenase, methylglyoxal synthase, or any combination thereof.

12. The $C_1$ metabolizing microorganism according to embodiment 1, wherein the microorganism is capable of producing from about 1 mg/L to about 500 g/L of lactate.

13. The $C_1$ metabolizing microorganism according to any one of embodiments 1-12, wherein the $C_1$ metabolizing microorganism is a methanotroph.

14. The $C_1$ metabolizing microorganism according to embodiment 13, wherein the methanotroph is *Methylomonas, Methylobacter, Methylococcus, Methylosinus, Methylocystis, Methylomicrobium, Methanomonas, Methylocella*, or *Methylocapsa*.

15. The $C_1$ metabolizing microorganism according to embodiment 13, wherein the methanotroph is *Methylococcus capsulatus* Bath strain, *Methylomonas methanica* 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylobacterium organophilum* (ATCC 27,886), *Methylomonas* sp AJ-3670 (FERM P-2400), *Methylocella silvestris, Methylocella palustris* (ATCC 700799), *Methylocella tundrae, Methylocystis daltona* strain SB2, *Methylocystis bryophila, Methylocapsa aurea* KYG, *Methylacidiphilum infernorum, Methylacidiphilum fumariolicum, Methyloacida kamchatkensis, Methylibium petroleiphilum*, or *Methylomicrobium alcaliphilum*.

16. The $C_1$ metabolizing microorganism according to any one of embodiments 1-15, wherein the carbon feedstock is methane, methanol, syngas, natural gas or unconventional natural gas.

17. A method of producing lactate, comprising culturing a non-naturally occurring $C_1$ metabolizing microorganism comprising an exogenous nucleic acid molecule encoding LDH in the presence of a carbon feedstock under conditions sufficient to produce lactate.

18. The method according to embodiment 17, wherein the nucleic acid molecule encoding LDH is from *Actinomyces viscosus, Acinonyx jubatus, Archilochus colubris, Bacillus anthracis, Bacillus caldolyticus, Bacillus coagulans, Bacillus megaterium, Bacillus stearothermophilus* (Q9p4b6) (also known as *Geobacillus stearothermophilus*), *Bacillus subtilis, Bacillus thuringiensis, Bacteroides pectinophilus, Bifidobacterium longum, Bos taurus, Canis familiaris, Canis lupus, Deinococcus radiodurans, Enterococcus faecalis, Enterococcus faecium, Equus ferus, Felis catus, Kluyveromyces lactis, Kluyveromyces maxxianus, Lactobacillus acidophilus, Lactobacillus bulgaricus, Lactobacillus casei, Lactobacillus coryniformis* sp. *torquens, Lactobacillus delbrueckii* (including subsp. *bulgaricus*), *Lactobacillus fermentum, Lactobacillus helveticus, Lactobacillus johnsonii, Lactobacillus pentosus, Lactobacillus plantarum, Lactobacillus rhamnosus, Lactococcus lactis, Listeria monocytogenes, Plasmodium falciparum, Plasmodium ovale, Thermus thermophilus, Mus musculus, Oryctolagus cuniculus, Pediococcus acidilactici, Taeniopygia guttata, Rattus norvegicus, Rhizopus oryzae, Staphylococcus aureus*, or *Streptococcus bovis*.

19. The method according to embodiment 17, wherein the exogenous nucleic acid sequence encoding LDH is codon optimized for expression in the methanotrophic bacterium.

20. The method according to embodiment 17, wherein the exogenous nucleic acid molecule encodes an amino acid sequence as set forth in any one of SEQ ID NOs: 2, 4, 6, 8, 10, 60, 61, 62, 63, or 12.

21. The method according to embodiment 17, wherein the exogenous nucleic acid encoding LDH has a sequence as set forth in any one of SEQ ID NOs:1, 3, 5, 7, 9, or 11. 22. The method according to embodiment 17, wherein the exogenous nucleic acid encoding LDH is operatively linked to an expression control sequence.

23. The method according to embodiment 22, wherein the expression control sequence is a promoter selected from a pyruvate decarboxylase promoter, methanol dehydrogenase promoter, hexulose 6-phosphate synthase promoter, ribosomal protein S16 promoter, serine hydroxymethyl transferase promoter, serine-glyoxylate aminotransferase promoter, phosphoenolpyruvate carboxylase promoter, T5 promoter, or Trc promoter.

24. The method according to embodiment 17, wherein the microorganism has endogenous pyruvate decarboxylase activity that is minimal, undetectable, or knocked out.

25. The method according to embodiment 17, wherein the microorganism has one or more endogenous methylglyoxal bypass pathway enzymes that are minimally active or knocked out.

26. The method according to embodiment 17, wherein the microorganism has endogenous alcohol dehydrogenase activity that is minimal, undetectable, or knocked out.

27. The method according to embodiment 17, wherein the microorganism has reduced or knocked out activity for endogenous pyruvate decarboxylase, alcohol dehydrogenase, methylglyoxal synthase, or any combination thereof.

28. The method according to embodiment 17, wherein the microorganism is capable of producing from about 1 mg/L to about 500 g/L of lactate.

29. The method according to any one of embodiments 17-28, wherein the $C_1$ metabolizing microorganism is a methanotroph.

30. The method according to embodiment 29, wherein the methanotroph is *Methylomonas, Methylobacter, Methylococcus, Methylosinus, Methylocystis, Methylomicrobium, Methanomonas, Methylocella*, or *Methylocapsa*.

31. The method according to embodiment 29, wherein the methanotroph is *Methylococcus capsulatus* Bath strain, *Methylomonas methanica* 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylobacterium organophilum* (ATCC 27,886), *Methylomonas* sp AJ-3670 (FERM P-2400), *Methylocella silvestris, Methylocella palustris* (ATCC 700799), *Methylocella tundrae, Methylocystis dal-* tona strain SB2, *Methylocystis bryophila*, *Methylocapsa aurea* KYG, *Methylacidiphilum infernorum*, *Methylacidiphilum fumariolicum*, *Methyloacida kamchatkensis*, *Methylibium petroleiphilum*, or *Methylomicrobium alcaliphilum*.

32. The method according to any one of embodiments 17-31, wherein the carbon feedstock is methane, methanol, syngas, natural gas or unconventional natural gas.

33. A lactate composition, wherein the $\delta^{13}C$ of the lactate is less than about −30‰.

34. A lactate composition according to embodiment 33, wherein the $\delta^{13}C$ of the lactate ranges from about −70‰ to about −30‰.

35. A lactate composition according to embodiment 33, wherein the $\delta^{13}C$ of the lactate ranges from about −60‰ to about −40‰.

36. The lactate composition according to any one of embodiments 33-35, wherein the lactate composition is produced by a non-naturally occurring $C_1$ metabolizing microorganism comprising a exogenous nucleic acid encoding a lactate dehydrogenase (LDH).

37. The lactate composition according to embodiment 36, wherein the $C_1$ metabolizing microorganism is a methanotroph.

38. The lactate composition according to embodiment 37, wherein the methanotroph is *Methylomonas*, *Methylobacter*, *Methylococcus*, *Methylosinus*, *Methylocystis*, *Methylomicrobium*, *Methanomonas*, *Methylocella*, or *Methylocapsa*.

39. The lactate composition according to embodiment 37, wherein the methanotroph is *Methylococcus capsulatus* Bath strain, *Methylomonas methanica* 16a (ATCC PTA 2402), *Methylosinus trichosporium* OB3b (NRRL B-11,196), *Methylosinus sporium* (NRRL B-11,197), *Methylocystis parvus* (NRRL B-11,198), *Methylomonas methanica* (NRRL B-11,199), *Methylomonas albus* (NRRL B-11,200), *Methylobacter capsulatus* (NRRL B-11,201), *Methylobacterium organophilum* (ATCC 27,886), *Methylomonas* sp AJ-3670 (FERM P-2400), *Methylocella silvestris*, *Methylocella palustris* (ATCC 700799), *Methylocella tundrae*, *Methylocystis daltona* strain SB2, *Methylocystis bryophila*, *Methylocapsa aurea* KYG, *Methylacidiphilum infernorum*, *Methylacidiphilum fumariolicum*, *Methyloacida kamchatkensis*, *Methylibium petroleiphilum*, or *Methylomicrobium alcaliphilum*.

The foregoing and other aspects of the invention may be better understood in connection with the following non-limiting examples.

EXAMPLES

Example 1

$C_1$ Metabolizing Microorganisms Engineered for Lactate Production

I. *Methylococcus capsulatus* Bath Engineered for Lactate Production.

Figure 3:
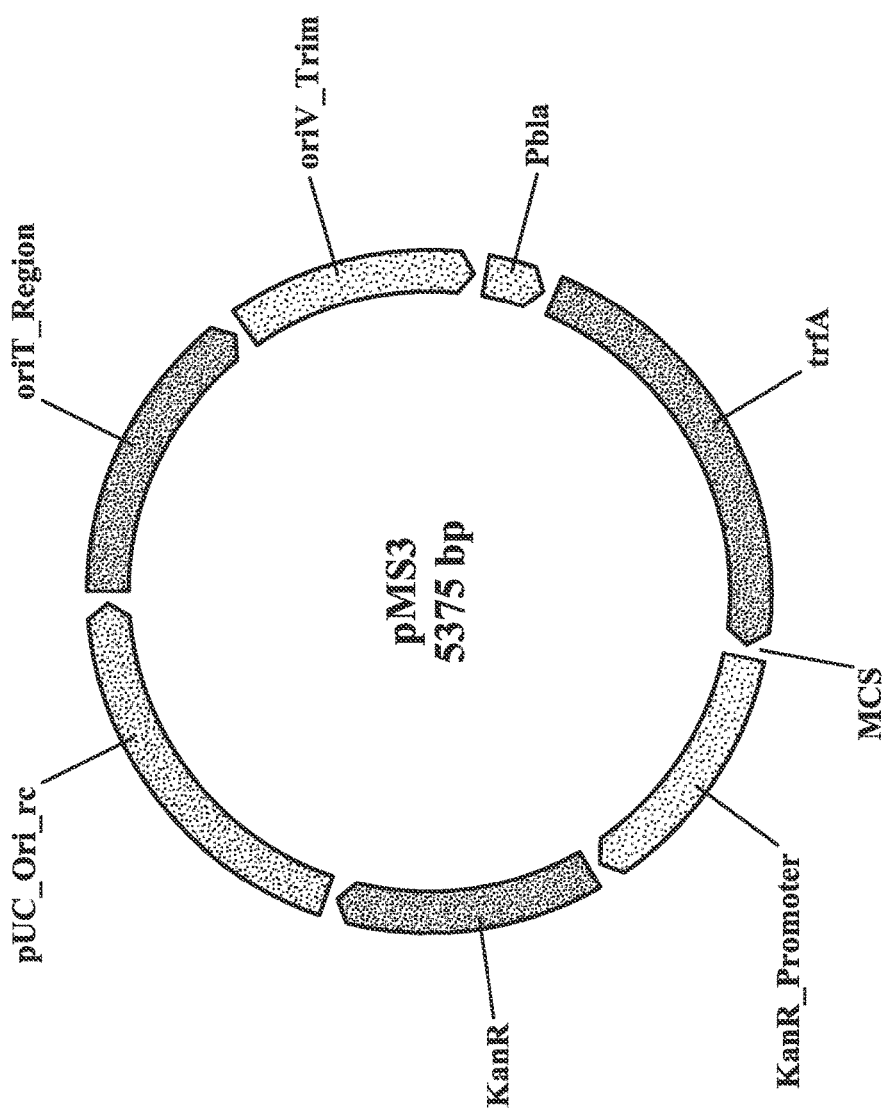
FIG. 3 depicts vector pMS3 of the present invention comprising sequences encoding a replication initiation protein (trfA) and promoter (Pbla), an origin of replication (oriV), an origin of transfer (oriT), multiple cloning sites (MCS), kanamycin resistance gene (KanR) and promoter (KanR_promoter) and origin of replication for *E. coli* (pUC_Ori_rc).

Host cells (*Methylococcus capsulatus* Bath) were engineered to possess an exogenous L-lactate dehydrogenase (ldh) nucleic acid to allow the production of L-lactate from a $C_1$ substrate (methane). Nucleic acid sequences encoding lactate dehydrogenases were codon optimized for *Methylococcus capsulatus* Bath and synthesized. These codon optimized nucleic acids corresponded in sequence to the following SEQ ID NOs: 1, 3, 5, 7, 9, 11, 13, 15, 17, 19, 21, 23, 25, 27, 29, 31, 33, 35, 37, 39, 41, 43, and 45. They encode the following LDHs, respectively, SEQ ID NOs:2 (*Streptococcus pasteurianus*), 4 (*Lactobacillus helveticus*), 6 (*Bos taurus*), 8 (*Pediococcus acidilactici*), 10 (*Rhizopus oryzae*), 12 (*Enterococcus faecalis*), 14 (*Lactobacillus casei*), 16 (*Bacillus megaterium*), 18 (*Taeniopygia guttata*), 20 (*Lactobacillus plantarum*), 22 (*Lactobaillus acidophilus*), 24 (*Staphylococcus aureus*), 26 (*Bacillus caldolyticus*), 28 (*Actinomyces viscosus*), 30 (*Bacillus anthracis*), 32 (*Ruminococcus torques*), 34 (*Listeria marthii*), 36 (*Bacillus subtilis*), 38 (*Enterococcus faecium*), 40 (*Bacillus thuringiensis*), 42 (*Geobacillus stearothermophilus*), 44 (*Deinococcus radiodurans*), 46 (*Plasmodium ovale* (variant)), and 48 (*Thermus thermophilus*). The LDH nucleic acids were cloned into plasmid pMS3 (depicted in FIG. 3) downstream of a promoter system that was either the methanol dehydrogenase (MDH) promoter with ribosome binding site (SEQ ID NO:49, putative promoter from methanol dehydrogenase protein from *M. capsulatus* Bath, large subunit n229 (MCA0779)) (vector pMS3×1) or alternatively in the same vector with one of two different mutated ribosomal binding sites (vectors pMS3×2 and pMS3×3) or downstream of the MDH promoter in an IPTG-inducible (LacIq) promoter system (with native ribosomal binding site (vector pMS3z1) or alternatively in the same vector with one of the two different mutated ribosomal binding sites mutated ribosomal binding sites (vectors pMS3z2 and pMS3z3). pMS3, derived from the RK2 plasmid (see Schmidhauser, et al., J. Bacteriol. 164(1):446-55 (1985), which is incorporated herein by reference) is a minimal plasmid containing sequences that encode a replication initiation protein (trfA) and promoter (Pbla), an origin of replication (oriV), an origin of transfer (oriT), and kanamycine resistance gene and promoter (KanR promoter). The vectors were introduced into *Methylococcus capsulatus* Bath via conjugative mating based on the methods reported by Ali and Murrell (Microbiology 155:761, 2009).

The vectors were first transformed into *E. coli* S17-1 using standard electroporation methods. Transformation was confirmed by selection of kanamycin-resistant colonies on LB-agar containing 30 µg/mL kanamycin. Sequence of donor plasmid was verified via sequencing. Transformed colonies were inoculated into LB media containing 30 µg/mL kanamycin and shaken overnight at 37° C. Aliquots (e.g., 100 µl) of overnight cultures were used to inoculate fresh LB media containing 30 µg/mL kanamycin and then grown to an optical density ($OD_{600}$) between 0.45-0.6 (mid-log phase growth). Aliquots of this second culture equivalent to an OD of 1.6 (e.g., 3 mL of a culture with an $OD_{600}$ of 0.5) were then pelleted via centrifugation and washed three times with sterile MM-W1 via centrifugation and resuspension. A 10 mL aliquot of the overnight culture was then collected on a sterile 47 mm nitrocellulose filter (0.2 mm pore size). The *E. coli* donor cells were washed on the filter with 50 mL sterile NSM media to remove residual media and antibiotic.

In parallel, a sample of the *M. capsulatus* Bath (NCIMB 11132) recipient strain was inoculated into 100 mL serum bottles containing 20-50 mL MM-W1 media. The bottles were sealed with butyl rubber septa and crimped and between 40-60 mL of methane was then introduced into the sealed bottle. The bottles were shaken continuously in a 42° C. incubator until reaching an $OD_{600}$ of approximately 0.3. Approximately 5 mL of *M. capsulatus* Bath culture was then pelleted via centrifugation and mixed with the *E. coli* donor cells. This mixture was placed on an MM-W1 agar plate containing 0.5% yeast extract and incubated for 48 h at 37° C. in the presence of a 1:1 mixture of methane and air. After 24 h, cells were re-suspended in 0.5 mL sterile (MM-W1)

medium and aliquots (100 µL) were spread onto MM-W1 agar plates containing 7.5 µg/mL kanamycin.

The plates were incubated in sealed chambers containing a 1:1 mixture of methane and air and maintained at 42° C. (*M. capsulatus* Bath). The gas mixture was replenished approximately every 2 days until colonies formed, typically after 5-8 days. Colonies were streaked onto NSM plates containing kanamycin to confirm kanamycin resistance as well as to further isolate transformed methanotroph cells from residual *E. coli* donor cells.

The presence of ldh expression or LDH function was verified by (1) PCR and sequencing and/or (2) assaying for the presence of lactate. For example, to verify transfer colony material was boiled at 98° C. and subjected to PCR using standard conditions (98° C. for 1 min; 30 cycles of 98° C. for 10 s, 55° C. for 30 s, and 72° C. for 1 min; 72° C. for 10 min). Optionally, as a further control, 1 µl each of the isolated plasmids can be transformed back into *E. coli* XL1-Blue MRF' Kan (Stratagene, La Jolla, Calif.), and the plasmids can be isolated to verify by restriction endonuclease digests.

The recombinant *M. capsulatus* Bath were cultured at 42° C. in 24-well plates containing MM-W1 medium contained in sealed chambers. The headspace composition was adjusted to a 1:1 volume of methane:air. The bottles were shaken at a rate of 200-250 rpm. Alternatively, the culture was maintained on MM-W1-media plates solidified with 1.5% w/v agar grown in a gas-tight chamber containing a 1:1 (v/v) methane:air gas mixture. Plates were incubated inverted in the chamber at 42° C.

Production of Lactate from a $C_1$ Substrate ($CH_4$)

*M. capsulatus* Bath transformed with a vector alone (i.e., negative control without the exogenous LDH encoding nucleic acid and promoter) or vector containing the exogenous LDH nucleic acid and promoter system were used to inoculate 2.5 mL MM-W1 media/well of 24 well plates having 7.5 µg/mL kanamycin. The composition of medium MM-W1 used was as follows: 0.8 mM $MgSO_4*7H_2O$, 10 mM $NaNO_3$, 0.14 mM $CaCl_2$, 1.2 mM $NaHCO_3$, 2.35 mM $KH_2PO_4$, 3.4 mM $K_2HPO_4$, 20.7 µM $Na_2MoO_4*2H_2O$, 1 µM $CuSO_4*5H_2O$, 10 µM $Fe^{III}$—Na-EDTA, and 1 mL per liter of trace metals solution (containing, per liter 500 mg $FeSO_4*7H_2O$, 400 mg $ZnSO_4*7H_2O$, 20 mg $MnCl_2*7H_2O$, 50 mg $CoCl_2*6H_2O$, 10 mg $NiCl_2*6H_2O$, 15 mg $H_3BO_3$, 250 mg EDTA). Phosphate, bicarbonate, and $Fe^{III}$—Na-EDTA were added after the media was autoclaved and cooled. The plates were placed in sealed chambers and the headspace was flushed with a 1:1 mixture of air and methane as the carbon source for *M. capsulatus* Bath, the plates were sealed and then shaken continuously at a rate of 200-250 rpm during incubation at 42-45° C. for a 24 hour pre-culture. Then, new 24 well plates containing 2.5 mL fresh MM-W1 and kanamycin were inoculated with 0.25 mL of the pre-culture and incubated at 42-45° C. for 72 hours. *M. capsulatus* Bath strain containing the MDH promoter in the IPTG-inducible (LacIq) promoter system was grown in the presence of 0.1-10 mM IPTG). Cells were harvested by centrifugation and the supernatants were analyzed using the EnzyFluo™ L-Lactate Assay Kit as per the manufacturer's instructions (BioAssay Systems, Hayward, Calif. 94545, Catalog No. EFLLC-100) with the exception that the supernatants were incubated with the kit reagents for two hours prior to measuring fluorescence. Since methane was the only carbon source provided to the cells, all lactate produced must have been derived from methane.

Results

The results in Table 1 demonstrate the production of lactate using a variety of exogenous nucleic acids encoding lactate dehydrogenase. In certain cases where lactate was produced under constitutive expression of the LDH, the recombinant *M. capsulatus* Bath showed a high lactate to $OD_{600}$ ratio (see FIG. 1).

TABLE 1

Lactic Acid Production by *M. capsulatus* Bath Expressing LDH

| LDH nucleic acid in vector SEQ ID NO: | LDH polypeptide sequence source | Constitutive | | | Inducible | |
|---|---|---|---|---|---|---|
| | | (pMS3x1) | (pMS3x2) | (pMS3x3) | (pMS3z1) | (pMS3z3) |
| 27 | *Actinomyces viscosus* | | ++ | +++ | ++ | + |
| 29 | *B. anthracis* | | +++ | | +++ | +++ |
| 25 | *Bacillus caldolyticus* | | + | +++ | +++ | + |
| 15 | *Bacillus megaterium* | | | + | +++ | +++ |
| 35 | *Bacillus subtilis* | | | + | | ++ |
| 39 | *Bacillus thuringiensis* | | + | | | |
| 43 | *D. radiodurans* | | | | +++ | ++ |
| 11 | *Enterococcus faecalis* | | + | +++ | ++ | +++ |
| 37 | *Enterococcus faecium* | | + | + | + | |
| 41 | *Geobacillus stearothermophilus* | | + | + | ++ | ++ |
| 21 | *Lactobacillus acidophilus* | | ++ | ++ | ++ | ++ |
| 13 | *Lactobacillus casei* | + | | | + | |
| 19 | *Lactobacillus plantarum* | | ++ | + | ++ | |
| 33 | *Listeria marthii* | | | ++ | +++ | +++ |
| 7 | *Pediococcus acidilactici* | + | | | +++ | +++ |
| 9 | *R. oryaze* | | | | +++ | +++ |

TABLE 1-continued

Lactic Acid Production by M. capsulatus Bath Expressing LDH

| LDH nucleic acid in vector SEQ ID NO: | LDH polypeptide sequence source | Constitutive | | | Inducible | |
|---|---|---|---|---|---|---|
| | | (pMS3x1) | (pMS3x2) | (pMS3x3) | (pMS3z1) | (pMS3z3) |
| 31 | Ruminococcus torques | | | | ++ | +++ |
| 23 | Staphylococcus aureus | | ++ | | +++ | ++ |
| 1 | Streptococcus pasteurianus | | + | | ++ | +++ |
| 17 | Taeniopygia guttata | | + | | | |
| 47 | Thermus Thermophilus | | + | + | + | |

For each sequence in Table 1, the highest detected value is listed according to the following scale: +3-100 uM, ++100-1000 uM, +++>1000 uM. The lower limit for designating recombinant cells as having positive LDH activity (3 uM) was set at 3-fold higher concentrations of lactate than the assay background from strains not known to be carrying a functional LDH nucleic acid (i.e., the negative control strains). In several cases, LDH activity (i.e., lactate production) was not detected above this threshold for the nucleic acids listed in the above table with certain promoters, or nucleic acids encoding LDHs from Bos Taurus (SEQ ID NO:5), L. helveticus (SEQ ID NO:3), or Plasmodium ovale (SEQ ID NO:45). In three cases where the exogenous LDH nucleic acid under control of a constitutive promoter was conjugated into the host strain (i.e., the nucleic acids encoding Bacillus anthracis LDH (n:29), Bacillus thuringensis LDH (SEQ ID NO:39), and Deinococcus radiodurans LDH (SEQ ID NO:43)), no colonies were observed, however colonies did form when the same exogenous LDH nucleic acids were placed under control of an inducible promoter indicating a potential toxic effect of lactate on the cells. While not wishing to be bound by any theory, it is believed that due to the high toxicity of lactate, LDH activity induces a high selective pressure on expressing cells to mutate or otherwise inactivate the LDH nucleic acid. Thus, the lack of activity above threshold can be caused by a number of factors (which were observed in several clones identified as being below the detection threshold) including mutations in the LDH nucleic acid or loss of the plasmid, and does not provide conclusive evidence for the presence or absence of LDH function in that case.

II. Methylosinus trichsporium OB3b and Methylomicrobium buryatense 5G Engineered for Lactate Production.

Host cells (Methylosinus trichsporium OB3b and Methylomicrobium buryatense 5G) were engineered to possess an exogenous lactate dehydrogenase (ldh) nucleic acid to allow the production of L-lactate from a $C_1$ substrate (methane). The exogenous LDH encoding nucleic acid molecules from Part I above were individually cloned into expression vector pMS10 (a PMS3 equivalent plasmid with kanamycin resistance gene from a different source) downstream of a promoter system for conjugation into M. trichosporium OB3b or M. buryatense 5G based on the methods reported by Ali and Murrell (Microbiology 155:761, 2009). For transformation of Methylosinus trichsporium OB3b, the promoter was the Ob3b promoter sga (serine-glycoxilate transaminase) (SEQ ID NO:50). For transformation of Mthylomicrobium buryatense 5G, the promoter was either Methylomonas 16a moxF (methanol dehydrogenase) promoter (SEQ ID NO:51) or Methylomonas 16a hps (hexulose-6-phosphate synthetase) promoter (SEQ ID NO:52).

Briefly, the mobilizable plasmid containing one or more nucleic acids of interest (e.g., ldh) and encoding kanamycin resistance was first transformed into E. coli S17-1 using standard electroporation methods. Transformation was confirmed by selection of kanamycin-resistant colonies on LB-agar containing 30 μg/mL kanamycin. Transformed colonies were inoculated into LB media containing 30 μg/mL kanamycin and shaken at 37° C. until the OD600 reached 1.0. A 1.0 mL aliquot of the culture was then collected in a sterile Eppendorf tube (1.6 ml size). The E. coli donor cells were washed 2×1.0 mL sterile MM-W1 (OB3b) or NMS (5G) media to remove residual media and antibiotic.

In parallel, a sample of the M. trichosporium OB3b (NCIMB 11131) or M. buryatense 5G (from Dr. Mary Lidstrom, University of Washington) recipient strain was inoculated into 100 mL serum bottles containing 20-50 mL MM-W1 (OB3b) or NMS (5G) media. The headspace of the bottles was then flushed with a 1:1 mixture of oxygen and methane, and the bottles were sealed with butyl rubber septa and crimped. The bottles were shaken continuously in a 30° C. incubator until reaching an $OD_{600}$ of approximately 0.5. The OB3b or 5G cells were then collected by centrifugation and washed with 50 mL of sterile MM-W1 or NMS media. The washed cells were resuspended in sterile MM-W1 or NMS media to an $OD_{600}$ of 1.0 and aliquots mixed with the donor E. coli at a recipient:donor ratio of 2:1. The cell mixture was pelleted by centrifugation and the cell pellet spotted on an MM-W1 or NMS agar plate containing 0.5% yeast extract and incubated for 48 h at 30° C. in the presence of a 1:1 mixture of methane and air. After 48 h, cells were re-suspended in 1.0 mL sterile medium and aliquots (100 μL) were spread onto MM-W1 or NMS agar plates containing 4-7.5 μg/mL kanamycin.

The plates were incubated in sealed chambers containing a 1:1 mixture of methane and air and maintained at 30° C. The gas mixture was replenished every 2 days until colonies formed, typically after 7-14 days. Colonies were streaked onto MM-W1 or NMS plates containing kanamycin to confirm kanamycin resistance as well as to further isolate transformed methanotroph cells from residual E. coli donor cells.

The presence of ldh expression or LDH function was verified by one or more of (1) PCR and sequencing, (2) Western blot analysis, and (3) assaying for the presence of lactate. For example, to verify transfer, plasmid DNA was isolated and subjected to PCR using OneTaq 2× Master Mix with Standard buffer (New England BioLabs) using standard conditions (95° C. for 5 min; 25 cycles of 95° C. for 30 s, 60° C. for 30 s, and 72° C. for 1 min; 72° C. for 10 min) and primer sets specifically designed to bind outside of and interior to the ldh nucleic acid. The original plasmid DNA containing the cloned ldh nucleic acid(s) was used as a positive control for the PCR.

The recombinant *M. trichosporium* OB3b or *M. buryatense* 5G were cultured at 30° C. in serum bottles containing MM-W1 or NMS containing 4-7.5 ug/ml kanamycin medium. The headspace composition was adjusted to a 1:1 volume of methane:air. The bottles were shaken at a rate of 200-250 rpm. Alternatively, the culture was maintained on MM-W1 or NMS media plates solidified with 1.5% w/v agar grown in a gas-tight chamber containing a 1:1 (v/v) methane:air gas mixture. Plates were incubated inverted in the chamber at 30° C.

Production of Lactate from a $C_1$ Substrate ($CH_4$)

*M. trichosporium* OB3b or *M. buryatense* 5G transformed with a vector alone or vector containing an ldh nucleic acid were used to inoculate 2.0 mL MM-W1 or NMS media in Balch tubes (Bellco Glass) having 5 μg/mL kanamycin. The composition of medium MM-W1 used was as follows: 0.8 mM $MgSO_4*7H_2O$, 10 mM $NaNO_3$, 0.14 mM $CaCl_2$, 1.2 mM $NaHCO_3$, 2.35 mM $KH_2PO_4$, 3.4 mM $K_2HPO_4$, 20.7 μM $Na_2MoO_4*2H_2O$, 1 μM $CuSO_4*5H_2O$, 10 μM $Fe^{III}$—Na-EDTA, and 1 mL per liter of trace metals solution (containing, per liter 500 mg $FeSO_4*7H_2O$, 400 mg $ZnSO_4*7H_2O$, 20 mg $MnCl_2*7H_2O$, 50 mg $CoCl_2*6H_2O$, 10 mg $NiCl_2*6H_2O$, 15 mg $H_3BO_3$, 250 mg EDTA). Phosphate, bicarbonate, and $Fe^{III}$—Na-EDTA were added after the media was autoclaved and cooled. The composition of the NMS media used was as follows: 1.00 g/L $MgSO_4*7H_2O$, 0.02 g/L $CaCl_2*6H_2O$, 1.00 g/L $KNO_3$, 15 g/L NaCl, 20 ml Phosphate buffer (5.44 g/L $KH_2PO_4$, 14.34 g/L $Na_2HPO_4*12\ H_2O$), 50 ml Carbonate buffer (45 ml of 1M $NaHCO_3$+5 ml 1M $Na_2CO_3$), 2 ml Trace Element solution (0.5 g/L $Na_2$-EDTA, 1.0 g/L $FeSO_4*7H_2O$, 0.75 g/L Fe-EDTA, 0.8 g/L $ZnSO_4*7H2O$, 0.005 g/L $MnCl_2*4H_2O$, 0.03 g/L $H_3BO_3$, 0.05 g/L $CoCl_2*6H_2O$, 0.4 g/L Cu-EDTA, 0.6 g/L $CuCl_2*2H_2O$, 0.002 g/L $NiCl_2*6H_2O$, 0.05 g/L $Na_2MoO_2*2H2O$) (Ojala, D. S., et al., *Methods in Enzymology*, Vol. 495, pp. 99-118). Sterile phosphate and carbonate buffers were added after the solution cooled to room temperature. The plate headspace was flushed with a 1:1 mixture of oxygen and methane as the carbon source for the strains, the tubes were sealed with butyl rubber septa, crimped, and then shaken continuously at a rate of 200-250 rpm during incubation at 30° C. for a 72 hours. Cells were harvested by centrifugation and the supernatants were analyzed using the EnzyFluo™ L-Lactate Assay Kit as per the manufacturer's instructions (BioAssay Systems, Hayward, Calif. 94545, Catalog No. EFLLC-100) with the exception that the supernatants were incubated with the kit reagents for two hours prior to measuring fluorescence. Results were normalized to $OD_{600}$ values for each corresponding culture. Since methane was the only carbon source provided to the cells, all lactate produced must have been derived from methane.

Results

*M. trichosporium* OB3b and *M. buryatesne* 5G were altered to produce L-lactate by introducing and expressing an exogenous L-lactate dehydrogenase nucleic acid. The various exogenous lactate dehydrogenase nucleic acids were operatively linked to a constitutive promoter in an expression vector that functions in methanotrophs.

In all cases where lactate was produced, the $OD_{600}$ of the cultures ranged from 0.31 to 0.71 and all recombinant strains produced low, but detectable levels (1-20 μM greater than 3-fold higher concentrations of lactate than strains not known to be carrying a functional LDH nucleic acid) of lactate.

Example 2

Stable Carbon Isotope Distribution in Products Derived from $C_1$ Metabolizing Microorganisms Methane-derived lactic acid produced by engineered strains of *M. capsultus* Bath was analyzed for carbon content (% dry weight) and carbon ($^{13}C$) stable isotope ratio via elemental analyzer/continuous flow isotope ratio mass spectrometry using a CHNOS Elemental Analyzer (vario ISOTOPE cube, Elementar, Hanau, Germany) coupled with an IsoPrime100 IRMS (Isoprime, Cheadle, UK). Samples of methanotrophic biomass cultured in fermenters or serum bottles were centrifuged, resuspended in deionized water and volumes corresponding to 0.2-2 mg carbon (about 0.5-5 mg dry cell weight) were transferred to 5×9 mm tin capsules (Costech Analytical Technologies, Inc., Valencia, Calif.) and dried at 80° C. for at least 24 hours. Samples of lactic acid (approx. 0.3-1 mg) recovered from engineered *M. capsulatus* Bath cultures expressing LDH-encoding nucleic acid sequences encoding different LDHs were similarly resuspended in deionized water, transferred to 5×9 mm tin capsules and dried at 80° C. for at least 24 hours. Standards containing at least 0.1 mg carbon provided reliable $\delta^{13}C$ values.

The isotope ratio is expressed in "delta" notation (‰), wherein the isotopic composition of a material relative to that of a standard on a per million deviation basis is given by $\delta^{13}C$ (or $\delta^{15}N$)=$(R_{sample}/R_{Standard-1})\times 1,000$, wherein R is the molecular ratio of heavy to light isotope forms. The standard for carbon is the Vienna Pee Dee Belemnite (V-PDB) and for nitrogen is air. The NIST (National Institute of Standards and Technology) proposed SRM (Standard Reference Material) No. 1547, peach leaves, was used as a calibration standard. All isotope analyses were conducted at the Center for Stable Isotope Biogeochemistry at the University of California, Berkeley. Long-term external precision for C and N isotope analyses is 0.10‰ and 0.15‰, respectively.

Separate *M. capsulatus* Bath strains constructed for constitutive expression of 4 different LDH nucleic acids (see Table 2) were grown on methane in 0.5 L serum bottles containing 130 mL of defined media MMS1.0 amended with 15 ug/mL kanamycin. The strains were inoculated from serum bottle batch cultures (7% v/v) grown in the same media supplied with a 1:1 (v/v) mixture of methane and air. The composition of medium MMS1.0 was as follows: 0.8 mM $MgSO_4*7H_2O$, 30 mM $NaNO_3$, 0.14 mM $CaCl_2$, 1.2 mM $NaHCO_3$, 2.35 mM $KH_2PO_4$, 3.4 mM $K_2HPO_4$, 20.7 μM $Na_2MoO_4*2H_2O$, 6 μM $CuSO_4*5H_2O$, 10 μM $Fe^{III}$—Na-EDTA, and 1 mL per liter of a trace metals solution (containing, per L: 500 mg $FeSO4*7H_2O$, 400 mg $ZnSO_4*7H_2O$, 20 mg $MnCl_2*7H2O$, 50 mg $CoCl_2*6H_2O$, 10 mg $NiCl_2*6H_2O$, 15 mg $H_3BO_3$, 250 mg EDTA). Phosphate, bicarbonate, and $Fe^{III}$—Na-EDTA were added after media was autoclaved and cooled. The final pH of the media was 7.0±0.1. The serum bottles were inoculated in duplicate, sealed with rubber sleeve stoppers and injected with 60 mL methane gas (99% purity; grade 2.0, Praxair supplied by Alliance Gas, San Carlos, Calif.) added via syringe through sterile 0.45 μm filter and sterile 27G needles. The cultures were incubated at 42° C. with rotary shaking at 250 rpm and growth was measured at approximately 12 to 24 hour intervals by withdrawing 1 mL samples to determine $OD_{600}$. Sub-samples (0.5 mL) were clarified by centrifugation and the cell-free supernatants analyzed for L-lactate as described above. After sampling, the bottles were vented and headspace replaced with 60 mL of the methane and 60 to 120 mL of concentrated oxygen (at least 85% purity). At about 72 hours final samples were removed and the remaining culture volumes were clarified by centrifugation (8,000 rpm, 10 minutes), their pH determined (pH 6.7 to 6.9) and the supernatants stored at −20° C. until work up for product recovery and analysis.

TABLE 2

Strain sample description

| Strain ID | SEQ ID NO. (Vector) | LDH Source |
|---|---|---|
| 1 | 27 (pMS3x3) | A. viscosus |
| 3 | 33 (pMS3x3) | L. marthii |
| 4 | 21 (pMS3x3) | L. acidophilus |
| 5 | 29 (pMS3x2) | B. anthracis |

The lactic acid was recovered from each of these cultures by liquid-liquid extraction and the material extracted from acidified supernatants was subsequently analyzed for L-lactic acid content, relative lactic acid composition and for stable carbon isotope distribution ($\delta^{13}C$ values; see Table 3). Supernatants from methane-grown cultures of engineered M. capsulatus Bath strains expressing LDH-encoding nucleic acid sequences encoding different LDHs were clarified by centrifugation, adjusted to pH 2 using concentrated HCl and extracted twice using equal volumes of ethyl acetate (Fisher, HPLC-grade). The ethyl acetate fractions from each sample were combined, dried over anhydrous sodium sulfate and then concentrated to dryness under reduced pressure by rotary evaporation at 40° C. The residues were dissolved in ethyl acetate and subsamples analyzed for L-lactic acid content (EnzyFluo™ L-Lactate Assay Kit, Catalog No. EFLLC-100; BioAssay Systems, Hayward, Calif. 94545) and lactic acid composition by GC-MS.

Gas chromatography-mass spectrometry was carried out on an Agilent 6890 GC equipped with a Zebron ZB-5HT (p/n 7HG-G015-11; Phenomenex, Torrance Calif.) and a mass selective detector. The initial column temperature was 50° C. and was increased at a rate of 20° C. per min to 320° C. and held for 5 min. Temperatures of the inlet and transfer line were 250 C and helium was used as a carrier gas. Samples containing L-lactate recovered by liquid-liquid extraction were dervatized with BSTFA prior to analysis (1.0 uL injections) as follows: To dry lactate-containing extracts (containing 0.3 to 1 mg L-lactate) in borosilicate GC-vials were added 400 uL N,O-bis(trimethylsilyl)trifluoroacetamide (BSTFA), 400 uL acetonitrile and 100 uL toluene. A blank sample was prepared in a similar method as reference. Sample vials with derivatization solvents were heated for 1 hr using a heatblock at 50° C. Final derivatized samples were analyzed by GC-MS using the conditions outlined above. Chromatograms were integrated and individual peaks were logged for time and area counts. Sample chromatograms were overlayed with the blank chromatogram to determine the peaks common to both blank and samples so that they could be eliminated from the later relative quantitation assessment. The mass spectra of each remaining peak in the chromatogram was reviewed against a mass spectral database for tentative identification. The final list of analytes and peak areas was then used to determine relative concentrations for lactic acid relative to all analytes. For this step, it was assumed that all analytes had equivalent total abundance counts (essentially equivalent response factor). The results indicated that the relative content of the lactic acid was 55-80% depending on the individual sample (see Table 3).

TABLE 3

Stable Carbon Isotope Distribution for L-Lactic Acid produced by Different Lactate Dehydrogenases in Methylococcus capsulatus

| Strain ID No. | LDH (or Lactate) Source | LA Purity (%) | Carbon mass analyzed (mg)† | $\delta^{13}C$ L-Lactic Acid |
|---|---|---|---|---|
| 1 | A. viscosus | 70.1 | 0.24 | −46.82 |
| 3 | L. marthii | 73.6 | 0.25 | −42.74 |
| 3 | L. marthii | 80.6 | 0.35 | −54.55 |
| 4 | L. acidophilus | 55.8 | 0.27 | −50.61 |
| 4 | L. acidophilus | 55.4 | 0.27 | −50.62 |
| 5 | B. anthracis | 71.3 | 0.29 | −45.44 |
| 5 | B. anthracis | 73.7 | 0.38 | −48.93 |
| Controls: | | | | |
| Sodium L-Lactate | Aldrich 71718 | >98 | 0.98 | −10.60 |
| Sodium Lactate | Aldrich 71718 | >98 | 0.87 | −10.59 |
| Calcium L-Lactate pentahydrate | Aldrich C8356 | >98 | 0.96 | −12.16 |
| Calcium L-Lactate pentahydrate | Aldrich C8356 | >98 | 0.90 | −12.09 |

*Purity of lactic acid was determined by GC-MS as described in Text.
†The mass of carbon analyzed is reported from results of the CHNOS Elemental Analyzer.

While specific embodiments of the invention have been illustrated and described, it will be readily appreciated that the various embodiments described above can be combined to provide further embodiments, and that various changes can be made therein without departing from the spirit and scope of the invention.

All of the U.S. patents, U.S. patent application publications, U.S. patent applications, foreign patents, foreign patent applications and non-patent publications referred to in this specification, including but not limited to U.S. Application No. 61/836,609 and U.S. Application No. 61/928,390, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A methanotrophic bacteria comprising a heterologous nucleic acid encoding a lactate dehydrogenase (LDH), wherein methanotrophic bacteria is capable of converting methane into lactate.

2. The methanotrophic bacteria of claim 1, wherein the methanotrophic bacteria is selected from the group consisting of a Type I methanotroph, a Type II methanotroph, and a Type X methanotroph.

3. The methanotrophic bacteria of claim 1, wherein the methanotrophic bacteria is an obligate methanotroph.

4. The methanotrophic bacteria according to claim 1, wherein the methanotrophic bacteria is selected from the group consisting of a *Methylococcus*, a *Methylomonas*, a *Methylobacter*, a *Methylosinus*, a *Methylocystis*, a *Methylomicrobium*, a *Methanomonas*, a *Methylocella*, a *Methylacidiphilum*, *Methyloacida*, a *Methylibium*, and a *Methylocapsa*.

5. The methanotrophic bacteria of claim 1, wherein the methanotrophic bacteria is selected from the group consisting of *Methylococcus capsulatus* Bath, *Methylomonas methanica* 16a, *Methylosinus trichosporium* OB3b, *Methylomicrobium buryatense* 5G, *Methylosinus sporium*, *Methylocystis parvus*, *Methylomonas methanica*, *Methylomonas albus*, *Methylobacter capsulatus*, *Methylobacterium organophilum*, *Methylomonas* sp AJ-3670, *Methylocella silvestris*, *Methylocella palustris*, *Methylocella tundrae*, *Methylocystis daltona* SB2, *Methylocystis bryophila*, *Methylocapsa aurea* KYG, *Methylacidiphilum infernorum*, *Methylacidiphilum fumariolicum*, *Methyloacida kamchatkensis*, *Methylibium petroleiphilum*, and *Methylomicrobium alcaliphilum*.

6. The methanotrophic bacteria of claim 1, wherein the methanotrophic bacteria is selected from the group consisting of *Methylococcus capsulatus* Bath strain, *Methylosinus trichosporium* OB3b, and *Methylomicrobium buryatense* 5G.

7. The methanotrophic bacteria according to claim 1, wherein the heterologous nucleic acid encodes a lactate dehydrogenase comprising an amino acid sequence that is at least 85% identical to a reference amino acid sequence selected from the group consisting of SEQ ID NOs: 34, 2, 4, 6, 8, 10, 12, 14, 16, 18, 20, 22, 24, 26, 28, 30, 32, 36, 38, 40, 42, 44, 46, 48, 53, 54, 55, 56, 57, and 58.

8. The methanotrophic bacteria of claim 7, wherein the reference amino acid sequence is selected from the group consisting of SEQ ID NOs: 34, 16, and 24.

9. The methanotrophic bacteria of claim 1, wherein the heterologous nucleic acid encodes a lactate dehydrogenase having an amino acid sequence selected from the group consisting of SEQ ID NOs: 34, 2, 4, 6, 8, 10, 12, 14, 16, 18, 20, 22, 24, 26, 28, 30, 32, 36, 38, 40, 42, 44, 46, 48, 53, 54, 55, 56, 57, and 58.

10. The methanotrophic bacteria of claim 1, wherein the heterologous nucleic acid comprises a nucleic acid sequence selected from the group consisting of SEQ ID NOS: 33, 1, 3, 5, 7, 9, 11, 13, 15, 17, 19, 21, 23, 25, 27, 29, 31, 35, 37, 39, 41, 43, 45, and 47.

11. The methanotrophic bacteria according to claim 1, wherein the heterologous nucleic acid molecule encodes an LDH from a microorganism selected from the group consisting of *Listeria marthii, Actinomyces viscosus, Acinonyx jubatus, Archilochus colubris, Bacillus anthracis, Bacillus caldolyticus, Bacillus coagulans, Bacillus megaterium, Bacillus stearothermophilus* (Q9p4b6) (also known as *Geobacillus stearothermophilus*), *Bacillus subtilis, Bacillus thuringiensis, Bacteroides pectinophilus, Bifidobacterium longum, Bos taurus, Canis familiaris, Canis lupus, Deinococcus radiodurans, Enterococcus faecalis, Enterococcus faecium, Equus ferus, Felis catus, Kluyveromyces lactis, Kluyveromyces maxxianus, Lactobacillus acidophilus, Lactobacillus bulgaricus, Lactobacillus casei, Lactobacillus coryniformis* sp. *torquens, Lactobacillus delbrueckii* (including subsp. *bulgaricus*), *Lactobacillus fermentum, Lactobacillus helveticus, Lactobacillus johnsonii, Lactobacillus pentosus, Lactobacillus plantarum, Lactobacillus rhamnosus, Lactococcus lactis, Listeria monocytogenes, Plasmodium falciparum, Plasmodium ovale, Thermus thermophilus, Mus musculus, Oryctolagus cuniculus, Pediococcus acidilactici, Taeniopygia guttata, Rattus norvegicus, Rhizopus oryzae, Staphylococcus aureus, Streptococcus bovis, Streptococcus pasteurianus, Ruminococcus torques, Staphylococcus simiae, Staphylococcus vitulinus, Staphylococcus lentus, Macrococcus caseolyticus, Bacillus thuringiensis* seovar konkukian str. 97-27, *Bacillus thuringiensis* serovar chinensis CT-43, and *Bacillus mycoides*.

12. The methanotrophic bacteria according to claim 1, wherein the heterologous nucleic acid sequence encoding LDH is codon optimized for expression in the methanotrophic bacteria.

13. The methanotrophic bacteria according to claim 1, wherein the heterologous nucleic acid molecule encoding the lactate dehydrogenase is operatively linked to an inducible promoter.

14. The methanotrophic bacteria according to claim 1, wherein the lactate dehydrogenase is L-lactate dehydrogenase.

15. The methanotrophic bacteria according to claim 1, wherein the lactate dehydrogenase is a D-lactate dehydrogenase.

16. A method of producing lactate, comprising culturing the methanotrophic bacteria of claim 1 in the presence of a carbon feedstock comprising methane under conditions sufficient to produce lactate, wherein the methanotrophic bacteria convert methane to lactate.

17. The method of claim 16, wherein the carbon feedstock is natural gas.

18. The method of claim 16, wherein conditions sufficient to produce lactate comprise culturing the methanotrophic bacteria in a fermentation medium that comprises a buffer.

* * * * *